US009981977B2

(12) United States Patent
Rauniyar et al.

(10) Patent No.: US 9,981,977 B2
(45) Date of Patent: May 29, 2018

(54) ASYMMETRIC ELECTROPHILIC FLUORINATION USING AN ANIONIC CHIRAL PHASE-TRANSFER CATALYST

(71) Applicant: THE REGENTS OF THE UNIVERSITY OF CALIFORNIA, Oakland, CA (US)

(72) Inventors: Vivek Rauniyar, Berkeley, CA (US); Aaron D. Lackner, Berkeley, CA (US); Gregory L. Hamilton, San Mateo, CA (US); F. Dean Toste, Berkeley, CA (US); Robert J. Phipps, Albany, CA (US); Hunter Shunatona, Berkeley, CA (US); Natalja Frueh, Berkeley, CA (US); Yiming Wang, Berkeley, CA (US); Jeffrey Wu, Berkeley, CA (US); Jigar Patel, Berkeley, CA (US); Takashi Honjo, Berkeley, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 0 days. days.

(21) Appl. No.: 14/368,105

(22) PCT Filed: Dec. 26, 2012

(86) PCT No.: PCT/US2012/071667
§ 371 (c)(1),
(2) Date: Jun. 23, 2014

(87) PCT Pub. No.: WO2013/096971
PCT Pub. Date: Jun. 27, 2013

(65) Prior Publication Data
US 2014/0350253 A1 Nov. 27, 2014

Related U.S. Application Data

(60) Provisional application No. 61/579,633, filed on Dec. 22, 2011.

(51) Int. Cl.
*C07D 487/08* (2006.01)
*C07F 9/6574* (2006.01)
*C07D 215/20* (2006.01)
*C07D 217/22* (2006.01)
*C07D 221/10* (2006.01)
*C07C 231/12* (2006.01)
*C07D 263/10* (2006.01)
*C07D 263/52* (2006.01)
*C07D 265/16* (2006.01)
*C07D 491/052* (2006.01)
*C07D 498/10* (2006.01)
*C07D 209/76* (2006.01)
*C07B 53/00* (2006.01)
(Continued)

(52) U.S. Cl.
CPC ........ *C07D 487/08* (2013.01); *B01J 31/0285* (2013.01); *C07B 53/00* (2013.01); *C07C 45/29* (2013.01); *C07C 45/30* (2013.01); *C07C 231/12* (2013.01); *C07D 209/76* (2013.01); *C07D 215/20* (2013.01); *C07D 217/22* (2013.01); *C07D 221/10* (2013.01); *C07D 263/10* (2013.01); *C07D 263/52* (2013.01); *C07D 265/16* (2013.01); *C07D 491/052* (2013.01); *C07D 498/10* (2013.01); *C07F 9/09* (2013.01); *C07F 9/65744* (2013.01); *B01J 2231/4288* (2013.01); *B01J 2231/48* (2013.01); *C07B 2200/07* (2013.01); *C07C 2601/04* (2017.05); *C07C 2601/14* (2017.05); *C07C 2601/16* (2017.05); *C07C 2602/10* (2017.05); *C07C 2602/24* (2017.05); *C07C 2602/28* (2017.05); *C07C 2603/72* (2017.05)

(58) Field of Classification Search
CPC .................................................. C07D 487/08
See application file for complete search history.

(56) References Cited

U.S. PATENT DOCUMENTS

2009/0030216 A1\* 1/2009 List et al. ............... 549/513

OTHER PUBLICATIONS

"The Chemistry of Halogens." © 2009. Available from: < http://chemed.chem.purdue.edu/genchem/topicreview/bp/ch10/group7.php >.\*
"Electronegativity." © 2015. Available from: < http://www.chemguide.co.uk/atoms/bonding/electroneg.html >.\*
"Bromine: electronegativity." © 2015. Available from: < http://www.webelements.com/bromine/electronegativity.html >.\*
"Chlorine: electronegativity." © 2015. Available from: < http://www.webelements.com/chlorine/electronegativity.html.\*

(Continued)

Primary Examiner — Noble E Jarrell
Assistant Examiner — John S Kenyon
(74) Attorney, Agent, or Firm — Morgan, Lewis & Bockius LLP; Jeffry S. Mann

(57) ABSTRACT

The discovery of distinct modes of asymmetric catalysis has the potential to rapidly advance chemists' ability to build enantioenriched molecules. As an example, the use of chiral cation salts as phase-transfer catalysts for anionic reagents has enabled a vast set of enantioselective transformations. A largely overlooked analogous mechanism wherein a chiral anionic catalyst brings a cationic species into solution is itself a powerful method. The concept is broadly applicable to a number of different reaction pathways, including to the enantioselective fluorocyclization of olefins, and dearomatization of aromatic systems with a cationic electrophile-transferring (e.g., fluorinating) agent and a chiral phosphate catalyst. The reactions proceed in high yield and stereoselectivity. The compounds and methods of the invention are of particular value, especially considering the scarcity of alternative approaches.

8 Claims, 11 Drawing Sheets

(51) Int. Cl.
  *C07C 45/30*    (2006.01)
  *B01J 31/02*    (2006.01)
  *C07C 45/29*    (2006.01)
  *C07F 9/09*     (2006.01)

(56) References Cited

Suzuki, S., et al. "Asymmetric fluorination of β-keto esters catalyzed by chiral rare earth perfluorinated organophosphates." Asymmetry. (2006), vol. 17, pp. 504-507.*
Bloom, S. et al., "Tricomponent Catalytic α,α-Difluorination of Acid Chlorides." Org. Lett. 2011; 13, 5068-5071.
Lozano, O. et al., "Organocatalyzed enantioselective fluorocyclizations." Angew. Chem. Int. Ed. 2011; 50(35):8105-9.
Shibata N.; Suzuki E.; Takeuchi Y. "A fundamentally new approach to enantioselective fluorination based on cinchona alkaloid derivatives/Selectfluor combination." J. Am. Chem. Soc. 2000; 122, 10728.
Wang, X. et al., "Chiral bifunctional phase transfer catalysts for asymmetric fluorination of beta-keto esters." Chem Commun (Camb). 2010;46(2):321-3.
Wilkinson, S. C., et al., "Developments in fluorocyclization methodologies." Future Med. Chem. 2009; vol. 1, No. 5, 847-863.

* cited by examiner

R¹ = Bn:
4b, 81% yield, 97% ee

R¹ = Ph:
4c, 55% yield, 90% ee

R¹ = Homoallyl:
4d, 65% yield, 90% ee

R¹ = Allyl:
4e, 71% yield, 87% ee

R¹ = iPr:
4f, 96% yield, 91% ee

R¹ = Cy, R³ = Me:
4g, 75% yield, 79% ee

R¹ = Allyl, R² = Me:
4h, 51% yield, 92% ee

R¹ = Bn, R³ = Me:
4i, 67% yield, 90% ee

R¹ = (CH$_2$)$_2$OTBS:
4j, 77% yield, 91% ee

ASYMMETRIC ELECTROPHILIC FLUORINATION USING AN ANIONIC CHIRAL PHASE-TRANSFER CATALYST

BACKGROUND OF THE INVENTION

In the years since Knowles and co-workers demonstrated that synthetic catalysts could approach the levels of absolute stereocontrol achieved by enzymes (B. D. Vineyard, W. S. Knowles, M. J. Sabacky, G. L. Bachman, D. J. Weinkauff, Asymmetric hydrogenation. Rhodium chiral bisphosphine catalyst, *J. Am. Chem. Soc.* 99, 5946 (1977)), chemists have made remarkable progress on the synthesis of optically active molecules using catalytic chiral inputs. Despite the advances, the subset of reactions that can be performed with enantioselective methods still represents only a fraction of the pool of known organic transformations. One reason for this discrepancy is that although new ligand designs and catalyst variants have been reported at a striking rate, a slower pace has been set for devising alternative underlying approaches to inducing asymmetry.

Among the distinct strategies that complement the traditional metal-chiral ligand methods, asymmetric phase-transfer catalysis has undoubtedly been one of the most successful. In this mode of catalysis, a lipophilic chiral cation salt mediates the reaction between a substrate in organic solution and an anionic reagent in a separate aqueous or solid phase. Ion-pairing with the cation solubilizes the anionic reagent or reaction intermediate in the bulk organic phase, while also providing a chiral environment for the desired reaction with the substrate. Application of this simple logic has yielded a diverse array of operationally simple, highly enantioselective protocols (K. Maruoka, Ed., *Asymmetric Phase Transfer Catalysis* (Wiley-VCH, Weinheim, Germany, 2008); M. J. O'Donnell, in *Catalytic Asymmetric Synthesis*, I. Ojima, Ed. (Wiley-VCH, New York, 2000), 2nd ed. chap. 10, pp. 727; T. Ooi, K. Maruoka, Recent advances in asymmetric phase-transfer catalysis, *Angew. Chem. Int. Ed.* 46, 4222 (2007); B. Lygo, B. I. Andrews, Asymmetric phase-transfer catalysis utilizing chiral quaternary ammonium salts: asymmetric alkylation of glycine imines, *Acc. Chem. Res.* 37, 518 (2004)).

However, almost no consideration has been given to an analogous charge-inverted strategy in which the salt of a chiral anion brings an insoluble cationic promoter into solution. This neglected other half of phase-transfer catalysis could be quite useful. An area of chemistry with broad utility in which charge-inverted phase-transfer catalysis play a role would be uniquely advantageous.

Procedures for the construction of carbon-fluorine bonds are highly prized due to the scarcity of methods and the value of the products across applied chemistry (I. Ojima, Ed., *Fluorine in Medicinal Chemistry and Chemical Biology* (Wiley-Blackwell, 2009); S. Purser, P. R. Moore, S. Swallow, V. Gouverneur, Fluorine in medicinal chemistry, *Chem. Soc. Rev.* 37, 320 (2008); T. Furuya, A. S. Kamlet, T. Ritter, Catalysis for fluorination and trifluoromethylation, *Nature* 473, 470 (2011); M. H. Katcher, A. Sha, A. G. Doyle, Palladium-catalyzed regio- and enantioselective fluorination of acyclic allylic halides, *J. Am. Chem. Soc.* 133, 15902 (2011)). Within the realm of drug design, the stereospecific incorporation of fluorine substituents is a powerful and widely employed tactic to circumvent metabolism issues arising from in vivo C—H bond oxidation. On this basis, the catalytic production of carbon-fluorine stereogenicity has become a methodological goal of central importance to practitioners of chemical and pharmaceutical synthesis. Surprisingly, however, catalytic methods for the asymmetric construction of C—F bonds are rare, the majority involving α-substituted β-keto ester substrates that are structurally precluded from product epimerization (see Hamashima et al. (2005) *Tetrahedron Lett.* 46:1447; Shibara et al. (2004) *Synlett.* 1703; Ma et al. (2004) *Tetrahedron Asym.* 1007; Kim (2002) *Org. Lett.* 4:545).

Electrophilic reagents have proven to be one of the most applicable vehicles for introducing fluorine into organic molecules (S. Stavber, Recent advances in the application of Selectfluor F-TEDA-BF4 as a versatile mediator or catalyst in organic synthesis, *Molecules* 16, 6432 (2011); J. Baudoux, D. Cahard, in *Organic Reactions*, S. E. Denmark, Ed. (Wiley, Hoboken, 2007), ch. 2, pp. 347-672; P. T. Nyffeler, S. G. Duron, M. D. Burkart, S. P. Vincent, C.-H. Wong, Selectfluor: Mechanistic insight and applications, *Angew. Chem. Int. Ed.* 44, 192 (2005); C. Bobbio, V. Gouverneur, Catalytic asymmetric fluorinations, *Org. Biomol. Chem.* 4, 2065 (2006); J.-A. Ma, D. Cahard, Asymmetric fluorination, trifluoromethylation, and perfluoroalkylation reactions, *Chem. Rev.* 108, PR1 (2008); S. Lectard, Y. Hamashima, M. Sodeoka, Recent advances in catalytic enantioselective fluorination reactions, *Adv. Synth. Catal.* 352, 2708 (2010)). Unfortunately, the mechanism of these reactions offers little room for addition of a chiral catalyst. Many of the most effective published enantioselective fluorination protocols involve formation of a nucleophilic chiral enolate equivalent (L. Hintermann, A. Togni, Catalytic enantioselective fluorination of β-ketoesters, *Angew. Chem. Int. Ed.* 39, 4359 (2000); T. Suzuki, T. Goto, Y. Hamashima, M. Sodeoka, Enantioselective fluorination of tertbutoxycarbonyl lactones and lactams catalyzed by chiral Pd(II)-bisphosphine complexes, *J. Org. Chem.* 72, 246 (2007); Y. Hamashima, T. Suzuki, Y. Shimura, T. Shimizu, N. Umebayashi, T. Tamura, N. Sasamoto, M. Sodeoka, An efficient catalytic enantioselective fluorination of β-ketophosphonates using chiral palladium complexes, *Tetrahedron Lett.* 46, 1447 (2005); H. R. Kim, D. Y. Kim, Catalytic enantioselective fluorination of α-cyano acetate catalyzed by chiral palladium complexes, *Tetrahedron Lett.* 46, 3115 (2005); X. Wang, Q. Lan, S. Shirakawa, K. Maruoka, Chiral bifunctional phase transfer catalysts for asymmetric fluorination of β-keto esters, *Chem. Commun.* 46, 321 (2010); M. Marigo, D. Fielenbach, A. Braunton, A. Kjærsgaard, K. A. Jørgensen, Enantioselective formation of stereogenic carbon-fluorine centers by a simple catalytic method, *Angew. Chem. Int. Ed.* 44, 3703 (2005); D. D. Steiner, N. Mase, C. F. Barbas III, Direct asymmetric α-fluorination of aldehydes, *Angew. Chem. Int. Ed.* 44, 3706 (2005); T. D. Beeson, D. W. C. MacMillan, Enantioselective organocatalytic α-fluorination of aldehydes. *J. Am. Chem. Soc.* 127, 8826 (2005); P. Kwiatkowski, T. D. Beeson, J. C. Conrad, D. W. C. MacMillan, Enantioselective organocatalytic α-fluorination of cyclic ketones, *J. Am. Chem. Soc.* 133, 1738 (2011)), including one report of formation through chiral cationic phase transfer catalysis (X. Wang, Q. Lan, S. Shirakawa, K. Maruoka, Chiral bifunctional phase transfer catalysts for asymmetric fluorination of β-keto esters. *Chem. Commun.* 46, 321 (2010)). On the other hand, the catalytic generation of a chiral electrophile has proven quite challenging; usually a stoichiometric amount of chiral promoter is necessary to suppress the racemic background reaction (D. Cahard, C. Audouard, J.-C. Plaquevent, N. Rogues, Design, synthesis, and evaluation of a novel class of enantioselective electrophilic fluorinating reagents: N-fluoro ammonium salts of cinchona alkaloids (F-CA-BF4). *Org. Lett.* 2, 3699 (2000); N. Shibata, E. Suzuki, Y. Takeuchi, A fundamentally new approach to enantioselective fluorination based on cinchona alkaloid derivatives/Selectfluor combination, *J. Am. Chem. Soc.* 122, 10728 (2000); T. Ishimaru, N. Shibata, T. Horikawa, N. Yasuda, S. Nakamura, T. Toni, M. Shiro, Cinchona alkaloid catalyzed enantioselective fluorination of allyl silanes, silyl enol ethers, and oxindoles, *Angew. Chem. Int. Ed.* 47, 4157 (2008); O. Lozano, G. Blessley, T. Martinez del Campo, A. L. Thompson, G. T. Giuffredi, M. Bettati, M. Walker, R. Borman, V. Gouverneur, Organocatalyzed enantioselective fluorocyclizations, *Angew. Chem. Int. Ed.* 50, 8105 (2011)).

There is, accordingly, a need in the art for an improved enantioselective fluorination method. An ideal method would enable rapid and enantiocontrolled C—F bond formation using stable, inexpensive reagents and catalysts that are inert to product epimerization and readily allow the fluorinated compound to be further functionalized. The introduction of chiral anion phase-transfer catalysts of use in catalyzing electrophilic reactions, e.g., halogenation, and methods of using these catalysts would represent a significant advance in the art. The present invention provides such catalysts and methods for carrying out electrophilic addition reactions mediated by chiral anion phase-transfer catalysts.

SUMMARY OF THE INVENTION

The demand for enantiomerically pure compounds has grown rapidly in recent years. One important use for such chiral, non-racemic compounds is as intermediates for synthesis in the pharmaceutical industry. For instance, it has become increasingly clear that enantiomerically pure drugs have many advantages over racemic drug mixtures. The advantages of enantiomerically pure compounds (reviewed in, e.g., Stinson, S. C., Chem Eng News, Sep. 28, 1992, pp. 46-79) include fewer side effects and greater potency in many cases.

Traditional methods of organic synthesis have often been optimized for the production of racemic materials. The production of enantiomerically pure material has historically been achieved in one of two ways: the use of enantiomerically pure starting materials derived from natural sources (the so-called "chiral pool"); or the resolution of racemic mixtures by classical techniques. Each of these methods has serious drawbacks, however. The chiral pool is limited to compounds found in nature, so only certain structures and absolute configurations are readily available. Resolution of racemates often requires the use of resolving agents; this process may be inconvenient and is certain to be time-consuming. Furthermore, resolution often means that the undesired enantiomer is discarded, thereby wasting half of the material. The compositions and methods of the present invention represent a significant improvement over classical techniques and their drawbacks.

The present invention provides a novel family of chiral catalysts for electrophilic addition reactions. The catalysts are salts including a chiral anionic component and a cationic component. The cationic component is a donor for the electrophilic component (e.g., F+, Br+, I+, Ar+) added in the electrophilic addition reaction. In various embodiments, the cationic component is essentially insoluble in the solvent in which the catalyst is to be used to accomplish an electrophilic addition. In contrast, the chiral anionic component of the catalyst is substantially soluble in the reaction solvent. The salt formed by combining the chiral anion and the cation is soluble in the reaction solvent to at least an amount sufficient to catalyze the desired electrophilic addition reaction. An exemplary catalyst is a complex between a positively charged donor of an electrophilic species (e.g., F+, Cl+, Br+, I+, Ar+) and a negatively charged chiral phosphoric acid ligand (FIG. 1). In an exemplary embodiment, the donor of an electrophilic species is Selectfluor, or the corresponding bromo analog thereof.

The invention also provides methods of performing electrophilic addition reactions catalyzed by the catalysts of the invention.

In an exemplary embodiment, the invention provides a method of adding an electrophilic species to a pi-bond using a catalyst of the invention. In various embodiments, the invention provides a method of cyclizing a substrate having one or more pi bond within the substrate structure (FIG. 2-4). In various embodiments, the cyclized product is substituted with the electrophilic species donated by the catalyst. According to this method, the substrate is contacted with a catalyst of the invention under conditions appropriate to produce the cyclized product.

In an exemplary embodiment, the invention provides a method of adding an electrophilic species to the alpha position of an enamine. The method includes contacting an enamine substrate with a catalyst of the invention under conditions appropriate to add the electrophilic species to the alpha position of the enamine. See, Example 7.

In various embodiments, the invention provides a method of dearomatizing an aromatic substrate. The method includes contacting an aromatic substrate (e.g., a substituted or unsubstituted phenol) with a catalyst of the invention under conditions appropriate to produce the dearomatized product. In an exemplary embodiment, the catalyst adds an electrophilic halogen species to the aromatic system effecting the dearomatization. In various embodiments, the electrophilic halogen species is $Cl^+$, $I^+$, $F^+$ or $Br^+$ (FIG. 5-9).

Additional embodiments, objects and advantages of the invention are set forth in the detailed description below.

DETAILED DESCRIPTION OF THE EMBODIMENTS

I. Introduction

The ability to selectively transform a prochiral center in a compound to an enantiomerically enriched or enantiomerically pure chiral center has broad application, especially in the agricultural, pharmaceutical, and polymer industries. As described herein, the present invention relates to catalysts and methods for the catalytic asymmetric transformation of a prochiral center in a compound to an enantiomerically enriched or enantiomerically pure chiral center. The catalysts of the present invention are chiral, non-racemic compounds that function as phase transfer catalysts in certain asymmetric synthetic organic transformations.

Figure 1:
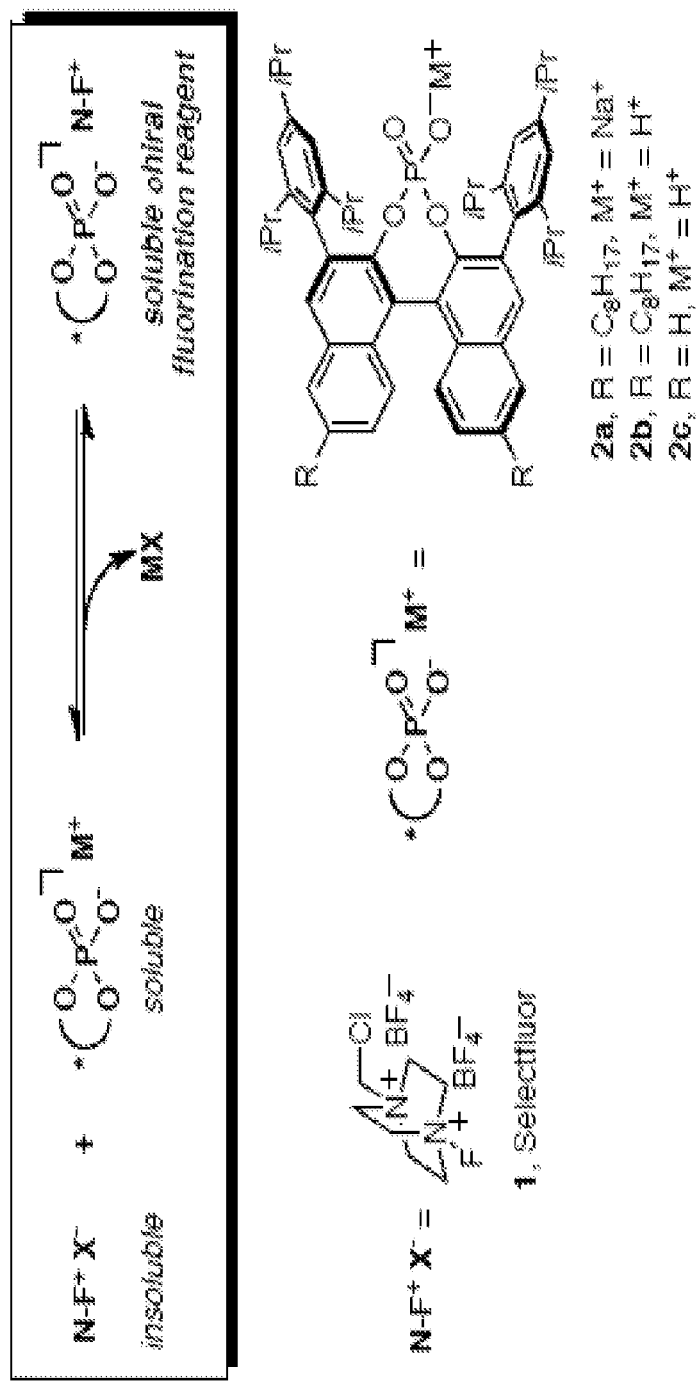
FIG. 1 is an exemplary method for preparing a catalyst of the invention. An exemplary embodiment is illustrated by reference to the use of Selectfluor (1) as the cation and various chiral phosphate ligands (2a, 2b and 2c) as the soluble anion.
Figure 2:
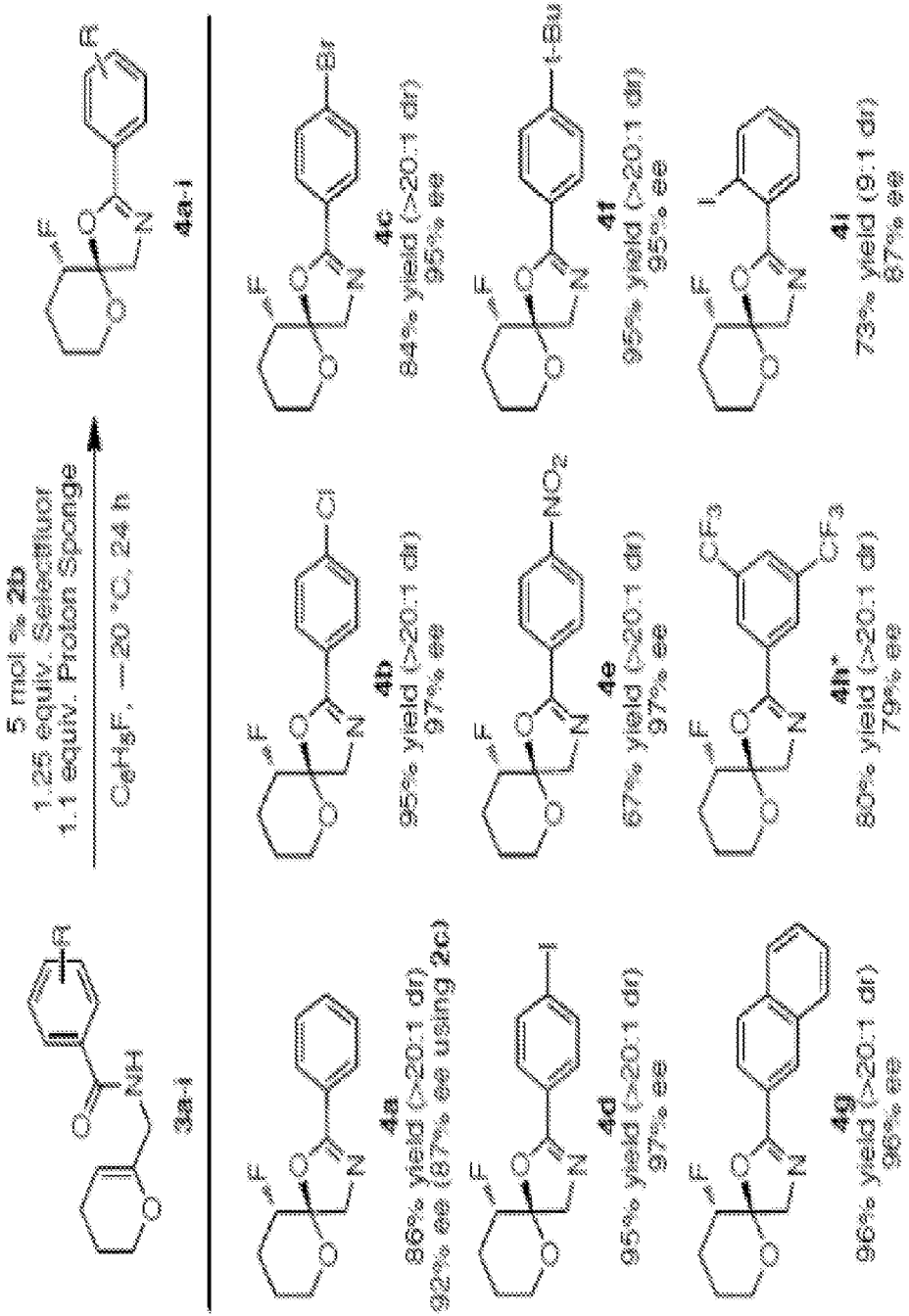
FIG. 2 shows the enantioselective synthesis of fluorinated heterocycles from dihydropyran-derived substrates. The reactions were run at −5° C.
Figure 3:
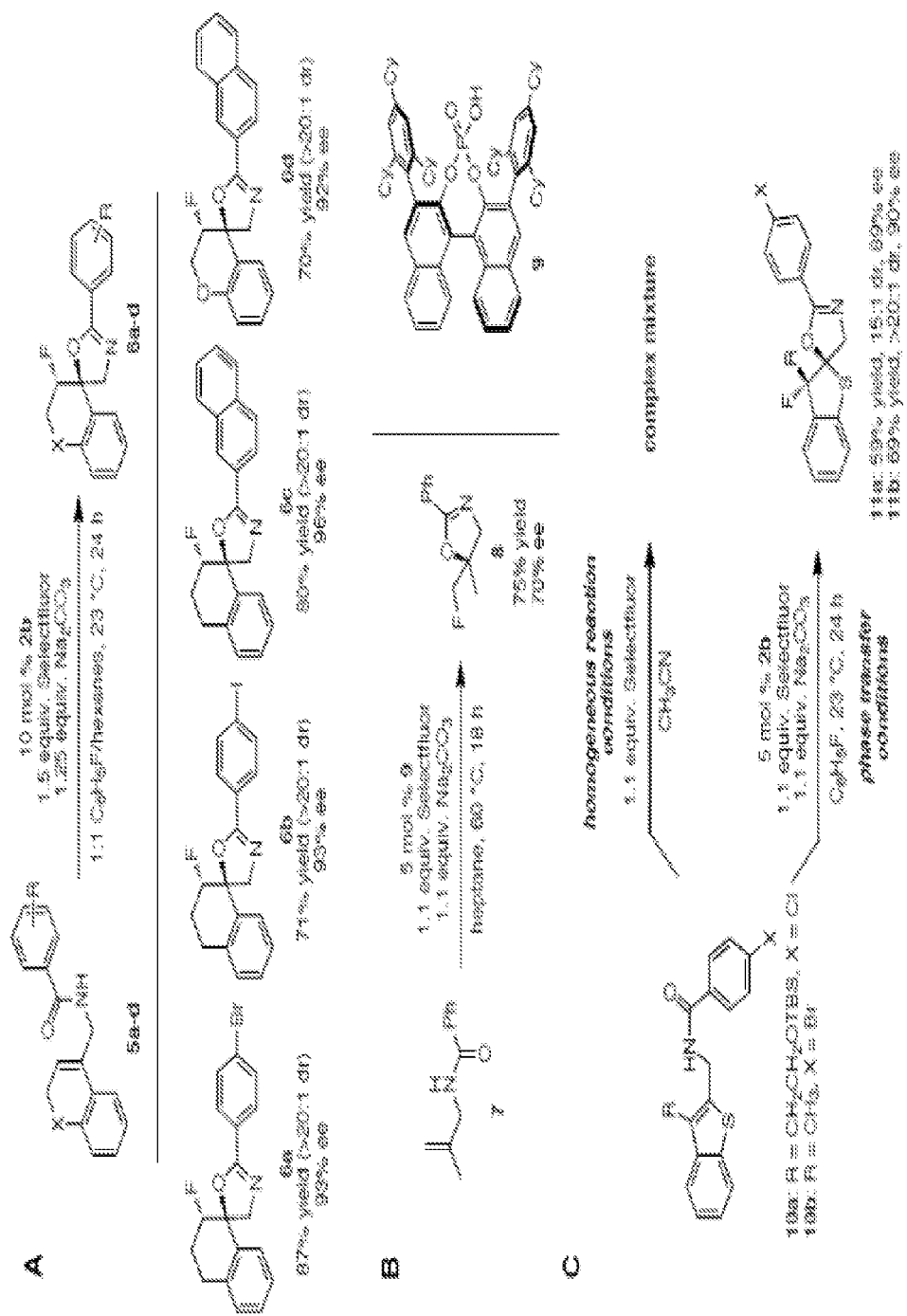
FIG. 3 (A) Fluorocyclization of dihydronaphthalenes and chromenes. (B) Successful extension to an unactivated alkene. (C) The phase transfer procedure displays improved chemoselectivity over homogeneous conditions.
Figure 4:
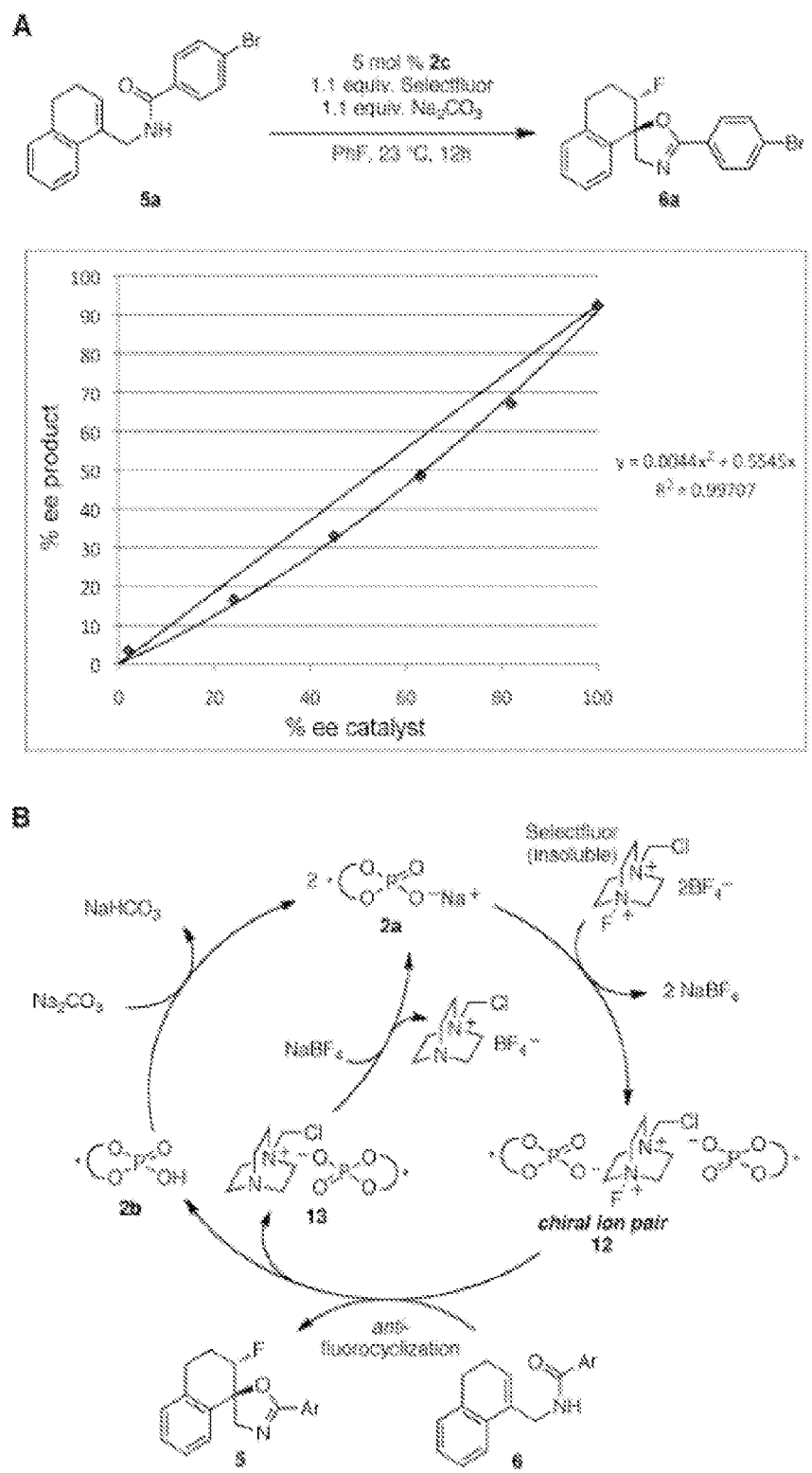
FIG. 4 (A) Nonlinear relationship between the optical activity of catalyst and product in the fluorocyclization reaction. (B) An exemplary catalytic cycle supported by the observed non-linear effect.
Figure 5A:
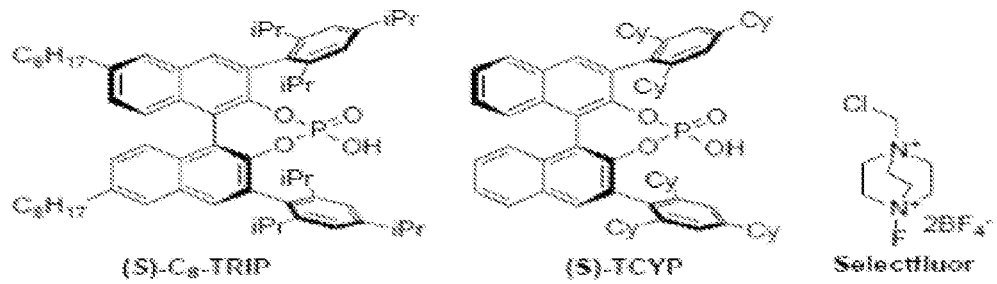
FIG. 5 is the results of an investigation and selected optimization of the effect of phenol substitution on fluorination regio- and stereo-specificity: (A) catalysts/reagents employed; (B) Para fluorination; (C) Ortho fluorination; (D) Ortho fluorination/[4+2] dimerization. [a] Isolated yields after chromatography on silica gel. [b] ee Determination determined by HPLC; [c] Yield determined by 1H-NMR with internal standard.
Figure 5B:
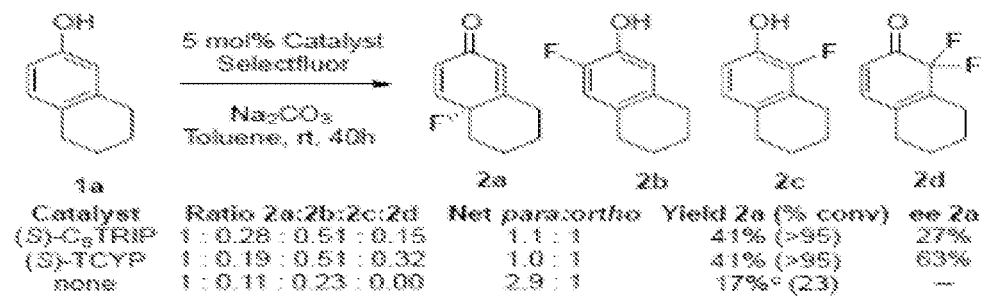
Figure 5C:
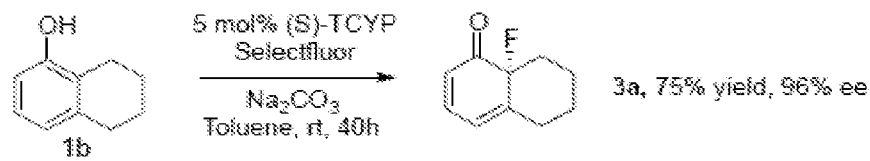
Figure 5D:
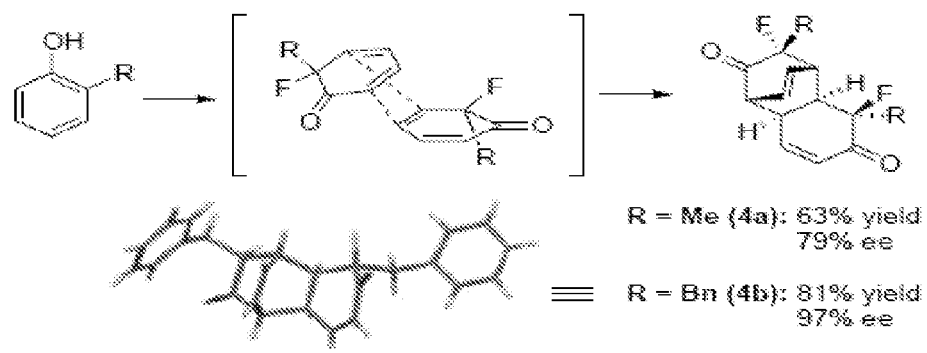
Figure 6A:
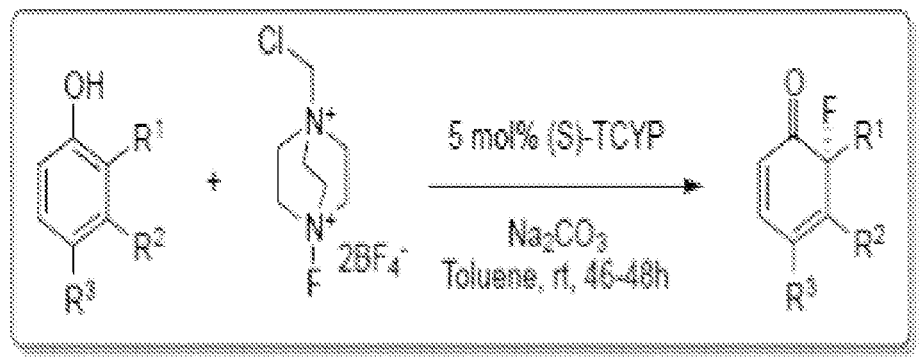
FIG. 6 is an example of the scope of fluorinative dearomatization of a range of 2,3-di- and 2,3,4-tri-substituted phenols. The absolute stereochemistries were assigned by analogy with 4b.
Figure 6B:
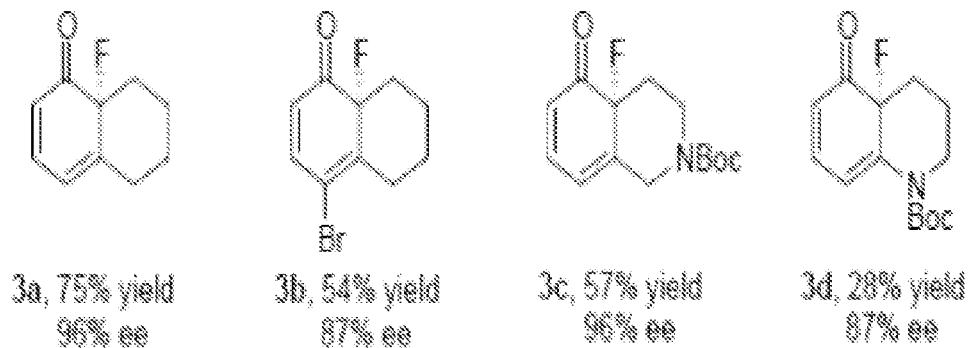
Figure 6C:
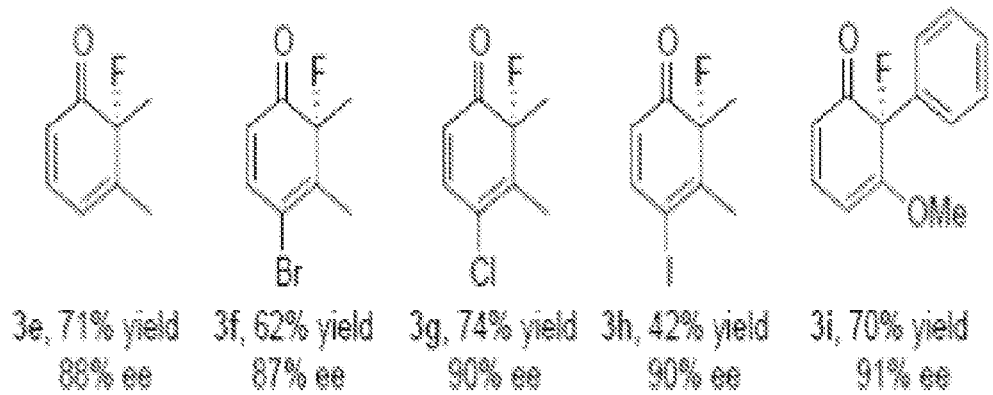
Figure 7A:
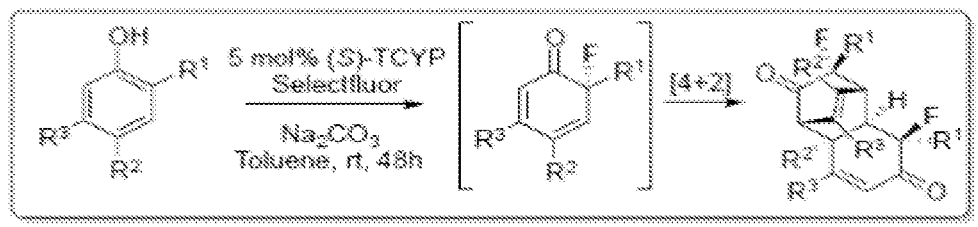
FIG. 7 shows examples of fluorination[4+2] dimerization of phenols lacking 3-substitution.
Figure 7B:
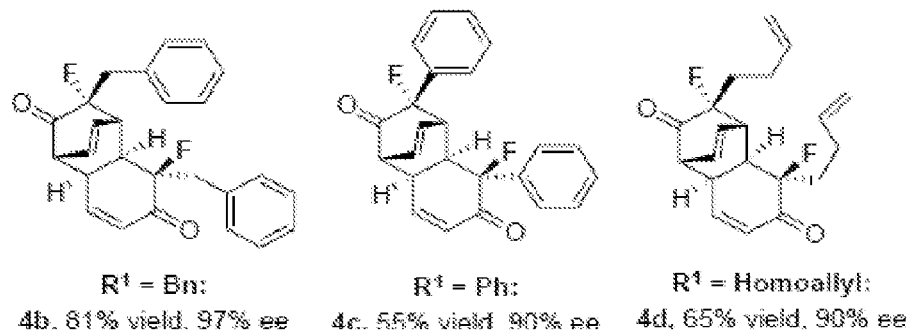
Figure 7C:
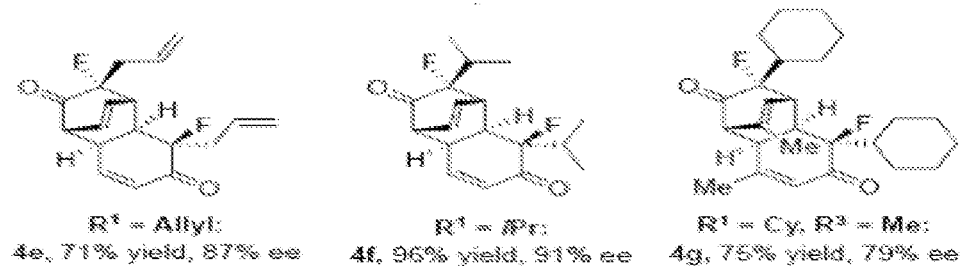
Figure 7D:
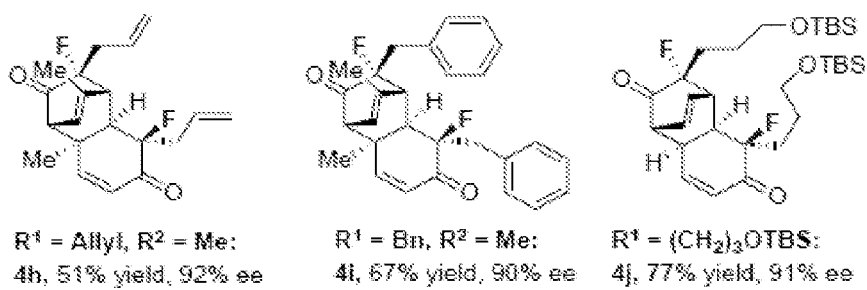

In various embodiments, the invention is directed to the aforementioned need in the art, and provides a new technique for effecting enantioselective addition of an electrophilic species to a pi bond. The invention also provides catalysts of use in performing such enantioselective electrophilic additions, e.g., fluorination (FIG. 1). The method involves contacting a substrate having a pi bond, e.g., contacting an alkene, an enamine or an aryl moiety (e.g., substituted or unsubstituted phenol) with a catalyst of the invention, which is a complex between a cationic electrophilic (e.g. fluorination) reagent and a chiral anionic species. Exemplary methods of the invention convert pi bonded substrates to cyclized analogs of such substrates, which are substituted with the electrophilic component of the catalyst (FIG. 2-4). Other methods add an electrophilic species to the alpha position of an enamine (see, Example 7). Still further methods dearomatize aromatic substrates with the concomitant addition of the electrophilic species of the catalyst to the substrate (FIG. 5-10). Each of these methods includes contacting the desired substrate with a catalyst of the invention under conditions appropriate to convert the substrate to the desired reaction product.

An exemplary catalyst is readily synthesized from inexpensive, commercially available reagents, is compatible with aerobic conditions, and provides the desired enantioselective fluorination products in high yield with a high level of enantioselectivity. In an exemplary embodiment, the chiral anion solubilizes a halogenation, e.g., fluorination or bromination, reagent, which is otherwise essentially insoluble in a non-polar organic solvent, by forming a complex, e.g., a salt, with the halogenation reagent. In these embodiments, the chiral catalyst may operate on the principle of phase-transfer. In various embodiments, the asymmetry of the chiral, non-racemic phase transfer catalyst combines with the steric bulk of the reagent electrophile to give enhanced stereoselectivity in the methods of the present invention. Moreover, the preferably sterically bulky reagent electrophile may be generated in situ or prepared in a prior step.

Before the invention is described in greater detail, it is to be understood that the invention is not limited to particular embodiments described herein as such embodiments may vary. It is also to be understood that the terminology used herein is for the purpose of describing particular embodiments only, and the terminology is not intended to be limiting. The scope of the invention will be limited only by the appended claims. Unless defined otherwise, all technical and scientific terms used herein have the same meaning as commonly understood by one of ordinary skill in the art to which this invention belongs. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number. All publications, patents, and patent applications cited in this specification are incorporated herein by reference to the same extent as if each individual publication, patent, or patent application were specifically and individually indicated to be incorporated by reference. Furthermore, each cited publication, patent, or patent application is incorporated herein by reference to disclose and describe the subject matter in connection with which the publications are cited. The citation of any publication is for its disclosure prior to the filing date and should not be construed as an admission that the invention described herein is not entitled to antedate such publication by virtue of prior invention. Further, the dates of publication provided might be different from the actual publication dates, which may need to be independently confirmed.

It is noted that the claims may be drafted to exclude any optional element. As such, this statement is intended to serve as antecedent basis for use of such exclusive terminology as "solely," "only," and the like in connection with the recitation of claim elements, or use of a "negative" limitation. As will be apparent to those of skill in the art upon reading this disclosure, each of the individual embodiments described and illustrated herein has discrete components and features which may be readily separated from or combined with the features of any of the other several embodiments without departing from the scope or spirit of the invention. Any recited method may be carried out in the order of events recited or in any other order that is logically possible. Although any methods and materials similar or equivalent to those described herein may also be used in the practice or testing of the invention, representative illustrative methods and materials are now described.

In describing the present invention, the following terms will be employed, and are intended to be defined as indicated below.

II. Definitions

As used in this specification and the appended claims, the singular forms "a", "an" and "the" include plural referents unless the content explicitly dictates otherwise. Thus, for example, reference to "cationic nickel catalyst" includes a mixture of two or more such compounds, and the like.

Where substituent groups are specified by their conventional chemical formulae, written from left to right, the structures optionally also encompass the chemically identical substituents, which would result from writing the structure from right to left, e.g., —CH$_2$O— is intended to also recite —OCH$_2$—.

The term "alkyl," by itself or as part of another substituent, means, unless otherwise stated, a straight or branched chain, or cyclic hydrocarbon radical, or combination thereof, which may be fully saturated, mono- or polyunsaturated and can include di-, tri- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to optionally include those derivatives of alkyl defined in more detail below, such as "heteroalkyl." Alkyl groups that are limited to hydrocarbon groups are termed "homoalkyl". Exemplary alkyl groups include the monounsaturated $C_{9-10}$, oleoyl chain or the diunsaturated $C_{9-10, 12-13}$ linoeyl chain.

The term "alkylene" by itself or as part of another substituent means a divalent radical derived from an alkane, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The terms "aryloxy" and "heteroaryloxy" are used in their conventional sense, and refer to those aryl or heteroaryl groups attached to the remainder of the molecule via an oxygen atom.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —CO$_2$R'— represents both —C(O)OR' and —OC(O)R'.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Further exemplary cycloalkyl groups include steroids, e.g., cholesterol and its derivatives. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms selected from N, O, S, Si and B, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to optionally include both substituted and unsubstituted forms of the indicated radical. Exemplary substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: H, substituted or unsubstituted aryl, substituted or unsubstituted heteroaryl, substituted or unsubstituted heterocycloalkyl, —OR', =O, =NR', =N—OR', —NR'R", —SR', halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O) CF$_3$, —C(O)CH$_2$OCH$_3$, and the like). These terms encompass groups considered exemplary "alkyl group substituents", which are components of exemplary "substituted alkyl" and "substituted heteroalkyl" moieties.

Similar to the substituents described for the alkyl radical, substituents for the aryl and heteroaryl groups are generically referred to as "aryl group substituents." The substituents are selected from, for example: H, substituted or unsubstituted alkyl, substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system;

and where R', R", R'" and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R' and R"" groups when more than one of these groups is present.

Two of the substituents on adjacent atoms of the aryl or heteroaryl ring may optionally be replaced with a substituent of the formula -T-C(O)—(CRR')$_q$-U-, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$-B-, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R"" are preferably independently selected from hydrogen or substituted or unsubstituted (C$_1$-C$_6$)alkyl. These terms encompass groups considered exemplary "aryl group substituents", which are components of exemplary "substituted aryl" and "substituted heteroaryl" moieties.

As used herein, the term "acyl" describes a substituent containing a carbonyl residue, C(O)R. Exemplary species for R include H, halogen, substituted or unsubstituted alkyl, substituted or unsubstituted aryl, substituted or unsubstituted heteroaryl, and substituted or unsubstituted heterocycloalkyl.

As used herein, the term "fused ring system" means at least two rings, wherein each ring has at least 2 atoms in common with another ring. "Fused ring systems may include aromatic as well as non aromatic rings. Examples of "fused ring systems" are naphthalenes, indoles, quinolines, chromenes and the like.

As used herein, the term "heteroatom" includes oxygen (O), nitrogen (N), sulfur (S) and silicon (Si) and boron (B).

The symbol "R" is a general abbreviation that represents a substituent group that is selected from H, substituted or unsubstituted alkyl, substituted or unsubstituted heteroalkyl, substituted or unsubstituted aryl, substituted or unsubstituted heteroaryl, and substituted or unsubstituted heterocycloalkyl groups.

The term "ligand" has the meaning ordinarily ascribed to it in the art. Exemplary ligands include at least one donor atom capable of binding to a first row metal. Ligands can include sterically bulky species, such as substituted or unsubstituted aryl, substituted or unsubstituted heteroaryl and substituted or unsubstituted fused ring systems, secondary and tertiary alkyl groups and the like. As described below, a ligand of use in the invention can be conceptualized as including a linker joining two or more donor atoms, which are the same or different atoms.

The term "salt(s)" includes salts of the compounds prepared by the neutralization of acids or bases, depending on the particular ligands or substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids, and the like, as well as the salts derived from relatively nontoxic organic acids like acetic, propionic, isobutyric, butyric, maleic, malic, malonic, benzoic, succinic, suberic, fumaric, lactic, mandelic, phthalic, benzenesulfonic, p-tolylsulfonic, citric, tartaric, methanesulfonic, and the like. Certain specific compounds of the present invention contain both basic and acidic functionalities that allow the compounds to be converted into either base or acid addition salts. Hydrates of the salts are also included. An exemplary salt of the invention includes a boron-containing anion, e.g., $B(C_6F_5)_4^-$, $BF_4^-$.

The term "nucleophile" is recognized in the art, and as used herein means a chemical moiety having a reactive pair of electrons. Examples of nucleophiles include uncharged compounds such as water, amines, mercaptans and alcohols, and charged moieties such as alkoxides, thiolates, carbanions, and a variety of organic and inorganic anions. Illustrative anionic nucleophiles include simple anions such as hydroxide, azide, cyanide, thiocyanate, acetate, formate or chloroformate, and bisulfite. Organometallic reagents such as organocuprates, organozincs, organolithiums, Grignard reagents, enolates, acetylides, and the like are suitable nucleophiles, under appropriate reaction conditions. Hydride is also a suitable nucleophile when reduction of the substrate is desired.

The term "electrophile" is art-recognized and refers to chemical moieties which can accept a pair of electrons from a nucleophile as defined above. Electrophiles useful in the method of the present invention include positively charged halogen and positively charged aryl synthons.

The terms "electrophilic atom", "electrophilic center" and "reactive center" as used herein refer to the atom of the substrate which is attacked by, and forms a new bond to, the nucleophile.

The terms "Lewis base" and "Lewis basic" are recognized in the art, and refer to a chemical moiety capable of donating a pair of electrons under certain reaction conditions. Examples of Lewis basic moieties include uncharged compounds such as alcohols, thiols, olefins, and amines, and charged moieties such as sulfonates, phosphates, the anions of alcohols (e.g., diols), and a variety of other organic anions. In various embodiments, the anionic component of the catalyst of the invention is a Lewis base.

The terms "Lewis acid" and "Lewis acidic" are art-recognized and refer to chemical moieties which can accept a pair of electrons from a Lewis base. In various embodiments, the cationic component of the catalyst is a Lewis acid.

The term "chiral" refers to molecules produced by a method of the invention which have the property of non-superimposability on their mirror image partner, while the term "achiral" refers to molecules which are superimposable on their mirror image partner. A "prochiral molecule" is an achiral molecule which has the potential to be converted to a chiral molecule in a particular process. Likewise, a "prochiral center" is an achiral atom in a molecule which has the potential to be converted to a chiral center in a particular process.

The term "stereoisomers" refers to compounds produced by methods of the invention which have identical chemical constitution, but differ with regard to the arrangement of their atoms or groups in space. In particular, the term "enantiomers" refers to two stereoisomers of a compound which are non-superimposable mirror images of one another. The term "diastereomers", on the other hand, refers to the relationship between a pair of stereoisomers that comprise two or more asymmetric centers and are not mirror images of one another.

Furthermore, a "stereoselective process" is a process of the invention which produces a particular stereoisomer of a reaction product in preference to other possible stereoisomers of that product. An "enantioselective process" is one which favors production of one of the two possible enantiomers of a reaction product. The subject method is said to produce a "stereoselectively-enriched" product (e.g., enantioselectively-enriched or diastereoselectively-enriched) when the yield of a particular stereoisomer of the product is greater by a statistically significant amount relative to the yield of that stereoisomer resulting from the same reaction run in the absence of a chiral catalyst. For example, an enantioselective reaction catalyzed by one of the subject chiral catalysts will yield an e.e. for a particular enantiomer that is larger than the e.e. of the reaction lacking the chiral catalyst.

The term "substrate" is intended to mean a chemical compound which can react with a catalyst of the invention, to yield at least one product having a stereogenic center.

The term "catalytic amount" is recognized in the art and refers to a substoichiometric amount of a catalyst of the invention relative to a reactant. As used herein, a catalytic amount means from 0.0001 to 90 mole percent relative to a reactant, more preferably from 0.001 to 50 mole percent, still more preferably from 0.01 to 10 mole percent, and even more preferably from 0.1 to 5 mole percent relative to a reactant.

As discussed more fully below, the reactions contemplated in the present invention include reactions which are enantioselective, diastereoselective, and/or regioselective. An enantioselective reaction is a reaction which converts an achiral reactant to a chiral product enriched in one enantiomer. Enantioselectivity is generally quantified as "enantiomeric excess" (ee) defined as follows: where A and B are the enantiomers formed. Additional terms that are used in conjunction with enatioselectivity include "optical purity" or "optical activity". An enantioselective reaction yields a product with an e.e. greater than zero. Preferred enantioselective reactions according to the invention yield a product with an e.e. greater than 20%, more preferably greater than 50%, even more preferably greater than 70%, and most preferably greater than 80%.

The term "non-racemic" with respect to the chiral catalyst, means a preparation of catalyst having greater than 50% of a given enantiomer, more preferably at least 75%. "Substantially non-racemic" refers to preparations of the catalyst which have greater than 90% ee for a given enantiomer of the catalyst, more preferably greater than 95% ee.

Certain compounds of the present invention possess asymmetric carbon atoms (optical centers) or double bonds; the racemates, diastereomers, geometric isomers and individual isomers are encompassed within the scope of the present invention. Optically active (R)- and (S)-isomers and d and l isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are included.

The compounds disclosed herein may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Below are examples of specific embodiments for carrying out the present invention. The examples are offered for illustrative purposes only, and are not intended to limit the scope of the present invention in any way.

III. The Compounds

In various embodiments, the present invention provides a chiral ion pair formed between a cation having electrophilic donor properties and a bulky chiral anion. In various embodiments, the anion is a chiral phosphoric acid ligand having one or more aryl moieties (FIG. 1). As will be appreciated by those in the art, the substitution pattern on aryl rings of the catalyst can be varied as desired and substituents referred to herein as "aryl group substituents" are exemplary substituents for such aryl rings.

In various embodiments, the chiral catalyst of the invention has the formula:

$$[A]^{n+}[B]^{n-}$$

In an exemplary embodiment, A is a cationic donor of an electrophile. Exemplary electrophiles include those selected from F$^+$, Cl$^+$, Br$^+$, I$^+$ and Ar$^+$. The index n is 1 or 2. Ar$^+$ is a substituted or unsubstituted aryl or substituted or unsubstituted heteroaryl. The symbol B represents a chiral anion, e.g., a phosphoric acid ligand. The chiral anion is a chiral phosphate, a chiral sulfate, a chiral carboxylate or a mono- or di-anion of a chiral diol.

Exemplary anions include one or more moiety on which the pattern of substitution and/or the nature of the substituents is readily varied (e.g., an aryl or heteroaryl moiety), which allows for the facile modification of the steric and/or electronic properties of the anion and provides a route to the tune the steric and/or electronic properties of the compositions of the invention to induce, optimize, minimize or prevent a particular type of reaction mediated by the composition of the invention. Exemplary substituents are those referred to herein as "aryl group substituents". Furthermore, the ease of engineering a composition of the invention allows for the design of a catalyst that functions optimally with a selected substrate or class of substrates. As noted above, in various aspects, the invention provides a compound that includes a phosphate anion.

In various embodiments, the anion of a compound of the invention has the formula:

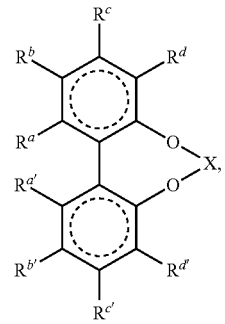

in which X is a member selected from P(O)O$^-$, S(O)$_2$O$^-$, or it represents one or two negative charges on the oxygen(s) of a mono- or di-deprotonated diol. In an exemplary embodiment, R$^a$, R$^b$, R$^c$, R$^d$, R$^{a'}$, R$^{b'}$, R$^{c'}$, R$^{d'}$ are each independently selected from "aryl group substituents", as that term is used herein. Exemplary aryl group substituents for R$^a$-R$^d$ and R$^{a'}$-R$^{d'}$ include, H, substituted or unsubstituted alkyl, substituted or unsubstituted heteroalkyl, substituted or unsubstituted aryl, substituted or unsubstituted heteroaryl, halogen, CN, CF$_3$, acyl, —SO$_2$NR$^8$R$^9$, —NR$^8$R$^9$, —OR$^8$, —S(O)$_2$R$^8$, —C(O)R$^9$, —COOR$^8$, —CONR$^8$R$^9$, —S(O)$_2$OR$^8$, —OC(O)R$^8$, —C(O)NR$^8$R$^9$, —NR$^8$C(O)R$^9$, —NR$^8$SO$_2$R$^9$ and —NO$_2$, wherein two or more of R$^a$, R$^b$, R$^c$, R$^d$, R$^{a'}$, R$^{b'}$, R$^{c'}$, R$^{d'}$, together with the atoms to which they are bonded, are optionally joined to form a ring system which is a member selected from substituted or unsubstituted cycloalkyl, substituted or unsubstituted heterocycloalkyl, substituted or unsubstituted aryl and substituted or unsubstituted heteroaryl.

Exemplary moieties for R$^8$ and R$^9$ include members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, and R$^8$ and R$^9$, together with the atoms to which they are bonded, are optionally joined to form a 5- to 7-membered ring selected from substituted or unsubstituted cycloalkyl, substituted or unsubstituted heterocycloalkyl, substituted or unsubstituted aryl, and substituted or unsubstituted heteroaryl.

In various embodiments, the chiral anion has the formula:

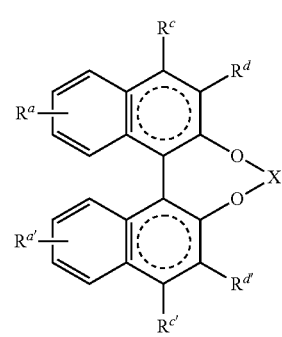

in which each of the "R" moieties on the aryl rings are independently selected from those moieties set forth above for R$^a$, R$^b$, R$^c$, R$^d$, R$^{a'}$, R$^{b'}$, R$^{c'}$, R$^{d'}$.

In various embodiments, the chiral anion in a compound of the invention is:

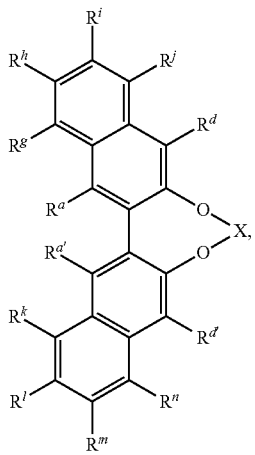

in which each of the "R" moieties on the aryl rings are independently selected from those moieties set forth above for $R^a$, $R^b$, $R^c$, $R^d$, $R^{a'}$, $R^{b'}$, $R^{c'}$, $R^{d'}$.

In various embodiments, the chiral anion in a compound of the invention is:

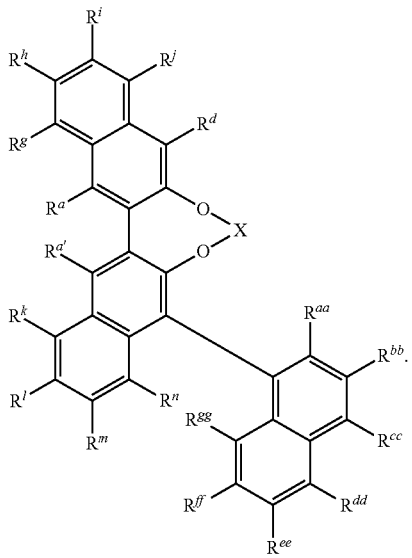

in which each of the "R" moieties on the aryl rings are independently selected from those moieties set forth above for $R^a$, $R^b$, $R^c$, $R^d$, $R^{a'}$, $R^{b'}$, $R^{c'}$, $R^{d'}$.

In an exemplary embodiment, the chiral anion in a compound of the invention is:

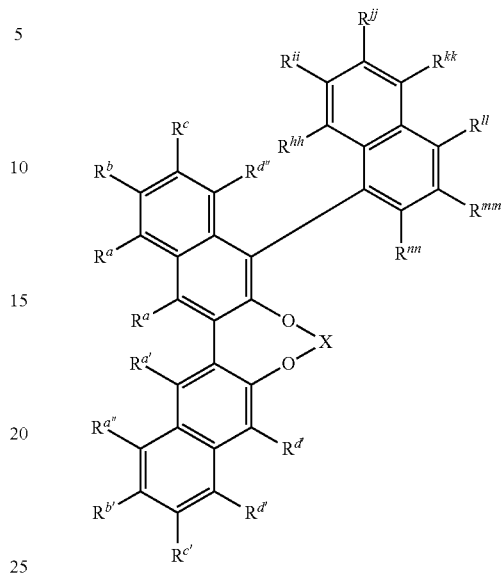

in which each of the "R" moieties on the aryl rings are independently selected from those moieties set forth above for $R^a$, $R^b$, $R^c$, $R^d$, $R^{a'}$, $R^{b'}$, $R^{c'}$, $R^{d'}$.

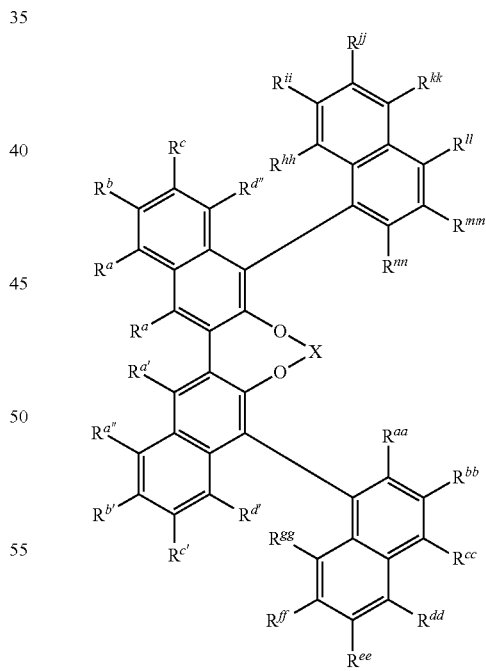

in which each of the "R" moieties on the aryl rings are independently selected from those moieties set forth above for $R^a$, $R^b$, $R^c$, $R^d$, $R^{a'}$, $R^{b'}$, $R^{c'}$, $R^{d'}$.

In an exemplary embodiment, the anion in the compound of the invention has the formula:

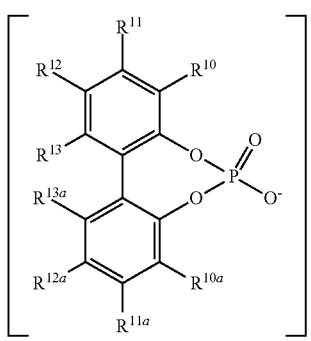

wherein $R^{10}$, $R^{10a}$, $R^{11}$, $R^{11a}$, $R^{12}$, $R^{12a}$, $R^{13}$, $R^{13a}$ are independently members selected from "aryl group substituents" as this term is used herein. Exemplary aryl group substituents include, H, substituted or unsubstituted alkyl, substituted or unsubstituted heteroalkyl, substituted or unsubstituted aryl, substituted or unsubstituted heteroaryl, halogen, CN, $CF_3$, acyl, $-SO_2NR^8R^9$, $-NR^8R^9$, $-OR^8$, $-S(O)_2R^8$, $-C(O)R^9$, $-COOR^8$, $-CONR^8R^9$, $-S(O)_2OR^8$, $-OC(O)R^8$, $-C(O)NR^8R^9$, $-NR^8C(O)R^9$, $-NR^8SO_2R^9$ and $-NO_2$, wherein two or more of $R^{10}$, $R^{10a}$, $R^{11}$, $R^{11a}$, $R^{12}$, $R^{12a}$, $R^{13}$, $R^{13a}$, together with the atoms to which they are bonded, are optionally joined to form a ring system which is a member selected from substituted or unsubstituted cycloalkyl, substituted or unsubstituted heterocycloalkyl, substituted or unsubstituted aryl and substituted or unsubstituted heteroaryl.

$R^8$ and $R^9$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, and $R^8$ and $R^9$, together with the atoms to which they are bonded, are optionally joined to form a 5- to 7-membered ring which is a member selected from substituted or unsubstituted cycloalkyl, substituted or unsubstituted heterocycloalkyl, substituted or unsubstituted aryl and substituted or unsubstituted heteroaryl.

Exemplary anions of use in the compounds of the invention are soluble in non-polar media, e.g., hexanes. By "soluble", as used herein, is meant a degree of solubility that, when the anion combines with the cation, there is produced a catalytically active concentration of the resulting compound of the invention.

The cations in compounds of the invention can be any cation capable of transferring a desired species to an electrophilic center. In various embodiments, the invention is illustrated by reference to a cation that transfers a positive halogen or positive aryl species. Exemplary cations of use in the compounds of the invention are essentially insoluble in non-polar media, e.g., hexanes. By "insoluble", as used herein, is meant a degree of solubility that, when the anion combines with the cation, there is not produced a catalytically active concentration of the resulting compound of the invention.

In an exemplary embodiment, the chiral ion pair is a catalyst for the fluorocylization of an alkene. Fluorocylizations, wherein a pendant nucleophile attacks a π-bond activated by an electrophilic fluorine source, are much less common than the analogous reactions of heavier halogens (S. C. Wilkinson, R. Salmon, V. Gouverneur, Developments in fluorocyclization methodologies, *Future Med. Chem.* 1, 847 (2009)), and enantioselective variants are almost unknown (O. Lozano, G. Blessley, T. Martinez del Campo, A. L. Thompson, G. T. Giuffredi, M. Bettati, M. Walker, R. Borman, V. Gouverneur, Organocatalyzed enantioselective fluorocyclizations, *Angew. Chem. Int. Ed.* 50, 8105 (2011)).

In an exemplary embodiment, the cation is derived from Selectfluor 1 (FIG. 1), a versatile cationic fluorinating agent that is normally be insoluble in nonpolar media.

An unanticipated benefit of the phase-transfer protocol is an improved tolerance toward sensitive functionality. When treated with Selectfluor under homogeneous conditions, benzothiophene substrates 10a and 10b were converted to a complex mixture of products with only trace conversion to desired product (FIG. 3C). However, when the chiral anion-mediated phase-transfer reaction conditions were applied, fluorocyclization products 11a and 11b were isolated in good yield and high optical purity. This improved chemoselectivity may be due to a combination of the slow introduction of the fluorinating agent into solution and possibly a reduction in reactivity in nonpolar solvent. This result is in contrast to a recent report from Lectka and coworkers, wherein increased reactivity of Selectfluor was observed through a postulated counterion exchange in acetonitrile (S. Bloom, M. T. Scerba, J. Erb, T. Lectka, Tricomponent catalytic α,α-difluorination of acid chlorides, *Org. Lett.* 13, 5068 (2011)).

This cation was combined with a lipophilic, bulky chiral phosphate anion, e.g., 2 (FIG. 1) and exchanged with one or both of the tetrafluoroborate anions associated with Selectfluor to bring the reagent into solution. The resulting chiral ion pair could then mediate an asymmetric fluorination of an organic substrate in solution. Given its insolubility, no significant background reaction between Selectfluor and substrate was observed.

Thus, in an exemplary embodiment, the cation is Selectfluor and has the formula:

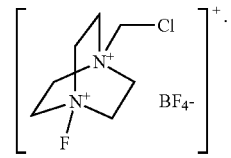

In various embodiments, the cation is the bromo analog of the formula set forth above.

IV. The Methods

The present invention also provides methods of preparing the chiral ion pairs of the invention. Thus, in an exemplary embodiment, the invention provides a method of preparing the chiral ion pair comprising contacting the cation and the anion under conditions appropriate to form the ion pair catalyst of the invention.

In an exemplary embodiment, the method of preparing the catalyst of the invention includes:

contacting a solution of:

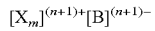

in a non-polar organic solvent with:

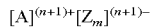

under conditions appropriate to form the ion pair.

In the formulae above, X is a metallic or non-metallic cation. Z is a metallic or non-metallic anion. A is the cationic donor. B is the chiral anion. The index m is selected from 1, 2 and 3; and the index n is selected from 0, 1 and 2. In an exemplary embodiment, the cationic is a source of $Ar^+$, $F^+$ or a source of $Br^+$.

The present anion-based phase-transfer procedure is appealing because it avoids the use of transition metals and the need to rigorously exclude air and moisture. More importantly, it offers a mechanism for robust catalyst turnover and suppression of the racemic background reaction. This makes it particularly advantageous for transformations like halocyclizations where nucleophilic catalysis and other existing methods have often suffered from insufficient rate acceleration over the background reactivity. The highly enantioselective fluorocyclizations provided by the present invention exemplify the catalysts and methods of the invention. In an exemplary embodiment, the method generates heterocyclic products with two stereogenic centers, including a carbon-halogen (e.g., C—F) stereocenter that would be very difficult to construct using alternative approaches. Furthermore, the reactivity of the present system allows less electron-rich olefins to be fluorinated relative to previous reports. The enhanced reactivity fortunately does not trade off with the stereoselectivity, which compares favorably with other chiral electrophile-based fluorination methods.

The chiral anion phase-transfer catalysis scheme can be superimposed on any number of transformations involving cationic reagents or reaction intermediates. Its successful application to electrophilic asymmetric fluorination, which very few catalyst systems have achieved with consistently high enantioselectivities, suggests that it may find utility in other areas of chemistry as well. The invention provides for the transformation of substrates of diverse structures. In exemplary embodiments, the invention provides methods for the asymmetric fluorocyclization and bromocyclization of benzamides (e.g., dihydropyran-derived benzamides), alpha fluorination of enamines, alkoxy- and hydroxyl bromination and fluorination of alkenes, fluoro- and bromo-cyclization of dienyl substrates, fluoro- and bromo-ene reaction of styryl substrates, ring expansion of vinyl substituted ring systems (e.g., cyclic alcohols, e.g., cyclopropanols, cyclobutanols), and aminofluorination and aminobromination of dienyl substrates, for example. In each of these embodiments, the method includes contacting the desired substrate with a catalyst of the invention under conditions appropriate to effect the desired transformation. Exemplary conditions are set forth in the Examples appended hereto.

In an exemplary embodiment there is provided a method of cyclizing an alkene. The method includes contacting an alkene having the formula:

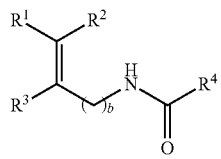

with a chiral ion pair according to the invention under conditions appropriate to cyclize the alkene. In the formula above, n is selected from 1 and 2. $R^1$, $R^2$ and $R^3$ are members independently selected from "alkyl group substituents" as this term is used herein, e.g., H, substituted or unsubstituted alkyl, substituted or unsubstituted heteroalkyl, substituted or unsubstituted aryl and substituted or unsubstituted heteroaryl, and a member selected from $R^1$ and $R^2$, $R^2$ and $R^3$, and $R^1$, $R^2$ and $R^3$, together with the atoms to which they are attached are optionally joined to form a ring system, which is a member selected from substituted or unsubstituted cycloalkyl, substituted or unsubstituted heterocycloalkyl, substituted or unsubstituted aryl and substituted or unsubstituted heteroaryl; and $R^4$ is a member selected from substituted or unsubstituted aryl and substituted or unsubstituted heteroaryl. The index b is 1, 2, 3, 4, or 5.

In various embodiments, the cyclization of said alkene yields a product having the formula:

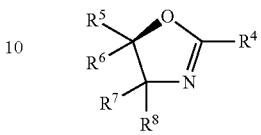

wherein $R^5$ and $R^6$, together with the atoms to which they are attached, are optionally joined to form a ring system which is a member selected from substituted or unsubstituted aryl, substituted or unsubstituted heteroaryl, substituted or unsubstituted cycloalkyl, and substituted or unsubstituted heterocycloalkyl, wherein said ring system is substituted with at least one member selected from halogen and substituted or unsubstituted aryl. $R^7$ and $R^8$ are members independently selected from H, substituted or unsubstituted alkyl and substituted or unsubstituted heteroalkyl.

In an exemplary embodiment, $R^5$ and $R^6$ in the formula above are joined to form a ring system having the formula:

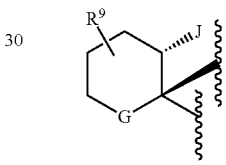

wherein J is a member selected from halogen and substituted or unsubstituted aryl. G is a member selected from O, and S. $R^9$ is a member selected from H, substituted or unsubstituted alkyl, substituted or unsubstituted heteroalkyl, substituted or unsubstituted aryl and substituted or unsubstituted heteroaryl, and when more than one $R^9$ is present, each $R^9$ is independently selected, and two or more $R^9$ moieties, together with the atoms to which they are attached, are optionally joined to form a ring system.

In various embodiments, the cyclization product has the formula:

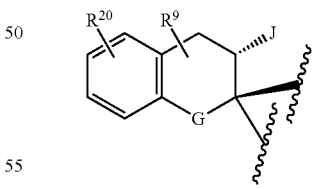

wherein $R^{20}$ is a member selected from H, substituted or unsubstituted alkyl, substituted or unsubstituted heteroalkyl, substituted or unsubstituted aryl, substituted or unsubstituted heteroaryl, halogen, CN, $CF_3$, acyl, $-SO_2NR^{18}R^{19}$, $-NR^{18}R^{19}$, $-OR^{18}$, $S(O)_2R^{18}$, $-C(O)R^{18}$, $-COOR^{18}$, $-CONR^{18}R^{19}$, $-S(O)_2OR^{18}$, $-OC(O)R^{18}$, $-C(O)NR^{18}R^{19}$, $-NR^{18}C(O)R^{19}$, $NR^{18}SO_2R^{19}$ and $-NO_2$, wherein $R^{18}$ and $R^{19}$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, and $R^{18}$ and $R^{19}$, together with the atoms to which they are bonded, are optionally joined to form a 5- to 7-membered ring, e.g., substituted or unsubstituted cycloalkyl, substituted or unsubstituted heterocycloalkyl, substituted or unsubstituted aryl and substituted or unsubstituted heteroaryl. When more than one $R^{20}$ is present, each $R^{20}$ is independently selected. J is the added electrophilic moiety.

In an exemplary embodiment, G is O. In various embodiments, J is F. In various embodiments, each $R^9$ is H.

In various embodiments, the product is produced stereoselectively. For example, in some embodiments, the product is produced with an ee of at least about 80%, at least about 85%, at least about 90%, at least about 95% or at least about 99% enantiomeric excess.

The inclusion of Proton Sponge (1,8-bis(dimethylamino)naphthalene) as a base served a dual purpose of generating the anionic phosphate catalyst in situ from its conjugate acid 2b as well as neutralizing the equivalent of acid generated during the reaction. Thus, in various embodiments, the method further includes the addition of a base, e.g., Proton Sponge, to the reaction mixture.

In various embodiments, the methods of the invention provide for the efficient fluorocyclization of dihydronaphthalene and chromene substrates (FIG. 3A). Excellent enantioselectivities were obtained even at room temperature (92 to 96% ee), although in this case a slightly higher catalyst loading gave optimal results.

The method of the invention also provides for the fluorination of an unactivated alkene, e.g., with only alkyl substituents, in good yield of fluorinated product (FIG. 3B). Fluorination of these less reactive substrates was accomplished most effectively using inorganic bases such as sodium carbonate. Thus, the methods of the invention include, in exemplary embodiments, the inclusion in the reaction mixture of one or more organic or inorganic base, e.g., $Na_2CO_3$.

The steric properties of the anion can be used to adjust the reactivity and enantioselectivity of the catalyst in the methods of the invention. For example, the hydrophobic alkyl chains attached to the backbone of the catalyst proved beneficial: use of the unsubstituted catalyst (2c) reduced the enantioselectivity to 87%.

The methods of the invention are of use with a broad range of substrate structures and substitution patterns, e.g., on the benzamide ring. Products with a variety of substituents on the benzamide ring including halides, nitro and alkyl groups were obtained in very good yields with enantioselectivities above 95% (products 4b-f). Substitutions at the 2- or 3-positions of the aryl ring gave rise to slightly more variability in terms of yield and stereoselectivity but were generally well tolerated (4g-i). The absolute stereochemistry of product 4c as shown in FIG. 2 was determined by single-crystal X-ray diffraction (see supporting online material for crystallographic data), and all other products were assigned by analogy.

In another exemplary embodiment, the invention provides a method of adding an electrophile to the alpha position of an enamine. In an exemplary embodiment, the substrate has the formula:

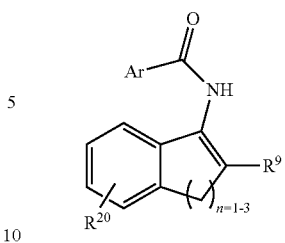

in which $R^9$ and $R^{20}$ are as discussed above, and Ar is substituted or unsubstituted aryl or substituted or unsubstituted heteroaryl. An exemplary method of the invention performed on the substrate above, produces an enantiomerically enriched product having the formula:

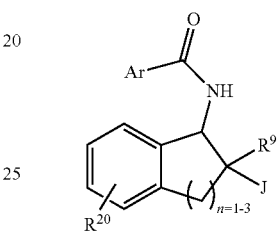

in which J is added electrophilic group, e.g., F, Cl, Br, I, or Ar. Those of skill will appreciate that the benzoyl amine protecting group is merely exemplary and the method of the invention is applicable to a broad class of enamines and is not limited to N-benzoyl enamines.

In yet another embodiment, the invention provides a method of fluorocyclizing a dienyl substrate. The method includes contacting the dienyl substrate under conditions appropriate to effect the fluorocyclization. In an exemplary embodiment, the two double bonds are situated in the substrate such that the fluorocyclization provides a product having a new ring system having 4-, 5, 6-, 7- or 8-members. The ring optionally contains or or more heteroatom.

Figure 8:
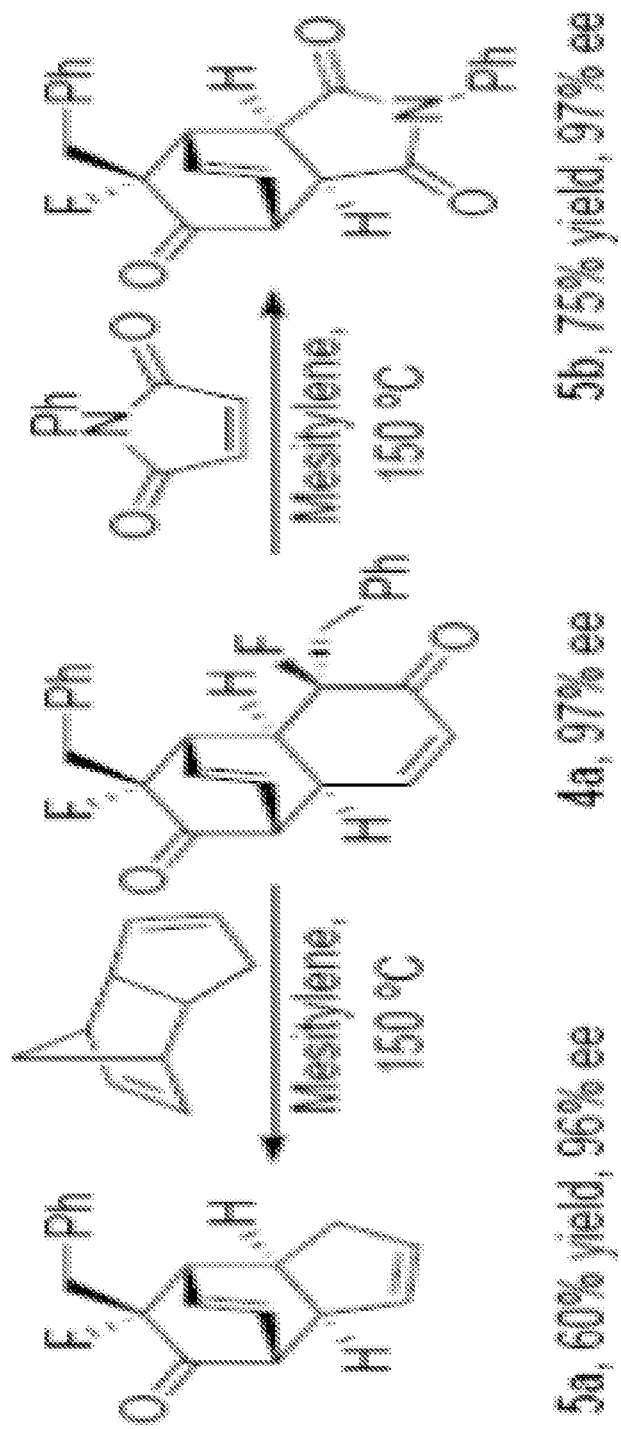
FIG. 8 shows an example of products formed by a retro [4+2]/[4+2] reaction.
Figure 9A:
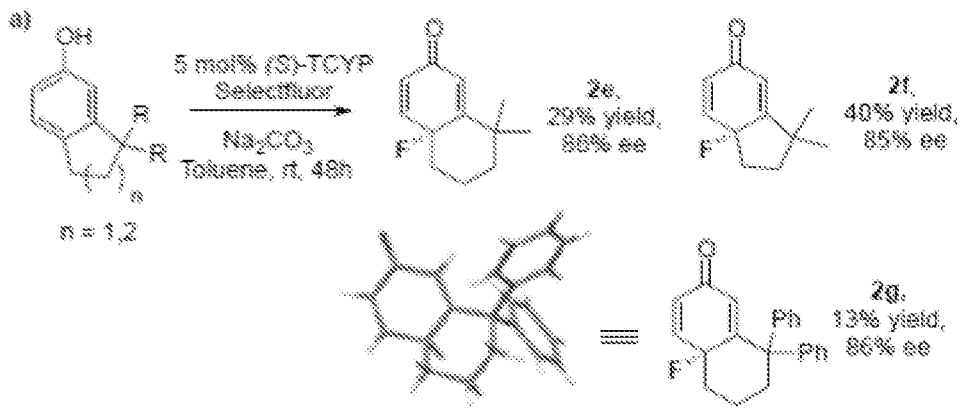
FIG. 9 shows exemplary reaction motifs available using the catalysts and method of the invention: (A) Para-selective fluorinative dearomatization; (B) Predictable selectivity based on sterics of phenol; (C) Asymmetric synthesis of fluoro-analogue of Grandifloracin.
Figure 9B:
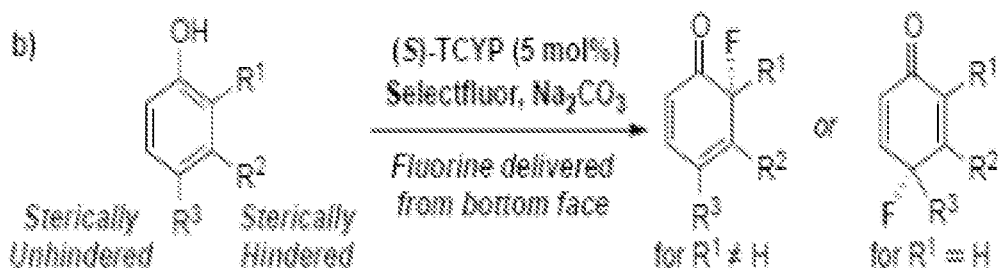
Figure 9C:
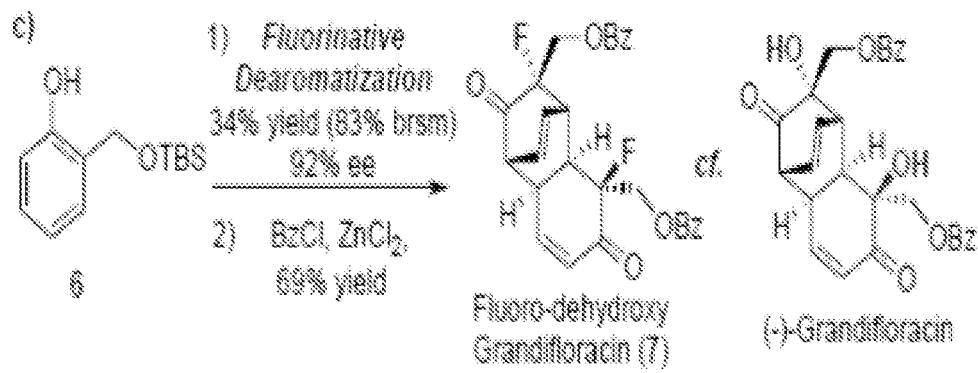
Figure 10:
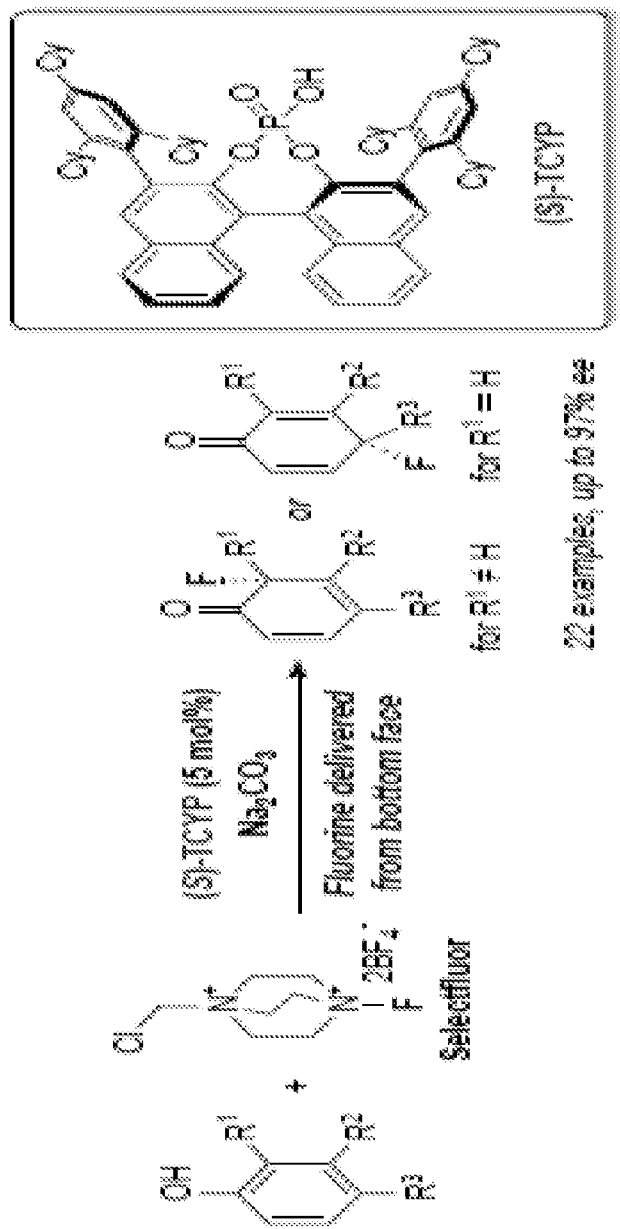
FIG. 10 is an exemplary reaction scheme according to the methods of the invention.
Figure 11:
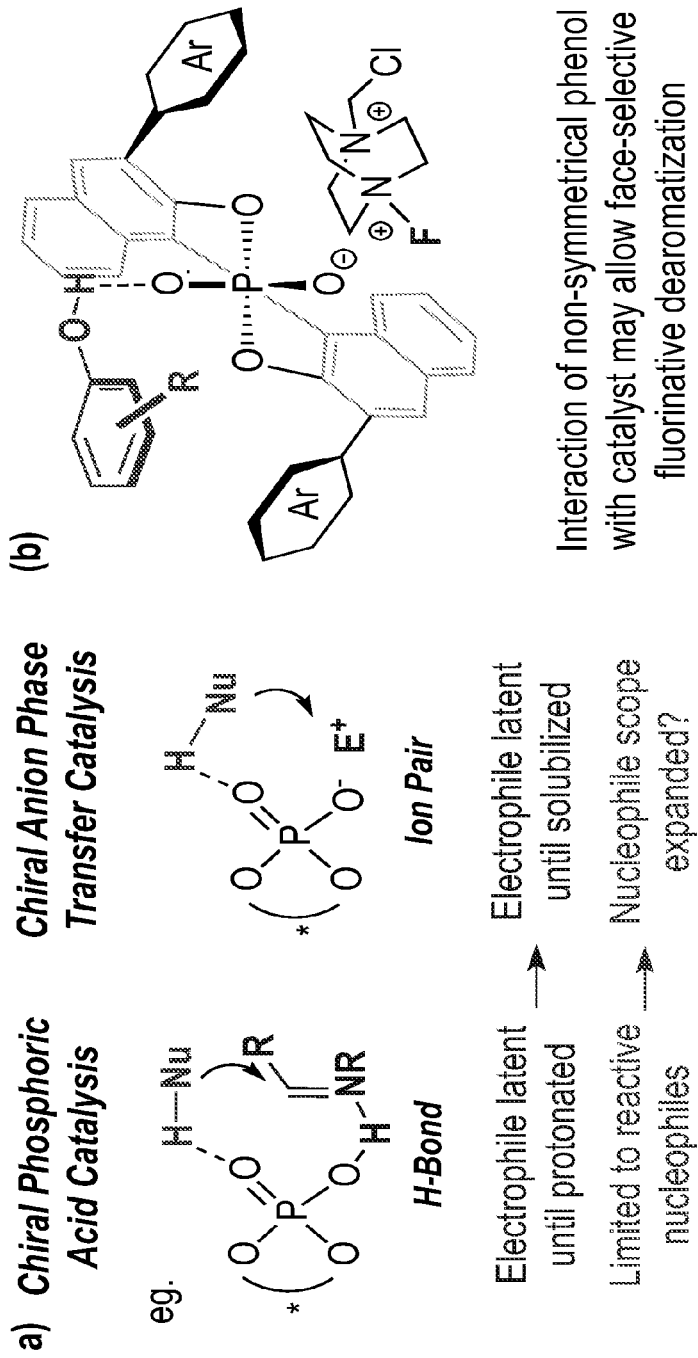
FIG. 11 is a graphic showing: (A) an exemplary difference between the method of the invention and prior methods; and (B) a working hypothesis for a reaction intermediate for fluorinative dearomatization of a phenol.

In a still further exemplary embodiment, the invention provides a method of dearomatizing an aromatic substrate using a catalyst of the invention. The method includes contacting an aromatic substrate with a catalyst of the invention under conditions appropriate to add the electrophilic moiety to an atom of the aromatic system, thereby disrupting the aromatic system. In an exemplary embodiment, the substrate is a substituted or unsubstituted phenol. Exemplary reaction motifs accessible using the method and catalyst of the invention include, without limitation, addition of the electrophilic moiety to the position ortho or para to the hydroxyl moiety of a phenol (FIG. 5-6); addition of the electrophilic moiety to the position ortho to the hydroxyl of a phenol coupled with [4+2] dimerization (FIG. 7); and addition of the electrophilic moiety to a position ortho to the hydroxyl of a phenol coupled with retro [4+2]/[4+2] addition (FIG. 8). The methods of the invention provide predicable selectivity of electrophile addition based on the steric properties of the phenol (FIG. 9). The predictable selectivity of electrophile addition allows the method of the invention to be incorporated into the synthesis of complex molecules, e.g., grandifloricin.

In an exemplary embodiment, the phenol substrate is selected from:

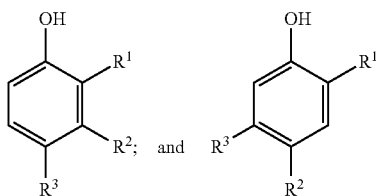

in which $R^1$, $R^2$ and $R^3$ are independently selected from "aryl group substituents" as that term is defined herein. One or more member selected from $R^1$ and $R^2$; and $R^2$ and $R^3$, together with the atoms to which they are bound are optionally joined to form a ring structure selected from substituted or unsubstituted alkyl, substituted or unsubstituted heteroalkyl, substituted or unsubstituted aryl and substituted or unsubstituted heteroaryl.

The following examples illustrate embodiments of the invention and are not intended to limit the scope of the catalysts of the invention or the methods in which they find use.

EXAMPLES

Example 1

Compound numbers in Examples 1-12 correspond to the numbering in FIG. 1-4.

1.1 General Information. Unless otherwise noted, all commercial reagents were used without further purification. Selecfluor® (Sigma Aldrich) was dried with heating under high vacuum for 15 minutes prior to use. Small scale reactions were run in 25 mm test tubes fitted with a rubber septum. Dichloromethane, toluene, ether, toluene and triethylamine were purified by passage through an activated alumina column under argon. Thin-layer chromatography analysis of reaction mixtures was performed using Merck silica gel 60 F254 TLC plates, and visualized under UV or by staining with ceric ammonium molybdate or $KMnO_4$. Flash column chromatography was carried out on Merck Silica Gel 60 Å, 230 X 400 mesh. Nuclear magnetic resonance (NMR) spectra were recorded using Bruker DRX-500, AVQ-400 and AV-300 spectrometers. $^1H$ and $^{13}C$ chemical shifts are reported in ppm downfield of tetramethylsilane and referenced to residual solvent peak ($CHCl_3$; $\delta_H$=7.26 and $\delta_C$=77.0, $CH_3OH$; $\delta_H$=3.31 and $\delta_H$=49.2). Multiplicities are reported using the following abbreviations: s=singlet, d=doublet, t=triplet, q=quartet, m=multiplet, br=broad resonance. Diastereomeric ratios were determined by integration of $^{19}F$ NMR spectra of crude product prior to purification. Mass spectral data were obtained from the Micro-Mass/Analytical Facility operated by the College of Chemistry, University of California, Berkeley. Enantiomeric excesses were determined on a Shimadzu VP Series Chiral HPLC. The synthesis of phosphoric acid 9 has been previously described by us.[1]

[1] Rauniyar, V.; Wang, J. Z.; Burks, H.; Toste, F. D. *J. Am. Chem. Soc.* 2011, 133, 8486-8489.

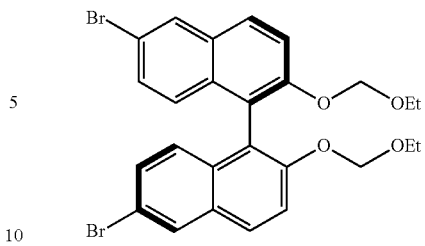

1.2 (R,R)-6,6'-dibromo-2,2'-bis(ethoxymethoxy)-1,1'-binaphthalene (S2b-1): To a suspension of NaH (60 wt %, 2.5 equiv, 50 mmol) in THF 100 mL at 0° C. was added a solution of (R)-6,6'-dibromo-[1,1'-binaphthalene]-2,2'-diol[2] (20 mmol) in THF 20 mL. The resulting solution was stirred for 1 h at 0° C. and after the elapsed time, EOM-Cl (60 mmol) was added in one portion. The resulting solution was stirred for 1 h while gradually warming the reaction temperature to ambient. After the elapsed time, water was carefully added and the reaction mixture was extracted with EtOAc and washed with brine and dried over anhydrous $MgSO_4$, filtered and concentrated in vacuo. The crude material was dissolved in minimal amount of $CH_2Cl_2$ and precipitated by addition of MeOH. The precipitate was filtered and dried under high vacuum for 1 h to afford the title compound in 16.6 mmol (83% yield as a white crystalline powder). $^1H$-NMR (400 MHz, $CDCl_3$) δ (ppm) 8.04 (d, J=2 Hz, 2H), 7.86 (d, J=9.2 Hz, 2H), 7.64 (d, J=9.2 Hz, 2H), 7.30 (dd, J=2.0, 9.2 Hz, 2H), 7.00 (d, J=9.2 Hz, 2H), 5.14 (d, J=7.2 Hz, 2H), 5.04 (d, J=7.2 Hz, 2H), 3.47-3.35 (m, 4H), 1.06 (t, J=7.2 Hz, 6H); $^{13}C$-NMR δ (100.6 MHz, $CDCl_3$) δ (ppm) 153.1, 132.3, 130.7, 129.8, 129.6, 128.6, 127.1, 120.5, 118.1, 117.8, 93.6, 64.1, 14.9; HRMS Calcd. For $C_{26}H_{24}{}^{79}Br_2O_4Na$: 580.9934; found: 580.9947.

[2] Rueping, M.; Sugiono, E.; Steck, A.; Theissmann, T. *Adv. Synth. Catal.* 2010, 352 (2+3), 281-287.

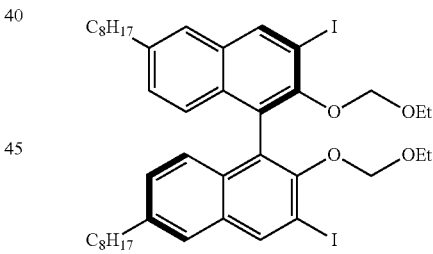

1.2 (R,R)-2,2'-bis(ethoxymethoxy)-3,3'-diiodo-6,6'-dioctyl-1,1'-binaphthalene (S2b-2): Into a flame-dried 3-neck round bottom flask equipped with a magnetic stir bar and a reflux condenser was added $NiCl_2$(dppp) 540 mg (10 mol %) and (R)-6,6'-dibromo-2,2'-bis(ethoxymethoxy)-1,1'-binaphthalene (5.56 g, 1.0 equiv). The flask was evacuated and purged with nitrogen. Anhydrous $Et_2O$ (35 ml) was added and the reaction mixture was cooled to 0° C. To the suspension was drop-wise added n-Octylmagnesium bromide (24.8 mL, 2.0 M in $Et_2O$, 5.0 equiv) over the course of 10 min. The reaction mixture was gradually warmed to room temperature and stirred for 30 min, upon which TLC indicated complete consumption of the starting material. The reaction mixture was carefully poured over frozen 1N HCl (50 mL) and the mixture was extracted with $Et_2O$. The combined organic extracts were dried over anhydrous magnesium sulfate and filtered through a small pad of silica. The filtrate was concentrated in vacuo and transferred to a flame dried 500 mL flask equipped with a magnetic stir bar. To the crude product was added anhydrous THF (100 mL) and the solution was cooled to −78° C. After 10 min, n-BuLi (14.0 mL, 2.5 M in hexanes, 3.5 equiv) was added drop-wise over 10 min. The solution was kept at −78° C. for 30 min and then warmed to 0° C. and stirred for 1.5 h at this temperature upon which fine light-brown precipitate was observed. After the elapsed time the reaction mixture was cooled to −78° C. and iodine 9.48 g (3.75 equiv) was added in one portion. The reaction mixture was stirred for 10 min and then warmed to room temperature over 40 min. The reaction mixture was quenched with satd. $Na_2SO_3$ and extracted with EtOAc. The organic layer was washed with water and brine and dried over anhydrous $MgSO_4$, filtered and concentrated in vacuo. The residue was subjected to purification by flash chromatography (0-10% $Et_2O$ gradient) to obtain the desired product 6.54 g (75% overall yield). $^1$H-NMR (400 MHz, $CDCl_3$) δ (ppm) 8.45 (s, 2H), 7.53 (s, 2H), 7.14 (d, J=8.8 Hz, 2H), 7.08 (d, J=8.4 Hz, 2H), 4.86 (d, J=5.6 Hz, 2H), 4.70 (d, J=5.6 Hz, 2H), 3.03-3.10 (m, 2H), 2.71 (t, J=7.6 Hz, 4H), 2.69-2.62 (m, 2H), 1.63 (q, J=6.8 Hz, 4H), 1.44-1.25 (m, 20H), 0.87 (t, J=6.4 Hz, 6H), 0.65 (d, J=7.2 Hz, 6H). $^{13}$C-NMR δ (ppm) 151.4, 140.5, 139.3, 132.4, 132.1, 128.8, 126.3, 126.0, 125.1, 98.0, 92.4, 69.9, 35.8, 31.8, 31.1, 29.4, 29.3, 29.2, 22.6, 14.4, 14.1). HMRS Calcd. For $C_{42}H_{56}O_4{}^{127}I_2Na$: 901.2160; found 901.2172.

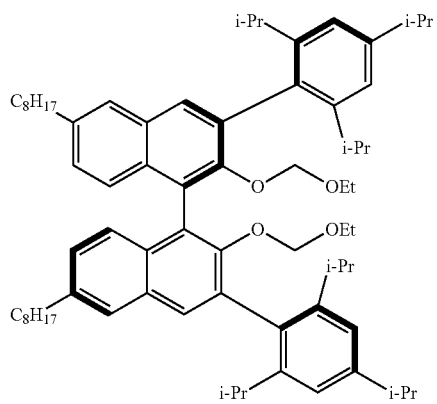

1.3 (R,R)-2,2'-bis(ethoxymethoxy)-6,6'-dioctyl-3,3'-bis(2,4,6-triisopropylphenyl)-1,1'-binaphthalene (S2b-3): Into a flame-dried 3-neck round-bottom flask equipped with a reflux condenser and a magnetic stir bar was charged magnesium metal (496 mg, 20.4 mmol) and a small crystal of iodine. THF 1 ml was added and the mixture was heated until the color of iodine disappeared. To thus activated magnesium was added 1,3,5-triisopropylbromobenzene 5.5 g (19.4 mmol) in THF 25 mL. The resulting mixture was heated at reflux for 3 h and cooled to room temperature. On the side, into a flame dried round bottom flask equipped with a stir bar was charged (R)-2,2'-bis(ethoxymethoxy)-3,3'-diiodo-6,6'-dioctyl-1,1'-binaphthalene 2.84 g (3.24 mmol) and $NiCl_2(PPh_3)_2$ 211 mg (0.32 mmol) and the mixture was suspended in anhydrous $Et_2O$ (10 mL). To the solution at room temperature was added drop-wise the Grignard prepared above. The reaction mixture was stirred for 45 min and carefully poured over ice-cold 1N HCl. The mixture was extracted with $CH_2Cl_2$ and washed with brine and dried over anhydrous $MgSO_4$, filtered and concentrated in vacuo. The product was purified by flash chromatography (0-20% $CH_2Cl_2$/hexanes) to afford 1.83 g of the desired product (55% yield). $^1$H-NMR (300 MHz, $CDCl_3$) δ (ppm) 7.72 (s, 2H), 7.67 (s, 2H), 7.39 (d, J=8.7 Hz, 2 H), 7.22 (dd, J=1.5, 8.4 Hz, 2H), 7.18-7.14 (m, 4H), 4.32 (d, J=5.1 Hz, 2H), 4.29 (d, J=5.1 Hz, 2H), 3.08-2.87 (m, 6H), 2.80 (apt, J=7.5 Hz, 4H), 2.61-2.42 (m, 4H), 1.83-1.72 (m, 4H), 1.38-1.21 (m, 44H), 1.05 (d, J=6.6 Hz, 6H), 0.96-0.92 (m, 6H), 0.56 (t, J=7.2 Hz, 6H);). $^{13}$C NMR (75.5 MHz, $CDCl_3$) δ (ppm) 151.7, 148.1, 147.6, 146.7, 140.7, 134.2, 133.5, 133.3, 132.1, 130.5, 130.3, 127.7, 126.1, 125.9, 121.3, 120.7, 120.4, 96.4, 63.5, 36.0, 34.4, 31.9, 31.4, 30.9, 30.8, 29.6, 29.5, 29.3, 26.0, 25.2, 24.1, 23.3, 23.2, 22.7, 14.5, 14.1; HRMS Calcd. for $C_{72}H_{102}O_4Na$: 1053.7670, found: 1053.7690.

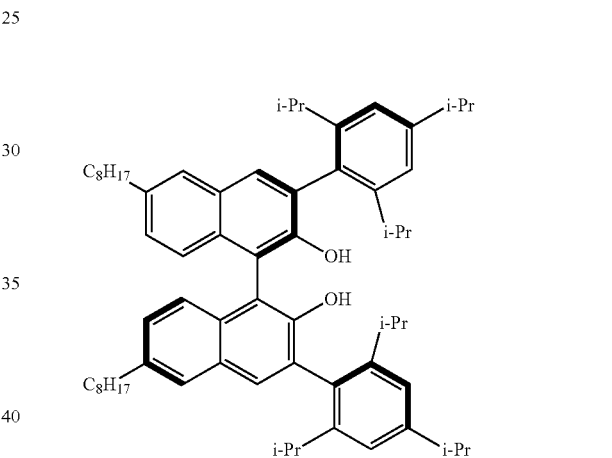

1.4 (R,R)-6,6'-dioctyl-3,3'-bis(2,4,6-triisopropylphenyl)-[1,1'-binaphthalene]-2,2'-diol (S2b-4): 1.5 g was dissolved in Dioxane 50 mL. Conc HCl (5 mL) was added and the solution was heated to 70° C. and stirred at this temperature for 1 h upon which TLC indicated complete consumption of the acetal. The solvent was evaporated in vacuo, and the residue was dissolved in $CH_2Cl_2$ and washed with Satd. $NaHCO_3$ and then water and then brine. The organic layer was then dried over anhydrous $MgSO_4$ and filtered and concentrated in vacuo. The residue was purified by flash chromatography ($CH_2Cl_2$/hexane 0-20% gradient) to obtain 968 mg of the bisphenol adduct in 72% yield. $^1$H-NMR (300 MHz, $CDCl_3$) δ (ppm) 7.78 (s, 2H), 7.72 (s, 2H), 7.33-7.21 (m, 8H), 4.96 (s, 2H), 3.10-2.92 (m, 4H), 2.85-2.75 (m, 6H), 1.99-1.77 (m, 4H), 1.42-1.04 (m, 56H), 0.96-0.94 (m, 6H); $^{13}$C-NMR (75.5 MHz, $CDCl_3$) δ (ppm) 150.0, 148.9, 147.7, 147.6, 138.4, 131.8, 130.8, 130.2, 129.2, 128.9, 128.2, 126.6, 124.5, 121.1, 112.9, 36.0, 34.3, 31.9, 31.5, 30.8, 29.6, 29.5, 29.3, 25.3, 24.34, 24.3, 24.1, 24.0, 23.9, 23.7, 22.7, 12.1; HRMS Calcd. for: [M−H] $C_{66}H_{89}O_2$: 913.6868, found: 913.6857.

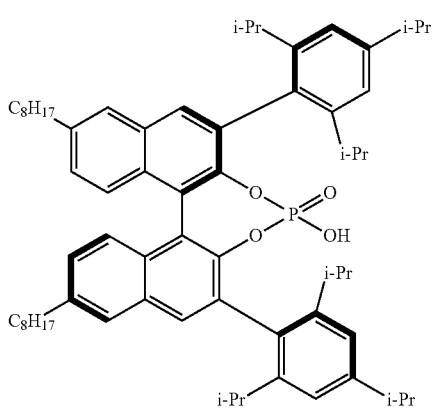

1.5 (R,R)-4-hydroxy-9,14-dioctyl-2,6-bis(2,4,6-triisopropylphenyl)dinaphtho[2,1-d:1',2'-f][1,3,2]dioxaphosphepine 4-oxide (2b): Bisphenol S2b-4, 968 mg (1.06 mmol) was suspended in anhydrous pyridine 3 mL and to the mixture was added POCl$_3$ (194 μL, 2.12 mmol). The resultant was heated at 95° C. for 16 h. The resulting solution was cooled to rt and water 3 mL was added. This mixture was then heated at 105° C. for 5 h and then cooled to rt. The reaction mixture was diluted with CH$_2$Cl$_2$ and washed three times with 3N HCl and then dried over anhydrous MgSO$_4$, filtered and concentrated in vacuo. The crude material was purified by flash chromatography (0-5% MeOH/CH$_2$Cl$_2$). The fractions containing the desired product were combined and the solvent evaporated. The residue was then dissolved in anhydrous Et$_2$O and treated with anhydrous HCl (5 mL, 2.0 M in Et$_2$O) and stirred at room temperature for 30 min. The resulting ethereal solution was filtered through celite and the solvent evaporated in vacuo, and the residue was dried until a constant mass of 931 mg (90% yield). $^1$H-NMR (400 MHz, CDCl$_3$) δ (ppm) 7.71 (s, 2H), 7.63 (s, 2H), 7.25 (d, J=8.8 Hz, 2H), 7.20 (d, J=8.0 Hz, 2H), 2.88-2.76 (m, 6H), 2.58 (sept, J=6.8 Hz, 2 H), 2.52 (sept, J=6.8 Hz, 2 H), 1.77-1.69 (m, 4H), 1.45-1.30 (m, 20 H), 1.23 (dd, J=6.8, 0.8 Hz, 12H), 1.05-0.96 (m, 12H), 0.91-0.88 (m, 12 H), 0.50 (d, J=6 Hz, 6H); $^{13}$C-NMR δ (100.6 MHz, CDCl$_3$) δ (ppm) 148.1, 147.6, 147.0, 145.4, 145.3, 140.3, 132.3, 132.3, 131.1, 130.7, 127.5, 127.5, 126.4, 121.8, 121.2, 120.2, 36.1, 36.0, 34.7. 34.1, 32.0, 31.7, 31.4, 31.0, 30.7, 29.6, 29.55, 29.3, 26.4, 25.3, 25.0, 24.13, 24.11, 23.8, 23.7, 22.7, 11.5; HRMS Calcd. for: [M−H] C$_{66}$H$_{88}$O$_4$P: 975.6426; found: 974.6416.

Example 2

2.1 Preparation of Dihydropyranyl amine (S3):

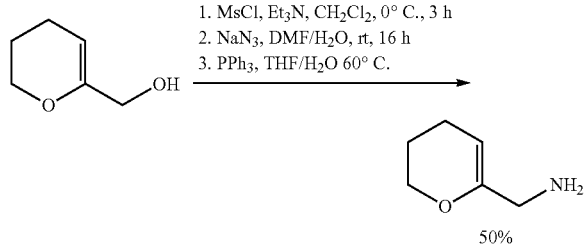

(3,4-dihydro-2H-pyran-6-yl)methanol (Reference) (4.6 g, 40.4 mmol, 1.0 equiv) was dissolved in CH$_2$Cl$_2$ (125 mL) and cooled to 0° C. To above was added Et$_3$N (8.43 mL, 60.5 mmol, 1.5 equiv) followed by drop-wise addition of methanesulfonylchloride (3.75 mL, 1.2 equiv). The resulting mixture was stirred at 0° C. for 2 h after which Et$_3$N (3.94 mL, 0.7 equiv) and methanesulfonylchloride (1.56 mL, 0.5 equiv) were added. The mixture was stirred for additional 1 h at 0° C. After the elapsed time, water was added and the product was extracted with CH$_2$Cl$_2$, washed with brine and dried over anhydrous MgSO$_4$, filtered and concentrated in vacuo. To thus obtained crude mesylate was added DMF (75 mL) and water (7.5 mL). The above solution was subsequently treated with NaN$_3$ (3.15 g, 48.4 mmol, 1.2 equiv) and the mixture was allowed to stir at rt for 16 h. After the elapsed time, the mixture was extracted with EtOAc and the combined organic extract was washed (3×) with water and brine, dried over anhydrous MgSO$_4$, filtered and concentrated in vacuo, to approximately 75 ml volume. To the resulting solution was added PPh$_3$ (9.7 g, 37 mmol), THF (100 mL) and water (10 mL). The resulting mixture was heated at 60° C. for 2 h. The product was extracted with EtOAc, and the organic layer was washed with water and brine and dried over anhydrous MgSO$_4$, filtered and concentrated in vacuo. The crude product was purified by bulb-to-bulb distillation (85° C., 0.1 mm Hg) to afford 2.3 g of the desired amine (50.4% yield). $^1$H-NMR (300 MHz, CDCl$_3$) δ (ppm) 4.59 (t, J=3.6 Hz, 1H), 3.97 (apt, J=5.4 Hz, 2H), 3.10 (s, 2H), 2.00-1.95 (m, 2H), 1.80-1.73 (m, 2H); $^{13}$C-NMR δ (100.6 MHz, CDCl$_3$) δ (ppm) 154.9, 95.3, 66.2, 45.0, 22.3, 19.9. HRMS (ESI) calcd m/z for C$_6$H$_{12}$ON [M+H]: 114.0913; found: 114.0915.

2.1 General Procedure for the Preparation of Dihydropyranyl Amides (3a-i):

To a 0.1 M CH$_2$Cl$_2$ solution of (3,4-dihydro-2H-pyran-6-yl) methanamine S3 (1.0 equiv) at 0° C. was added Et$_3$N (2.0 equiv) and the appropriate acid chloride (1.1 equiv). The reaction mixture was warmed to room temperature and stirred for 30 min after which water was added. The mixture was extracted with CH$_2$Cl$_2$, washed with brine and dried over anhydrous MgSO$_4$, filtered and concentrated in vacuo. The residue was purified by flash chromatography using Et$_3$N treated silica gel (10-20% EtOAc containing 1% Et$_3$N). The fractions containing the product were combined and evaporated to yield the desired product as crystalline white solids. (Note: Thus obtained products were immediately used for the fluorocyclization reactions. Over time, impurities arising from dimerization of the substrates (acid-catalyzed process) begin to appear.

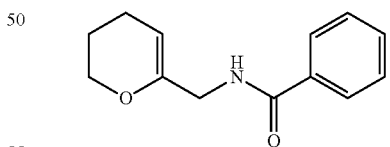

2.2 N-((3,4-dihydro-2H-pyran-6-yl)methyl)benzamide (3a): Prepared according to general procedure above. Flash chromatography (10-20% EtOAc/hexanes containing 1% Et$_3$N) afforded the desired product as crystalline white solid (55% yield). $^1$H-NMR (400 MHz, CDCl$_3$) δ (ppm) 7.77 (d, J=7.6 Hz, 2H), 7.49-7.46 (m, 1H), 7.42-7.39 (m, 2H), 6.49 (m, 1H), 4.6 (t, J=3.6 Hz, 1H), 4.02-3.97 (m, 4 H), 2.05-1.97 (m, 2H), 1.83-1.77 (m, 2H); $^{13}$C-NMR δ (100.6 MHz, CDCl$_3$) δ (ppm) 167.2, 149.9, 134.5, 131.3, 128.4, 126.9, 97.9, 66.3, 42.7, 22.1, 19.9; HRMS calcd m/z for [M+H] C$_{13}$H$_{16}$O$_2$N: 218.1176; found: 218.1177.

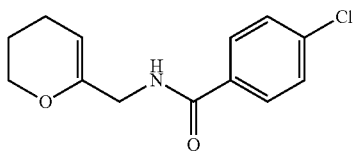 [SMILES: O=C(NCC1=CCCCO1)c1ccc(Cl)cc1]

2.3 4-chloro-N-((3,4-dihydro-2H-pyran-6-yl)methyl)benzamide (3b): Prepared according to general procedure above. Flash chromatography (10-20% EtOAc containing 1% Et$_3$N) afforded the desired product as crystalline white solid (60% yield) $^1$H-NMR (400 MHz, CDCl$_3$) δ (ppm) 7.71 (d, J=8.4 Hz, 2H), 7.36 (d, J=8.4 Hz, 2H), 6.55 (m, 1H) 4.75 (t, J=3.6 Hz, 1H), 3.99 (appt, J=5.2 Hz, 2H), 3.97 (d, J=10 Hz, 2H), 2.02-1.98 (m, 2H), 1.82-1.76 (m, 2H); $^{13}$C-NMR δ (100.6 MHz, CDCl$_3$) δ (ppm) 166.1, 149.8, 137.5, 132.8, 128.6, 128.4, 98.0, 66.4, 42.8, 22.1, 19.9; HRMS calcd m/z for [M+H] C$_{13}$H$_{15}$O$_2$N$^{35}$Cl: 252.0786; found: 252.0787.

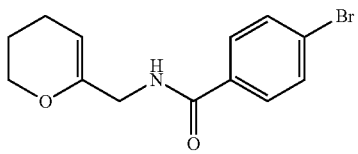 [SMILES: O=C(NCC1=CCCCO1)c1ccc(Br)cc1]

2.4 4-bromo-N-((3,4-dihydro-2H-pyran-6-yl)methyl)benzamide (3c): Prepared according to general procedure above. Flash chromatography (10-20% EtOAc containing 1% Et$_3$N) afforded the desired product as crystalline white solid (52% yield)$^1$H-NMR (400 MHz, CDCl$_3$) δ (ppm) 7.63 (d, J=8.4 Hz, 2H), 7.47 (d, J=8.8 Hz, 2H), 6.82 (m, 1H), 4.70 (t, J=3.6 Hz, 1H), 3.95 (appt, J=4.8 Hz, 2H), 3.91 (d, J=5.2 Hz, 2H), 1.99-1.92 (m, 2H), 1.78-1.72 (m, 2H); $^{13}$C-NMR δ (100.6 MHz, CDCl$_3$) δ (ppm) 166.3, 149.7, 133.1, 131.4, 128.6, 125.8, 97.7, 66.2, 42.6, 22.0, 19.8; HRMS calcd m/z for [M+H] C$_{13}$H$_{15}$O$_2$N$^{79}$Br: 296.0281; found: 296.0283.

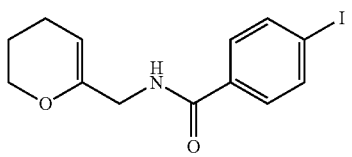 [SMILES: O=C(NCC1=CCCCO1)c1ccc(I)cc1]

2.5 N-((3,4-dihydro-2H-pyran-6-yl)methyl)-4-iodobenzamide (3d): Prepared according to general procedure above. Flash chromatography (10-20% EtOAc containing 1% Et$_3$N) afforded the desired product as crystalline white solid (65% yield). $^1$H-NMR (400 MHz, CDCl$_3$) δ (ppm) 7.75 (d, J=8.4 Hz, 2H), 7.50 (d, J=8.4 Hz, 2H), 6.44 (m, 1H), 4.76 (t, J=3.6 Hz, 1H), 4.01 (appt, J=5.2 Hz, 2H), 3.96 (d, J=5.6 Hz, 2H), 2.03-1.99 (m, 2H), 1.83-1.77 (m, 2H); $^{13}$C-NMR δ (100.6 MHz, CDCl$_3$) δ (ppm) 166.4, 149.7, 137.3, 133.9, 128.6, 98.3, 98.2, 66.4, 42.9, 22.1, 19.9; HRMS calcd m/z for for [M+H] C$_{13}$H$_{15}$O$_2$N$^{127}$I: 344.0142; found: 344.0141.

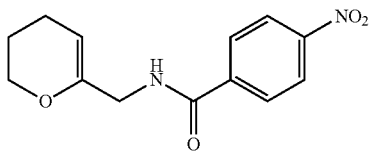 [SMILES: O=C(NCC1=CCCCO1)c1ccc([N+](=O)[O-])cc1]

2.6 N-((3,4-dihydro-2H-pyran-6-yl)methyl)-4-nitrobenzamide (3e): Prepared according to general procedure above. Flash chromatography (10-30% EtOAc containing 1% Et$_3$N) afforded the desired product as crystalline white solid (45% yield): $^1$H-NMR (400 MHz, CDCl$_3$) δ (ppm) 8.24 (d, J=8.8 Hz, 2H), 7.94 (d, J=8.8 Hz, 2H), 6.67 (m, 1H), 4.78 (t, J=3.6 Hz, 1H), 4.02-3.97 (m, 4H), 2.04-1.98 (m, 2H), 1.83-1.77 (m, 2H); $^{13}$C-NMR δ (100.6 MHz, CDCl$_3$) δ (ppm) 165.2, 149.4, 149.3, 140.0, 128.2, 123.7, 98.5, 66.4, 43.1, 22.0, 19.9; HRMS calcd m/z for [M+H] C$_{13}$H$_{15}$O$_4$N$_2$: 263.1026; found: 263.1028.

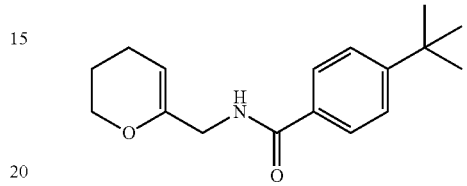

2.7 4-(tert-butyl)-N-((3,4-dihydro-2H-pyran-6-yl)methyl)benzamide (3f): Prepared according to general procedure above. Flash chromatography (10-20% EtOAc containing 1% Et$_3$N) afforded the desired product as crystalline white solid (70% yield). $^1$H-NMR (400 MHz, CDCl$_3$) δ (ppm) 7.72 (d, J=8.4 Hz, 2H), 7.43 (d, J=8.4 Hz, 2H), 6.40 (m, 1H), 4.77 (t, J=3.6 Hz, 1H), 4.12-3.98 (m, 4H), 2.05-1.98 (m, 2H), 1.83-1.77 (m, 2H), 1.32 (s, 9H); $^{13}$C-NMR δ (100.6 MHz, CDCl$_3$) δ (ppm) 167.1, 154.7, 150.1, 131.5, 126.9, 126.7, 125.3, 97.5, 66.2, 42.5, 34.7, 31.0, 22.1, 19.8, 18.4; HRMS calcd m/z for [M+H] C$_{17}$H$_{24}$O$_2$N: 274.1802; found: 274.1802.

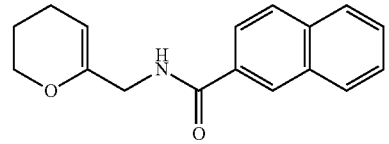 [SMILES: O=C(NCC1=CCCCO1)c1ccc2ccccc2c1]

2.8 N-((3,4-dihydro-2H-pyran-6-yl)methyl)-2-naphthamide (3g): Prepared according to general procedure above. Flash chromatography (10-20% EtOAc containing 1% Et$_3$N) afforded the desired product as crystalline white solid (55% yield). $^1$H-NMR (400 MHz, CDCl$_3$) δ (ppm) 8.30 (s, 1H), 7.90-7.84 (m, 4H), 7.56-7.64 (m, 2H), 6.66 (m, 1H), 4.81 (t, J=3.6 Hz, 1H), 4.06-4.02 (m, 4H), 2.05-2.01 (m, 2H), 1.84-1.71 (m, 2H); $^{13}$C-NMR δ (100.6 MHz, CDCl$_3$) δ (ppm) 167.3, 150.0, 134.6, 132.5, 131.7, 128.9, 128.3, 127.7, 127.5, 127.4, 126.6, 123.6, 98.0, 66.4, 42.9, 22.1, 19.9; HRMS calcd m/z for [M+H] C$_{17}$H$_{18}$O$_2$N: 268.1332; found: 268.1332.

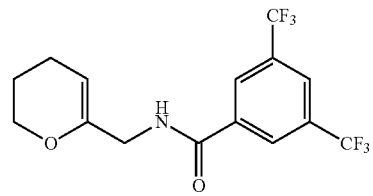 [SMILES: O=C(NCC1=CCCCO1)c1cc(C(F)(F)F)cc(C(F)(F)F)c1]

2.9 N-((3,4-dihydro-2H-pyran-6-yl)methyl)-3,5-dimethoxybenzamide (3h): Prepared according to general procedure above. Flash chromatography (5-10% EtOAc containing 1% Et$_3$N) afforded the desired product as crystalline white solid (80% yield) $^1$H-NMR (400 MHz, CDCl$_3$) δ (ppm) 8.23 (s, 2H), 8.00 (s, 1H), 6.54 (m, 1H), 4.82 (t, J=3.6 Hz, 1H), 4.06-4.02 (m, 4H0, 2.05-2.04 (m, 2H), 1.86-1.82 (m, 2H); $^{13}$C-NMR δ (100.6 MHz, CDCl$_3$) δ (ppm) 164.3, 149.3, 136.6, 132.1 (q, J$_{C-F}$=45.3 Hz), 127.4, 126.9, 124.8 122.3 (q, J$_{C-F}$=272.6 Hz), 98.8, 66.5, 43.3, 22.1, 19.9; HRMS calcd m/z for [M+H] C$_{17}$H$_{24}$O$_2$N: 274.1802; found: 274.1802

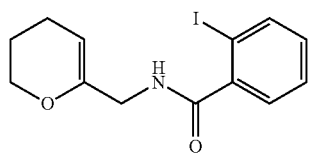 [SMILES: O=C(NCC1=CCCCO1)c1ccccc1I]

2.10 N-((3,4-dihydro-2H-pyran-6-yl)methyl)-2-iodobenzamide (3i): Prepared according to general procedure above. Flash chromatography (10-20% EtOAc containing 1% Et$_3$N) afforded the desired product as crystalline white solid (72% yield). $^1$H-NMR (400 MHz, CDCl$_3$) δ (ppm) 7.85 (d, J=8.0 Hz, 1H), 7.41-7.35 (m, 2H), 7.09 (ddd, J=8.0, 8.0, 1.6 Hz), 6.05 (m, 1H), 4.83 (t, J=3.6 Hz, 1H), 4.02 (apt, J=4.8 Hz, 2H), 3.98 (d, J=5.6 Hz, 2H), 2.06-2.00 (m, 2H), 1.84-1.73 (m, 2H); $^{13}$C-NMR δ (100.6 MHz, CDCl$_3$) δ (ppm) 169.0, 149.5, 142.2, 139.8, 131.0, 128.3, 128.1, 98.3, 92.4, 66.3, 42.8, 22.1, 19.9; HRMS calcd m/z for [M+H] C$_{17}$H$_{24}$O$_2$N: 274.1802; found: 274.1802.

Example 3

3.1 Synthetic Scheme for Synthesis of Dihydropyranyl and Chromenyl Substrates:

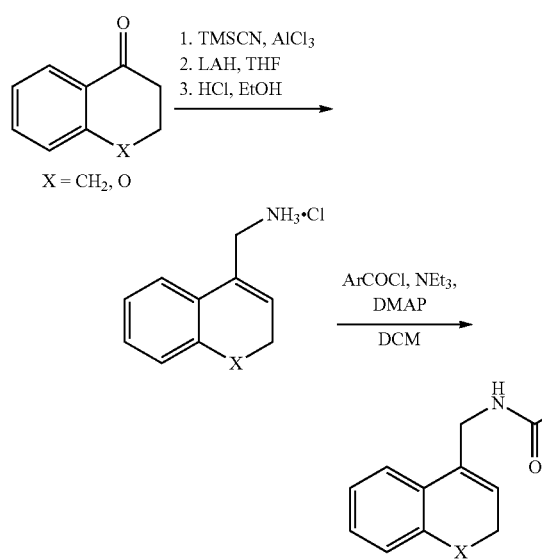

3.1 (3,4-dihydronaphthalen-1-yl)methanammonium chloride (S5a): Prepared according to the methods of Trivedi et al.[39]. To alpha-tetralone (1.97 ml, 16.2 mmol) and AlCl$_3$ (3 mg, 0.02 mmol) in an oven dried 100 ml round bottom flask under N$_2$ was added TMSCN (1.4 ml, 17.8 mmol). The reaction mixture was warmed to 35° C. and stirred for 20 h. To the reaction mixture was added 30 ml THF, and it was then cooled to 0° C. LAH (740 mg, 19.4 mmol) was added portionwise and warmed to 23° C. The reaction mixture was stirred under N$_2$ for 3 h. The reaction was quenched by the addition of NaSO$_4$.10H$_2$O. After stirring 1 h the heterogeneous mixture became white in color. The reaction mixture was filtered, washing with Et$_2$O (2×15 ml). The filtrate was concentrated and redissolved in EtOH (100 ml). 10 ml conc. HCl was added and the reaction mixture was heated to 60° C. and stirred for 16 h. The reaction mixture was concentrated to dryness by rotary evaporation and the resulting solid was washed with Et$_2$O and dichloromethane. The resulting colorless crystalline solid was dried under high vacuum to give S5a (1.1 g, 35% yield). $^1$H NMR: (400 MHz, CD$_3$OD) δ 7.25-7.24 (m, 2H), 7.21-7.19 (m, 2H), 6.24 (t, J=4.4 Hz, 1H), 3.98 (s, 2H), 2.79 (t, J=8.0 Hz, 2H), 2.40-2.30 (m, 2H); $^{13}$C NMR: (125 MHz, CD$_3$OD) δ 137.9, 133.1, 131.6, 131.4, 129.2, 129.2, 128.1, 123.2, 41.7, 28.7, 24.1; HRMS (ESI) exact mass for M-H of free amine (C$_{11}$H$_{14}$N) calcd m/z 160.1121 found 160.1122.

[39] Trivedi, B. K., et al. *J Med. Chem.* 1991, 34, 1043-1049

3.2 (2H-chromen-4-yl)methanammonium chloride (S5d): Prepared analogously to S5a. To 4-chromanone (1.61 g, 10.9 mmol) and AlCl$_3$ (3 mg, 0.02 mmol) in an oven dried 100 ml round bottom flask under N$_2$ was added TMSCN (940 ul, 11.9 mmol). The reaction mixture was warmed to 35° C. and stirred for 20 h. To the reaction mixture was added 30 ml THF, and it was then cooled to 0° C. LAH (494 mg, 13.0 mmol) was added portionwise and warmed to 23° C. The reaction mixture was stirred under N$_2$ for 3 h. The reaction was quenched by the addition of NaSO$_4$.10H$_2$O. After stirring 1 h the heterogeneous mixture became white in color. The reaction mixture was filtered, washing with Et$_2$O (2×15 ml). The filtrate was concentrated and redissolved in EtOH (100 ml). 10 ml conc. HCl were added and the reaction mixture was heated to 60° C. and stirred for 16 h. The reaction mixture was concentrated to dryness by rotary evaporation and the resulting solid was washed with Et$_2$O and dichloromethane. The resulting colorless crystalline solid was dried under high vacuum to give S5d (610 mg, 29% yield). $^1$H NMR (400 MHz, CD$_3$OD) δ 7.22-7.17 (m, 2H), 6.96 (t, J=7.6 Hz, 1H), 6.82 (d, J=7.6 Hz, 1H), 5.97 (t, J=3.6 Hz, 1H), 4.77 (d, J=3.6 Hz, 2H), 2.96 (s, 2H); $^{13}$C NMR (125 MHz, CD$_3$OD) δ 154.3, 129.8, 127.5, 122.5, 122.2, 121.4, 120.5, 116.0, 64.5, 38.7; HRMS (ESI) exact mass for M–H of free amine (C$_{10}$H$_{12}$ON) calcd m/z 162.0913 found 162.0914.

3.3 General Procedure for synthesis of dihydronaphthyl and chromenyl substrates: In a 20 ml scintillation vial containing S5a or S5d (98 mg, 0.5 mmol) in dichloromethane (5 ml) was added NEt$_3$ (280 ul, 2.0 mmol). The reaction mixture became homogeneous, and the substituted benzoyl chloride (0.75 mmol) was added followed by DMAP (6 mg, 0.05 mmol). The reaction mixture was stirred at 23° C. for 3 h. The reaction was quenched by the addition of saturated aqueous NH$_4$Cl (15 ml). The aqueous phase was extracted with dichloromethane (3×15 ml) and the combined organic phases were dried with MgSO$_4$, filtered and concentrated by rotoray evaporation. Purification by flash column chromatography afforded the substituted benzamide substrate.

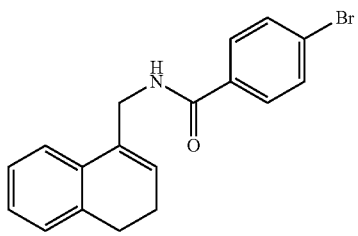 [SMILES: O=C(NCC1=CCCc2ccccc21)c1ccc(Br)cc1]

3.4 4-bromo-N-((3,4-dihydronaphthalen-1-yl)methyl) benzamide (5a): Prepared according to the above general procedure on a 1.0 mmol scale. Flash column chromatography on silica eluting with 13:4:3 hexanes/dichloromethane/ethyl acetate) afforded 5a (280 mg, 82% yield) as a colorless crystalline solid. $^1$H NMR: (500 MHz, CDCl$_3$) δ 7.64 (d, J=8.5 Hz, 2H), 7.55 (d, J=8.5 Hz, 2H), 7.30 (t, J=3.5 Hz, 1H), 7.25-7.20 (m, 3H), 6.23 (br s, 1H), 6.14 (t, J=4.5 Hz, 1H), 4.50 (d, J=5 Hz, 2H), 2.82 (t, J=8.0 Hz, 2H), 2.48-2.34 (m, 2H); $^{13}$C NMR: (125 MHz, CDCl$_3$) δ 166.4, 136.5, 133.3, 132.9, 132.8, 131.8, 128.7, 128.6, 127.9, 127.5, 126.8, 126.2, 122.6, 42.6, 27.9, 23.1; HRMS (ESI) exact mass for MH$^+$ (C$_{18}$H$_{17}$NOBr) calcd m/z 342.0488 found 342.0491.

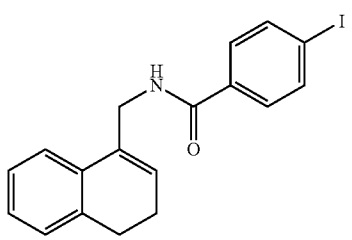 [SMILES: O=C(NCC1=CCCc2ccccc21)c1ccc(I)cc1]

3.5 4-iodo-N-((3,4-dihydronaphthalen-1-yl)methyl)benzamide (5b): Prepared according to the above general procedure on a 0.5 mmol scale. Flash column chromatography on silica eluting with 13:4:3 hexanes/dichloromethane/ethyl acetate) afforded 5b (94 mg, 48% yield) as a colorless crystalline solid. $^1$H NMR: (500 MHz, CDCl$_3$) δ 7.76 (d, J=8.5 Hz, 2H), 7.49 (d, J=8.5 Hz, 2H), 7.30-7.26 (m, 1H), 7.23-7.19 (m, 3H), 6.24 (br s, 1H), 6.14 (t, J=4.0 Hz, 1H), 4.49 (d, J=5.0 Hz, 2H), 2.82 (t, J=8.0 Hz, 2H), 2.38-2.34 (m, 2H); $^{13}$C NMR (125 MHz, CDCl$_3$) δ 166.6, 137.8, 136.5, 133.9, 132.9, 132.8, 128.6, 128.6, 127.9, 127.5, 126.8, 122.6, 98.4, 42.5, 27.9, 23.1; HRMS (ESI) exact mass for M–H (C$_{18}$H$_{17}$NOI) calcd m/z 390.0349 found 390.0354.

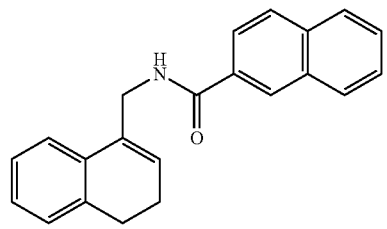 [SMILES: O=C(NCC1=CCCc2ccccc21)c1ccc2ccccc2c1]

3.6 N-((3,4-dihydronaphthalen-1-yl)methyl)-2-naphthamide (5c): Prepared according to the above general procedure on a 0.5 mmol scale. Flash column chromatography on silica eluting with 13:4:3 hexanes/dichloromethane/ethyl acetate) afforded 5c (124 mg, 79% yield) as a colorless crystalline solid. $^1$H NMR: (500 MHz, CDCl$_3$) δ 8.30 (s, 1H), 7.94-7.84 (m, 4H), 7.60-7.54 (m, 2H), 7.39 (d, J=5.0 Hz, 1H), 7.26-7.25 (m, 1H), 6.33 (br s, 1H), 6.19 (t, J=4 Hz, 1H), 4.58 (d, J=4 Hz, 2H), 2.87 (t, J=8 Hz, 2H), 2.41-2.37 (m, 2H); $^{13}$C NMR: (125 MHz, CDCl$_3$) δ 167.4, 136.5, 134.8, 133.1, 133.0, 132.6, 131.7, 128.9, 128.6, 128.5, 127.9, 127.8, 127.7, 127.4, 127.4, 126.8, 126.8, 123.6, 122.8, 42.6, 28.0, 23.1; HRMS (ESI) exact mass for M–H (C$_{22}$H$_{20}$NO) calcd m/z 314.1539 found 314.1542.

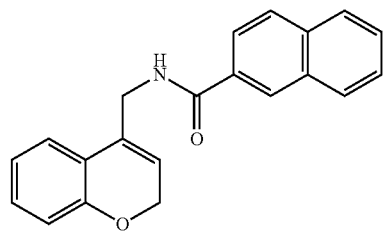 [SMILES: O=C(NCC1=CCOc2ccccc21)c1ccc2ccccc2c1]

3.7 N-((2H-chromen-4-yl)methyl)-2-naphthamide (5d): Prepared according to the above general procedure on a 1.0 mmol scale. Flash column chromatography on silica eluting with 13:4:3 hexanes/dichloromethane/ethyl acetate) afforded 5d (144 mg, 91% yield) as a colorless crystalline solid. $^1$H NMR (500 MHz, CDCl$_3$) δ 8.32 (s, 1H), 7.90-7.85 (m, 4H), 7.60-7.53 (m, 2H), 7.25 (dd, J=8.0 Hz, 1.5 Hz, 1H), 7.18 (td, J=8.0 Hz, 1.5 Hz, 1H), 6.93 (t, J=8.0 Hz, 1H), 6.87 (d, J=8.0 Hz, 1H), 6.63 (br s, 1H), 5.83 (t, J=3.5 Hz, 1H), 4.80 (d, J=3.5 Hz, 2H), 4.51 (d, J=4.5 Hz, 2H); $^{13}$C NMR (125 MHz, CDCl$_3$), δ 167.6, 154.3, 134.8, 132.6, 131.4, 130.9, 129.6, 129.0, 128.6, 127.8, 127.5, 126.8, 123.6, 123.3, 121.7, 121.6, 120.1, 116.2, 65.3, 40.9; HRMS (ESI) exact mass for M–H (C$_{21}$H$_{18}$NO$_2$) calcd m/z 316.1332 found 316.1334.

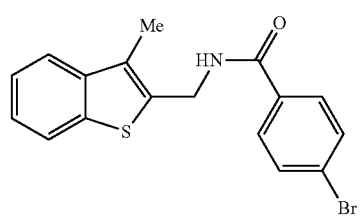 [SMILES: Cc1c(CNC(=O)c2ccc(Br)cc2)sc2ccccc12]

3.8 4-bromo-N-((3-methylbenzo[b]thiophen-2-yl)methyl)benzamide (10a): Prepared from the corresponding amine and 4-bromobenzoyl chloride according to the general procedure above. Flash chromatography (5-10% EtOAc/hexanes) afforded the desired compound as a crystalline white solid in 60% yield. $^1$H-NMR (400 MHz, CDCl$_3$) δ (ppm) 7.75 (d, J=7.6 Hz, 1H), 7.63 (d, J=7.6 Hz, 1H), 7.61 (d, J=7.6 Hz, 2H), 7.48 (d, J=8.4 Hz, 2H), 7.39-7.36 (m, 1H), 7.34-7.30 (m, 1H), 6.75 (m, 1H), 4.80 (d, J=5.2 Hz, 2H), 2.38 (s, 3H); $^{13}$C-NMR δ (100.6 MHz, CDCl$_3$) δ (ppm) 166.3, 140.4, 138.5, 134.2, 132.7, 131.7, 129.4, 128.6, 126.3, 124.5, 124.1, 122.3, 121.8, 37.4, 11.6; HRMS calcd m/z for [M+H] C$_{17}$H$_{15}$ON$^{79}$Br$^{32}$S: 360.0052; found: 360.0057.

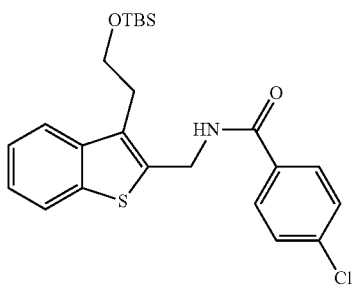 [SMILES: CC(C)(C)[Si](C)(C)OCCc1c(CNC(=O)c2ccc(Cl)cc2)sc2ccccc12]

3.9 N-((3-(2-((tert-butyldimethylsilyl)oxy)ethyl)benzo[b]thiophen-2-yl)methyl)-4-chlorobenzamide (10b): Prepared from the corresponding amine and 4-bromobenzoyl chloride according to the general procedure above. Flash chromatography (0-5% EtOAc/hexanes) afforded the desired compound as a crystalline white solid in 60% yield. $^1$H-NMR (400 MHz, CDCl$_3$) δ (ppm) 7.78 (d, J=8.0 Hz, 1H), 7.73 (d, J=8.4 Hz, 2H), 7.67 (d, J=7.6 Hz, 2H), 7.37-7.30 (m, 4H), 6.91 (m, 1H), 4.87 (d, J=4.8 Hz, 2H), 3.89 (t, J=4.8 Hz, 2H), 3.13 (t, J=4.8 Hz, 2H), 0.80 (s, 9H), −0.16 (s, 6H); $^{13}$C-NMR δ (100.6 MHz, CDCl$_3$) δ (ppm) 167.2, 139.7, 138.8, 137.7, 132.5, 130.8, 128.7, 124.4, 124.1, 122.5, 121.7, 62.5, 37.7, 29.9, 25.9, 18.4, −5.6; HRMS calcd m/z for [M+H] C$_{22}$H$_{31}$O$_2$N$^{35}$Cl$^{32}$S$^{28}$Si: 460.1528; found: 460.1530.

Example 4

4.1 General Procedure for the fluorocyclization of dihydropyran-derived Benzamides: To a 30 mL test-tube equipped with a stir-bar and rubber septa was added the benzamide substrate (3a-i) (0.5 mmol, 1.0 equiv), Proton Sponge (1.1 equiv) and chiral phosphoric acid (2b) (5 mol %). To the heterogeneous mixture was added fluorobenzene (5.0 mL). The resulting solution was cooled to −20° C. and maintained at this temperature for 10 minutes. After the elapsed time, Selectfluor (1.25 equiv) was added in one portion. The tube was capped with a rubber septum and the mixture was stirred at −20° C. for 24 h. After the elapsed time, the reaction mixture was quenched by addition of saturated aqueous Na$_2$S$_2$O$_3$. The reaction mixture was extracted with CH$_2$Cl$_2$ and the combined organic extract was washed with brine and dried over anhydrous MgSO$_4$, filtered and concentrated in vacuo. The diastereoselectivity of the reaction was determined from thus obtained crude products by $^{19}$F-NMR. Thus obtained crude product was loaded onto silica-gel and purified by flash chromatography (5-10% EtOAc/hexanes) to afford the desired products. Absolute stereochemistry was determined by X-ray crystallography of 4c, all other products assigned by analogy.

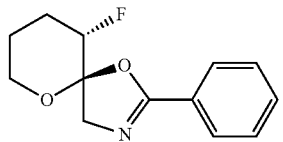 [SMILES: F[C@H]1CCCO[C@@]12CN=C(c1ccccc1)O2]

4.2 (5R,10S)-10-fluoro-2-phenyl-1,6-dioxa-3-azaspiro[4.5]dec-2-ene (4a): Prepared according to the general procedure outlined above and obtained as an off-white solid (92.0 mg, 86% yield). $^1$H-NMR (400 MHz, CDCl$_3$) δ (ppm) 7.95-7.93 (m, 2H), 7.50-7.46 (m, 1H), 7.43-7.35 (m, 2H), 4.59 (dt, J$_{H-F}$=47.2 Hz, J$_{H-H}$=2.8 Hz 1H), 4.11 (d, J=15.6 Hz, 1H), 4.05 (m, 1H), 3.92 (d, J=16.4 Hz, 1H), 3.83-3.81 (dd, J=11.2, 4.4 Hz, 1H), 2.22-2.06 (m, 3H), 1.54-1.57 (m, 1H); $^{13}$C-NMR (100.6 MHz, CDCl$_3$) δ (ppm) 161.9, 131.5, 128.3, 128.0, 127.5, 105.3 (d, J$_{C-F}$=28.2 Hz), 86.8 (d, J$_{C-F}$=175.0 Hz), 63.4 (d, J$_{C-F}$=129.7 Hz), 25.3 (d, J$_{C-F}$=21.1 Hz), 18.6); $^{19}$F-NMR (376.4 MHz) δ (ppm) −192.44-−192.72 (m); HRMS (ESI) Calcd. for [M+H] C$_{13}$H$_{15}$O$_2$NF: 236.1081; found: 236.1081. HPLC (ChiralPak IC column) 95:05 (hexane/iPrOH) 1 mL/min; T$_{major}$ (9.0 min), T$_{minor}$ (10.3 min); 92% ee.

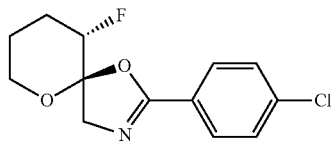 [SMILES: F[C@H]1CCCO[C@@]12CN=C(c1ccc(Cl)cc1)O2]

4.3 (5R,10S)-2-(4-chlorophenyl)-10-fluoro-1,6-dioxa-3-azaspiro[4.5]dec-2-ene (4b): Prepared according to the general procedure outlined above and obtained as a colorless solid (130.0 mg, 97% yield) $^1$H-NMR (400 MHz, CDCl$_3$) δ (ppm) 7.85 (d, J=8.4 Hz, 2H), 7.37 (d, J=8.4 Hz, 2H), 4.57 (dt, J=2.8 Hz, J$_{H-F}$=47.6 Hz, 1H), 4.09 (d, J=16.4 Hz, 1H), 4.01 (dt, J=12.0, 2.0 Hz, 1H), 3.90 (d, J=16.4 Hz, 1H), 3.85-3.81 (m, 1H), 2.18-2.00 (m, 3H), 1.54-1.47 (m, 1H); $^{13}$C-NMR (100.6 MHz, CDCl$_3$) δ (ppm) 161.1, 137.6, 129.3, 128.6, 125.9, 105.6 (d, J$_{C-F}$=28.2 Hz), 86.7 (d, J$_{C-F}$=175.0 Hz), 63.4 (d, J$_{C-F}$=122.7 Hz), 25.2 (d, J$_{C-F}$=20.1 Hz), 18.6; $^{19}$F-NMR (376.4 MHz) δ (ppm) −192.36-−192.64 (m); HRMS (ESI) Calcd. for [M+H] C$_{13}$H$_{14}$O$_2$N$^{35}$ClF: 270.0692; found: 70.0693. HPLC (ChiralPak IC column) 98:02 (hexane/iPrOH) 1 mL/min; T$_{major}$ (9.6 min), T$_{minor}$ (10.4 min); 95% ee.

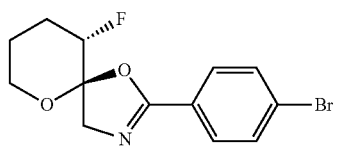

4.4 (5R,10S)-2-(4-bromophenyl)-10-fluoro-1,6-dioxa-3-azaspiro[4.5]dec-2-ene (4c): Prepared according to the general procedure outlined above and obtained as an off-white solid (130.2 mg, 83.6% yield) $^1$H-NMR (400 MHz, CDCl$_3$) δ (ppm) 7.78 (dt, J=8.4 Hz, J$_{H-F}$=2.4 Hz, 2H), 7.53 (dt, J=8.4 Hz, J$_{H-F}$=2.4 Hz, 2H), 4.57 (dt, J=2.8 Hz, J$_{H-F}$=44.8 Hz, 1H), 4.08 (dd, J=16.4, J$_{H-F}$=0.8 Hz, 1H), 4.01 (dt, J=12.8, 2.8 Hz, 1H), 3.85-3.81 (m, 1H), 2.17-2.00 (m, 3H), 1.53-1.47 (m, 1H); $^{13}$C-NMR (100.6 MHz, CDCl$_3$) δ (ppm)

161.1, 131.6, 129.5, 126.4, 126.1, 105.6 (d, $J_{C-F}$=28.2 Hz), 86.7 (d, $J_{C-F}$=175.3 Hz), 63.4 (d, $J_{C-F}$=126.0 Hz), 25.2 (d, $J_{C-F}$=21.2 Hz), 18.6; $^{19}$F-NMR (376.4 MHz) δ (ppm) −192.35--192.63 (m); HRMS (ESI) Calcd. for [M+H] $C_{13}H_{14}O_2N^{79}BrF$: 314.0186; found: 314.0188. HPLC (ChiralPak IC column) 95:05 (hexane/iPrOH) 1 mL/min; $T_{major}$ (10.1 min), $T_{minor}$ (11.0 min); 92% ee. ORTEP visualization of crystal structure shown below.

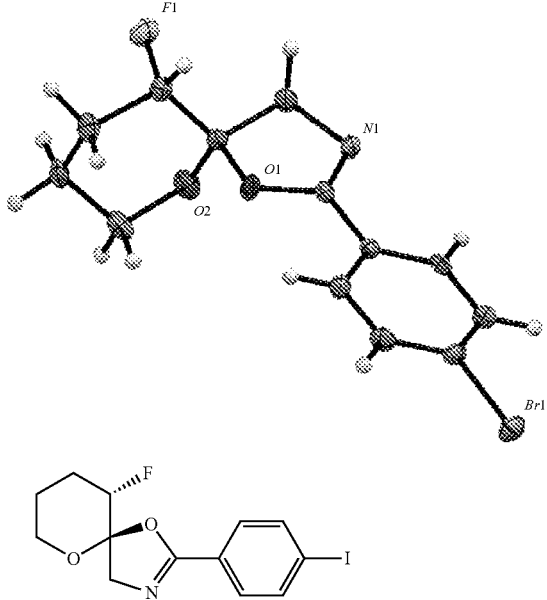

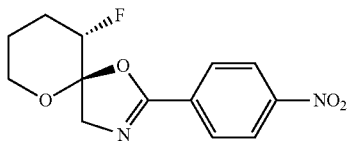 [SMILES: O=[N+]([O-])c1ccc(C2=NC[C@@]3(OCCC[C@@H]3F)O2)cc1]

4.5 (5R,10S)-10-fluoro-2-(4-iodophenyl)-1,6-dioxa-3-azaspiro[4.5]dec-2-ene (4d): Prepared according to the general procedure outlined above and obtained as a faint yellow solid (170.3 mg, 95% yield) $^1$H-NMR (400 MHz, CDCl$_3$) δ (ppm) 7.74 (d, J=8.4 Hz, 2H), 7.62 (d, J=8.4 Hz, 2H), 4.56 (dt, J=2.8 Hz, $J_{H-F}$=47.2 Hz, 1H), 4.07 (d, J=16.4 Hz, 1H), 4.00 (dt, J=12.4, 2.4 Hz, 1H), 3.87 (d, J=16.8 Hz, 1H), 3.84-3.80 (m, 1H), 2.17-2.00 (m, 3H), 1.53-1.45 (m, 1H); $^{13}$C-NMR (100.6 MHz, CDCl$_3$) δ (ppm) 161.2, 137.5, 129.5, 126.9, 105.5 (d, $J_{C-F}$=28.2 Hz), 98.5, 86.7 (d, $J_{C-F}$=174.0 Hz), 63.4 (d, $J_{C-F}$=125.8 Hz), 25.2 (d, $J_{C-F}$=20.1 Hz), 18.5; $^{19}$F-NMR (376.4 MHz) δ (ppm) −192.31--192.59 (m); HRMS (ESI) Calcd. for [M+H] $C_{13}H_{14}O_2N^{127}IF$: 362.0048; found: 362.0044. HPLC (ChiralPak IC column) 98:02 (hexane/iPrOH) 1 mL/min; $T_{major}$ (11.1 min), $L_{minor}$ (10.4 min); 97% ee.

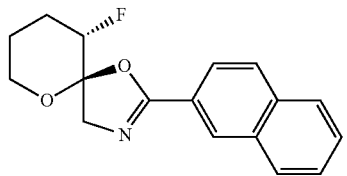 [SMILES: F[C@H]1CCCO[C@@]12CN=C(c1ccc3ccccc3c1)O2]

4.6 (5R,10S)-10-fluoro-2-(4-nitrophenyl)-1,6-dioxa-3-azaspiro[4.5]dec-2-ene (4e): Prepared according to the general procedure outlined above and obtained as a colorless solid (94.0 mg, 67% yield) $^1$H-NMR (400 MHz, CDCl$_3$) δ (ppm) 8.25 (d, J=8.8 Hz, 2H), 8.09 (d, J=8.4 Hz, 2H), 4.61 (dt, J=2.8 Hz, $J_{H-F}$=47.2 Hz, 1H), 4.14 (d, J=16.8 Hz, 1H), 4.02 (dt, J=12.4, 2.4 Hz, 1H), 3.94 (d, J=16.8 Hz, 1H), 3.87-3.83 (m, 1H), 2.25-2.03 (m, 3H), 1.58-1.49 (m, 1H); $^{13}$C-NMR (100.6 MHz, CDCl$_3$) δ (ppm) 160.1, 149.5, 133.2, 129.0, 123.5, 106.2 (d, $J_{C-F}$=28.1 Hz), 86.6 (d, $J_{C-F}$=175.0 Hz), 63.9 (d, $J_{C-F}$=127.8 Hz), 25.2 (d, $J_{C-F}$=20.1 Hz), 18.5; $^{19}$F-NMR (376.4 MHz) δ (ppm) −192.31--192.59 (m); HRMS (ESI) Calcd. for [M+H] $C_{13}H_{14}O_4N_2F$: 281.0932; found: 281.0932. HPLC (ChiralPak IC column) 95:05 (hexane/iPrOH) 1 mL/min; $T_{major}$ (17.4 min), $T_{minor}$ (20.2 min); 97% ee.

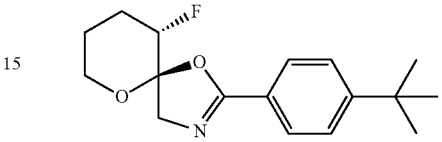

4.7 (5R,10S)-2-(4-(tert-butyl)phenyl)-10-fluoro-1,6-dioxa-3-azaspiro[4.5]dec-2-ene (4f): Prepared according to the general procedure outlined above and obtained as a colorless solid (137.3 mg, 94.8% yield) $^1$H-NMR (400 MHz, CDCl$_3$) δ (ppm) 7.87 (d, J=8.4 Hz, 2H), 7.43 (d, J=8.4 Hz, 2H), 4.57 (d, $J_{H-F}$=47.2 Hz, 1H), 4.10 (d, J=16.4 Hz, 1H), 4.04 (dt, J=11.0, 2.0 Hz, 1H), 3.91 (d, J=16.0 Hz, 1H), 3.83-3.81 (m, 1H), 2.21-2.01 (m, 3H), 1.51-1.48 (m, 1H), 1.33 (s, 9H); $^{13}$C-NMR (100.6 MHz, CDCl$_3$) δ (ppm) 162.0, 155.0, 127.8, 125.3, 124.6, 105.2 (d, $J_{C-F}$=28.2 Hz), 86.9 (d, $J_{C-F}$=175.0 Hz), 63.0 (d, $J_{C-F}$=130.0 Hz), 34.9, 31.0. 25.3 (d, $J_{C-F}$=20.1 Hz), 18.5; $^{19}$F-NMR (376.4 MHz) δ (ppm) −192.40--192.68 (m); HRMS (ESI) Calcd. for [M+H] $C_{17}H_{23}O_2NF$: 292.1707; found: 292.1706. HPLC (Chiralpak IC column) 98:02 (hexane/iPrOH) 1 mL/min; $T_{major}$ (14.7 min), $T_{minor}$ (17.9 min); 95% ee.

4.8 (5R,10S)-10-fluoro-2-(naphthalen-2-yl)-1,6-dioxa-3-azaspiro[4.5]dec-2-ene (4g): Prepared according to the general procedure outlined above and obtained as a faint yellow solid (132.0 mg, 94% yield) $^1$H-NMR (400 MHz, CDCl$_3$) δ (ppm) 8.42 (s, 1H), 8.03 (dd, J=8.4, 1.2 Hz, 1H), 7.92 (d, J=7.6 Hz, 1H), 7.88-7.85 (m, 2H), 7.57-7.51 (m, 2H), 4.65 (d, $J_{H-F}$=46.8 Hz), 4.18 (d, J=16.4 Hz, 1H), 4.12 (d, J=11.2 Hz, 1H), 3.99 (d, J=16.4 Hz, 1H), 3.90-3.86 (m, 1H), 2.32-2.04 (m, 3H), 1.57-1.52 (m, 1H); $^{13}$C-NMR (100.6 MHz, CDCl$_3$) δ (ppm) 162.1, 134.7, 132.5, 128.8, 128.5, 128.2, 127.8, 127.6, 126.6, 124.8, 124.5, 105.5 (d, $J_{C-F}$=28.2 Hz), 86.9 (d, $J_{C-F}$=175.0 Hz), 63.5 (d, $J_{C-F}$=131.8 Hz), 25.3 (d, $J_{C-F}$=21.1 Hz), 18.7; $^{19}$F-NMR (376.4 MHz) δ (ppm) −192.30--192.57 (m); HRMS (ESI) Calcd. for [M+H] $C_{17}H_{17}O_2NF$: 286.1238; found: 286.1236. HPLC (ChiralPak IC column) 95:05 (hexane/iPrOH) 1 mL/min; $T_{major}$ (11.4 min), $T_{minor}$ (13.2 min); 96% ee.

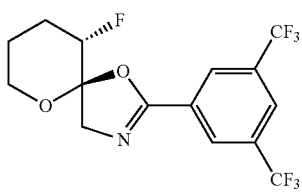

4.9 (5R,10S)-2-(3,5-bis(trifluoromethyl)phenyl)-10-fluoro-1,6-dioxa-3-azaspiro[4.5]dec-2-ene (4h): Prepared according to the general procedure outlined above and obtained as a faint-yellow solid (123.8 mg, 80% yield, 0.4 mmol scale). $^1$H-NMR (400 MHz, CDCl$_3$) δ (ppm) 8.73 (s, 2H), 7.98 (s, 1H), 4.61 (dt, J=2.8 Hz, J$_{H-F}$=46.4 Hz, 1H), 4.15 (d, J=16.8 Hz, 1H), 4.05 (dt, J=10.8, 2.0 Hz, 1H), 3.95 (d, J=16.8 Hz, 1H), 3.88-3.85 (m, 1H), 2.25-2.03 (m, 3H), 1.57-1.54 (m, 1H); $^{13}$C-NMR (100.6 MHz, CDCl$_3$) δ (ppm) 159.5, 132.1 (q, J$_{C-F}$=33.2 Hz), 129.8, 128.1, 124.8, 122.9 (q, J$_{C-F}$=272.6 Hz), 106.6 1 (d, J$_{C-F}$=28.2 Hz), 86.6 (d, J$_{C-F}$=175.0 Hz), 63.6 (d, J$_{C-F}$=102.6 Hz), 25.2 (d, J$_{C-F}$=21.1 Hz), 18.5; $^{19}$F-NMR (376.4 MHz) δ (ppm) −62.29 (s), −192.28-192.55 (m); HRMS (ESI) Calcd. for [M+H] C$_{15}$H$_{12}$F$_7$NO$_2$: found: HPLC (ChiralPak IC column) 99.9:0.01 (hexane/iPrOH) 1 mL/min; T$_{major}$ (12.9 min), T$_{minor}$ (16.0 min); 79% ee.

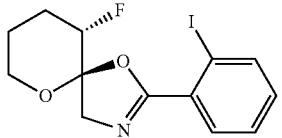

4.10 (5R,10S)-10-fluoro-2-(2-iodophenyl)-1,6-dioxa-3-azaspiro[4.5]dec-2-ene (4i): Prepared according to the general procedure outlined above and obtained as a faint-yellow solid (131.8 mg, 73% yield, 0.5 mmol scale). $^1$H-NMR (400 MHz, CDCl$_3$) δ (ppm) 7.93 (d, J=8.0 Hz, 1H), 7.68 (d, J=7.6 Hz, 1H), 7.38 (t, J=7.6 Hz, 1H), 7.13 (d, J=8.0 Hz, 1H), 4.64 (d, J$_{H-F}$=47.2 Hz, 1H), 4.14 (d, J=16.4 Hz, 1H), 4.07 (d, J=10.0 Hz, 1H), 3.92 (d, J=16.4 Hz, 1H), 3.88-3.84 (m, 1H), 2.21-2.03 (m, 3H), 1.52-1.47 (m, 1H), 1.33 (s, 9H); $^{13}$C-NMR (100.6 MHz, CDCl$_3$) δ (ppm) 162.0, 140.6, 133.0, 131.1, 127.8, 106.2 (d, J$_{C-F}$=28.2 Hz), 94.0, 86.5 (d, J$_{C-F}$=175.0 Hz), 63.6 (d, J$_{C-F}$=97.6 Hz), 25.1 (d, J$_{C-F}$=20.1 Hz), 18.5; $^{19}$F-NMR (376.4 MHz) δ (ppm) −193.03--193.30 (m); HRMS (ESI) Calcd. for [M+H] C$_{17}$H$_{23}$O$_2$NF: 292.1707; found: 292.1706. HPLC (ChiralPakIC column) 95:05 (hexane/iPrOH) 1 mL/min; T$_{major}$ (11.2 min), T$_{minor}$ (12.5 min); 89% ee.

Example 5

5.1 General procedure for the asymmetric fluorocyclization of substrates 5a-d In a 25 mm test tube that had been oven dried and cooled under an atmosphere of N$_2$ was added alkene substrate (0.15 mmol), catalyst (R)-2b (0.015 mmol), powdered anhydrous Na$_2$CO$_3$ (0.19 mmol) and a 1:1 hexanes/fluorobenzene solvent mixture (10 ml total). Selectfluor (0.23 mmol) was added last, a 24/40 septum was affixed to the test tube and the reaction mixture was stirred vigorously under N$_2$ at 23° C. for 24 hours. The reaction was quenched by the addition of saturated aqueous Na$_2$S$_2$O$_3$ (15 mL) and stirring of the consequent biphasic mixture for 10 min. The reaction mixture was transferred to a separatory funnel and the organic phase was diluted with dichloromethane (30 ml). The organic phase was collected and the aqueous phase was extracted with dichloromethane (3×15 ml). The combined organic phases were dried with MgSO$_4$, filtered and concentrated. Crude product was analyzed by $^1$H and $^{19}$F NMR to determine diastereoselectivity. The crude product was then purified by flash column chromatography on silica gel, eluting with hexanes/ethyl acetate to afford the desired fluorocyclization product. Enantiopurity was determined by HPLC analysis.

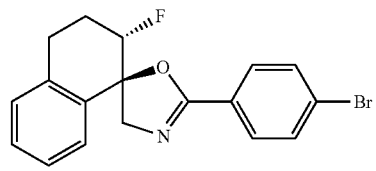 [SMILES: F[C@H]1CCc2ccccc2[C@@]12CN=C(c1ccc(Br)cc1)O2]

5.2 (1R,2S)-2'-(4-bromophenyl)-2-fluoro-3,4-dihydro-2H,4'H-spiro[naphthalene-1,5'-oxazole] (6a): Prepared according to the general procedure on a 0.15 mmol scale (52 mg). Purification by flash column chromatography on silica gel, eluting with 7:1 hexanes/ethyl acetate afforded 6a as a colorless crystalline solid (47 mg, 87% yield). $^1$H NMR (500 MHz, CDCl$_3$) δ 7.91 (d, J=8.5 Hz, 2H), 7.60 (d, J=8.5 Hz, 2H), 7.36-7.33 (m, 1H), 7.31-7.27 (m, 2H), 7.18-7.17 (m, 1H), 5.09 (ddd, J$_{H-F}$=50 Hz, J$_{H-H}$=11 Hz, 3.5 Hz, 1H), 4.56 (d, J=15 Hz, 1H), 4.07 (dd, J=15.5 Hz, 3.0 Hz, 1H), 3.08-2.97 (m, 2H), 2.41-2.32 (m, 1H), 2.20-2.11 (m, 1H); $^{13}$C NMR (125 MHz, CDCl$_3$) δ 162.8, 137.4 (d, J$_{C-F}$=4 Hz), 134.8 (d, J$_{C-F}$=1 Hz), 131.7, 129.9, 128.5, 128.3, 127.5, 126.5 (d, J$_{C-F}$=2 Hz), 126.4, 126.3, 92.1 (d, J$_{C-F}$=180 Hz), 86.9 (d, J$_{C-F}$=20 Hz), 64.2 (d, J$_{C-F}$=6 Hz, 26.5 (d, J$_{C-F}$=10 Hz), 26.1 (d, J$_{C-F}$=19 Hz); $^{19}$F NMR (376 MHz, CDCl$_3$) δ −192.45 (dd, J$_{H-F}$=49 Hz, 19 Hz); HRMS (ESI) exact mass for M−H (C$_{18}$H$_{16}$NOBrF) calcd m/z 360.0394 found 360.0398. HPLC (Chiralpak IA column, 95:5 hexanes/isopropanol, 1 mL/min) t$_r$=12.7 min (major), 14.1 min (minor); 93% ee.

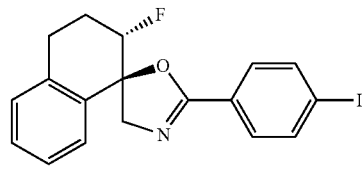 [SMILES: F[C@H]1CCc2ccccc2[C@@]12CN=C(c1ccc(I)cc1)O2]

5.3 (1R,2S)-2'-(4-iodophenyl)-2-fluoro-3,4-dihydro-2H,4'H-spiro[naphthalene-1,5'-oxazole] (6b): Prepared according to the general procedure on a 0.15 mmol scale (58 mg). Purification by flash column chromatography on silica gel, eluting with 7:1 hexanes/ethyl acetate afforded 6b as a colorless solid (44 mg, 71% yield). $^1$H NMR (500 MHz, CDCl$_3$) δ 7.82 (d, J=8.5 Hz, 2H), 7.76 (d, J=8.5 Hz, 2H), 7.35-7.33 (m, 1H), 7.31-7.25 (m, 2H), 7.18-7.17 (m, 1H), 5.08 (ddd, J$_{H-F}$=50.0 Hz, J$_{H-H}$=11.0 Hz, 3.5 Hz, 1H), 4.57 (d, J=15.5 Hz, 1H), 4.06 (dd, J=15.0 Hz, 3.0 Hz, 1H), 3.07-2.97 (m, 2H), 2.41-2.32 (m, 1H), 2.20-2.11 (m, 1H); $^{13}$C NMR (125 MHz, CDCl$_3$) δ 162.3, 137.7, 137.4 (d, J$_{C-F}$=4 Hz), 134.8 (d, J$_{C-F}$=1 Hz), 129.9, 128.5, 128.3, 127.5, 12.0, 126.5 (d, J$_{C-F}$=1 Hz), 98.5, 92.1 (d, J$_{C-F}$=181 Hz), 86.8 (d, J$_{C-F}$=21 Hz), 64.2 (d, J$_{C-F}$=6 Hz), 26.5 (d, J$_{C-F}$=11 Hz), 26.1 (d, J$_{C-F}$=19 Hz); HRMS (ESI) exact mass for M−H (C$_{18}$H$_{16}$NOIF) calcd m/z 408.0255 found 408.0258. HPLC (Chirlpak IA column, 95:5 hexanes/isopropanol, 1 mL/min; $t_r$=14.7 min (major), 16.3 min (minor); 93% ee.

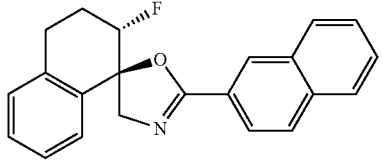 [SMILES: F[C@H]1CCc2ccccc2[C@@]12CN=C(c1ccc3ccccc3c1)O2]

5.4 (1R,2S)-2-fluoro-2'-(naphthalen-2-yl)-3,4-dihydro-2H,4'H-spiro[naphthalene-1,5'-oxazole] (6c): Prepared according to the general procedure on a 0.14 mmol scale (43 mg). Purification by flash column chromatography on silica gel, eluting with 7:1 hexanes/ethyl acetate afforded 6c as a colorless solid (28 mg, 62% yield). $^1$H NMR (500 MHz, CDCl$_3$) δ 8.54 (s, 1H), 8.16 (dd, J=8.5 Hz, 1.5 Hz, 1H), 7.94-7.90 (m, 3H), 7.61-7.54 (m, 2H), 7.45-7.43 (m, 1H), 7.32-7.28 (m, 2H), 2.70-7.10 (m, 1H), 5.17 (ddd, $J_{H-F}$=50 Hz, $J_{H-H}$=11 Hz, 3.5 Hz, 1H), 4.66 (d, J=15.5 Hz, 1H), 4.16 (dd, J=15.0 Hz, 2.5 Hz, 1H), 3.11-3.01 (m, 2H), 2.45-2.38 (m, 1H), 2.25-2.20 (m, 1H); $^{13}$C NMR (125 MHz, CDCl$_3$) δ 163.7, 137.7 (d, $J_{C-F}$=5 Hz), 134.8 (d, $J_{C-F}$=1 Hz), 134.8, 132.7, 128.9, 128.4, 128.3, 1282, 127.8, 127.6, 127.5, 126.6 (d, $J_{C-F}$=2 Hz), 126.6, 124.9, 124.8, 92.6 (d, $J_{C-F}$=181 Hz), 86.5 (d, $J_{C-F}$=21 Hz), 64.3 (d, $J_{C-F}$=6 Hz), 26.5 (d, $J_{C-F}$=11 Hz), 26.2 (d, $J_{C-F}$=20 Hz); $^{19}$F NMR (376 MHz, CDCl$_3$) δ -192.375 (dd, $J_{H-F}$=49 Hz, 19 Hz); HRMS (ESI) exact mass for MH$^+$ (C$_{22}$H$_{19}$FNO) calcd m/z 332.1445 found 332.1444. HPLC (Chirlpak IA column, 95:5 hexanes/isopropanol, 1 ml/min; $t_r$=15.4 min (major), 17.4 min (minor); 96% ee.

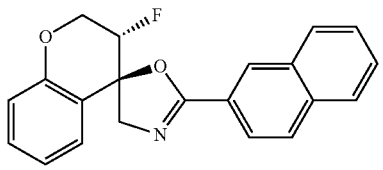 [SMILES: F[C@H]1COc2ccccc2[C@@]12CN=C(c1ccc3ccccc3c1)O2]

5.5 (3S,4R)-3-fluoro-2'-(naphthalen-2-yl)-4'H-spiro[chroman-4,5'-oxazole] (6d): Prepared according to the general procedure on a 0.15 mmol scale (47 mg). Purification by flash column chromatography on silica gel, eluting with 6:1 hexanes/ethyl acetate afforded 6d as a colorless solid (35 mg, 70% yield). $^1$H NMR (500 MHz, CDCl$_3$) δ 8.45 (s, 1H), 8.10 (d, J=8.5 Hz, 1H), 7.93-7.8 (m, 3H), 7.61-7.54 (m, 2H), 7.46 (d, J=8.0 Hz, 1H), 3.42 (t J=8.0 Hz, 1H), 7.07 (d, J=8.0 Hz, 1H), 7.01 (d, J=8.5 Hz, 1H), 5.00 (dd, $J_{H-F}$=45.0 Hz, $J_{H-H}$=3.0 Hz, 1H), 4.64 (d, J=16.0 Hz, 1H), 4.54-4.46 (m, 2H), 4.46 (d, J=15.5 Hz, 1H); $^{13}$C NMR (125 MHz, CDCl$_3$) δ 162.7, 153.5, 134.9, 132.6, 130.7, 129.0, 128.9, 128.3, 128.0, 127.9, 127.8, 126.7, 124.7, 124.4, 122.3, 121.3, 117.2, 86.6 (d, $J_{C-F}$=183 Hz), 80.1 (d, $J_{C-F}$=26 Hz), 64.6, (d, $J_{C-F}$=21 Hz), 63.0 (d, $J_{C-F}$=4 Hz); $^{19}$F NMR (376 MHz, CDCl$_3$) δ 200.70 (ddd, J=49 Hz, 30 Hz, 11 Hz); HRMS (ESI) exact mass for M-H (C$_{21}$H$_{17}$FNO$_2$) calcd m/z 334.1238 found 334.1241. HPLC (Chiralpak IA column, 95:5 hexanes/isopropanol, 1 ml/min; $t_r$=12.2 min (major), 15.2 min (minor); 92% ee.

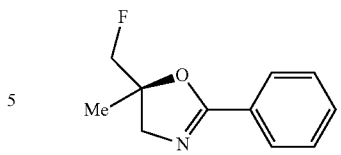

5.6 (R)-5-(fluoromethyl)-5-methyl-2-phenyl-4,5-dihydrooxazole (8): N-(2-methylallyl)benzamide[40] (17.8 mg, 0.1 mmol. 1.0 equiv), Selectfluor (42.0 mg, 0.12 mmol, 1.2 equiv), Na$_2$CO$_3$ (11.6 mg, 0.11 mmol, 1.1 equiv) and phosphoric acid (9) (5.0 mg, 0.005 mmol, 5 mol %) were charged into a 1-dram vial and anhydrous heptane 2.0 ml was charged. The heterogeneous mixture was heated at 60° C. for 24 h after which it was filtered through a cotton-plug. The filtrate was directly loaded onto silica gel. The product was eluted with 10-30% EtOAc/hexanes gradient. Evaporation of fractions containing the product yielded 14.7 mg of the desired product as a glassy solid (75% yield). $^1$H-NMR (400 MHz, CDCl$_3$) δ (ppm) 7.93 (d, J=7.2 Hz, 2H), 7.50-7.46 (m, 1H), 7.43-7.39 (m, 2H), 4.48 (dd, =47.6 Hz, $J_{H-H}$=10.0 Hz, 1H), 4.37 (dd, $J_{H-F}$=47.6 Hz, $J_{H-H}$=10.0 Hz, 1H), 4.01 (d, J=15.2 Hz, 1H), 3.76 (dd, J=14.8, 2.4 Hz, 1H), 1.51 (d, $J_{H-F}$=1.6 Hz, 3H); $^{13}$C-NMR δ (100.6 MHz, CDCl$_3$) δ (ppm) 166.3, 131.4, 128.3, 128.1, 127.6, 85.9 (d, $J_{C-F}$=179.1 Hz), 83.9 (d, $J_{C-F}$=19.1 Hz), 62.2 (d, $J_{C-F}$=3.02 Hz), 21.7 (d, $J_{C-F}$=4.0 Hz); $^{19}$F-NMR (376.4 MHz) δ (ppm) -225.61 (t, $J_{H-F}$=48.9 Hz); HRMS (EI) Calcd. for C$_{12}$H$_{12}$ON$^{19}$F: 193.0903; found: 193.0908.

[40] Samii, Z. K. M.; Ashmawy, M. A. I.; Mellor, J. M. *J. Chem. Soc., Perk. Trans. I.* 1988. 2517.

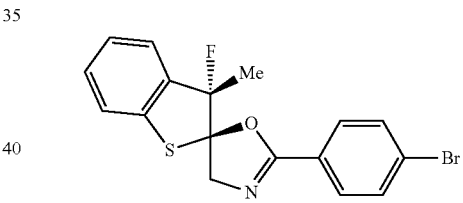

5.7 (2S,3S)-2'-(4-bromophenyl)-3-fluoro-3-methyl-3H,4'H-spiro[benzo[b]thiophene-2,5'-oxazole] (11a): Prepared according to the general procedure for the asymmetric fluorination outlined in the dihydropyran series except that Proton Sponge® was replaced with anhydrous Na$_2$CO$_3$ and that the reaction was run at room temperature. Flash chromatography yielded the desired product as a colorless solid (76 mg, 69% yield, 0.30 mmol scale). $^1$H-NMR (400 MHz, CDCl$_3$) δ (ppm) 7.75 (d, J=8.4 Hz, 2H), 7.53 (d, J=8.4 Hz, 2H), 7.44-7.38 (m, 2H), 7.30 (d, J=8.0 Hz, 1H), 7.26-7.23 (m, 1H), 4.69 (d, J=17.2 Hz, 1H), 4.39 (d, J=17.6 Hz, 1H), 1.79 (d, $J_{H-F}$=20.8 Hz, 3H); $^{13}$C-NMR (100.6 MHz, CDCl$_3$) δ (ppm) 162.0, 141.0 (d, $J_{C-F}$=5.0 Hz), 136.5 (d, $J_{C-F}$=19.1 Hz), 131.7, 131.5 (d, $J_{C-F}$=4.0 Hz), 129.7, 126.6, 125.7, 125.6 (d, $J_{C-F}$=3.0 Hz) m 125.2 (d, $J_{C-F}$=2.0 Hz), 122.9 (d, $J_{C-F}$=3.0 Hz), 105.6 (d, $J_{C-F}$=35.2 Hz), 103.1 ((d, $J_{C-F}$=178.1 Hz), 17.0 (d, $J_{C-F}$=26.1 Hz); $^{19}$F-NMR (376.4 MHz) δ (ppm) -135.82 (q, $J_{H-F}$=18.8 Hz); HRMS (ESI) Calcd. for [M+H] C$_{17}$H$_{14}$ON$^{79}$BrF$^{32}$S: 377.9958; found: 377.9968. HPLC (ChiralPak IC column) 99:01 (hexane/iPrOH) 1 mL/min; T$_{major}$ (10.8 min), T$_{minor}$ (12.1 min); 97% ee.

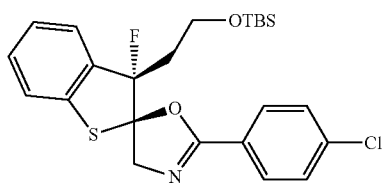 [SMILES: CC(C)(C)[Si](C)(C)OCC[C@]1(F)c2ccccc2S[C@@]12CN=C(c1ccc(Cl)cc1)O2]

5.8 (2S,3S)-3-(2-((tert-butyldimethylsilyl)oxy)ethyl)-2'-(4-chlorophenyl)-3-fluoro-3H,4'H-spiro[benzo[b]thiophene-2,5'-oxazole] (11b): Prepared according to the general procedure for the asymmetric fluorination outlined in the dihydropyran series except that Proton Sponge® was replaced with anhydrous $Na_2CO_3$ and that the reaction was run at room temperature. Flash chromatography yielded the desired product as a colorless solid (53.0 mg, 59% yield, 0.27 mmol scale) $^1$H-NMR (400 MHz, $CDCl_3$) δ (ppm) 7.84 (dt, J=8.4, 1.6 Hz, 2H), 7.52 (d, J=8.0 Hz, 2H), 7.40-7.36 (m, 3H), 7.26-7.21 (m, 2H), 4.71 (dd, J=17.6, 1.6 Hz, 1H), 4.40 (d, J=17.6 Hz, 1H), 3.95 (ddd, J=6.0, 9.6, 9.6 Hz, 1H), 3.77 (ddd, J=5.2, 9.6, 9.6 Hz, 1H), 2.65 (dddd, J=6.0, 9.6, 14.8, 14.8 Hz, 1H), 2.44 (ddddd, J=5.6, 9.2, 14.8, 14.8 Hz, 1H), 0.82 (s, 9H), −0.06 (s, 6H); $^{13}$C-NMR (100.6 MHz, $CDCl_3$) δ (ppm) 161.7, 140.1 (d, $J_{C-F}$=5.0 Hz), 138.2, 136.1 (d, $J_{C-F}$=19.1 Hz), 131.3 (d, $J_{C-F}$=3.0 Hz), 128.8, 128.3, 126.0, 125.6 (d, $J_{C-F}$=3.0 Hz), 125.2, 122.9, 105.7 (d, $J_{C-F}$=34.2 Hz), 103.9 ((d, $J_{C-F}$=183.1 Hz), 61.7 (d, $J_{C-F}$=6.0 Hz), 58.0 (d, $J_{C-F}$=7.0 Hz), 36.1 (d, $J_{C-F}$=24.1 Hz) 25.8, 18.2, −5.5; HRMS (ESI) Calcd. for [M+H] $C_{24}H_{30}O_2N^{35}ClF^{32}S^{28}Si$: 478.1434; found: 478.1438. HPLC (ChiralPak IA column) 99.9:0.01 (hexane/iPrOH) 1 mL/min; $T_{major}$ (10.3 min), $T_{minor}$ (15.7 min); 97% ee.

Example 6

Nonlinear effect study

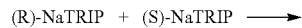

(R)-NaTRIP + (S)-NaTRIP ⟶
1:1-1:0 ration

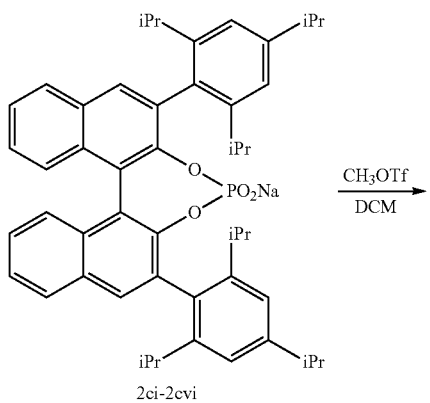

2ci-2cvi

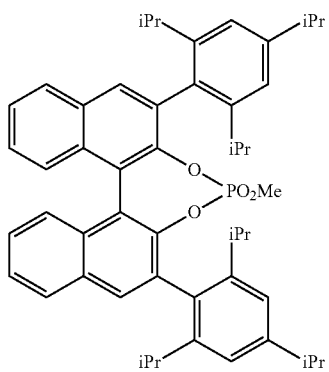

6.1 Preparation of Enantioenriched Phosphate Catalysts (R)- and (S)-NaTRIP (citation) were combined in ratios of approximately 1:1, 3:2, 7:3, 4:1, 9:1 and 1:0 on a total scale of 0.025 mmol. The combined chiral phosphate salts were dissolved in 10 ml $C_6H_5F$. In order to determine the optical purity of each catalyst mixture, 1 ml aliquots were removed, concentrated, redeposited in dichloromethane, and an excess of $CH_3OTf$ was added to generate the phosphate methyl esters for HPLC analysis. The reaction mixtures were stirred 1 h, at which point TLC indicated conversion of starting material. The reaction mixtures were concentrated, taken up in HPLC hexanes, filtered through Wattman paper filters and analyzed by HPLC (Whelk column, 99.9:0.01 hexanes/isopropanol, 1 ml/min) $t_r$=5.9 min (minor), 8.8 min (major). The observed enantioenrichents are 2ci: >99%, 2cii: 82%, 2ciii: 63%, 2civ: 45%, 2cv: 24%, 2cvi: 2%

6.2 Assessment of Effect of Enantiopurity of Catalyst on Enantiopurity of Product Each reaction was run in duplicate and the plotted data is an average of the two results. To 5a (8.6 mg, 0.025 mmol), $Na_2CO_3$ (2.9 mg, 0.0275 mmol), and catalyst 2c(i-vi) in 1 mL $C_6H_5F$ was added Selectfluor® (9.7 mg, 0.0275 mmol). The reaction mixture was stirred at 23° C. for 12 h. The reaction mixture was filtered through cotton, washing with $Et_2O$, and concentrated. The crude filtrate was dissolved in EtOAc, filtered through a Wattman paper filter and submitted directly for HPLC analysis (Chiralpak IC column, 99:01 hexanes/isopropanol, 1 ml/min) $t_r$=18.7 min (minor), 19.7 (major). The enantiopurities are presented below as a function of the catalyst enantiopurity. One result (catalyst 2civ, run 2) has been discarded as a result of HPLC data compromised by spectral artifacts.

| Catalyst | % ee (Catalyst) | % ee (Product) |
| --- | --- | --- |
| 2ci | >99 | 93 |
| 2ci | >99 | 93 |
| 2cii | 82 | 67 |
| 2cii | 82 | 67 |
| 2ciii | 63 | 48 |
| 2ciii | 63 | 48 |
| 2civ | 45 | 45 |
| 2civ | 45 | xx |
| 2cv | 24 | 16 |
| 2cv | 24 | 16 |
| 2cvi | 2 | 4 |
| 2cvi | 2 | 3 |

Example 7

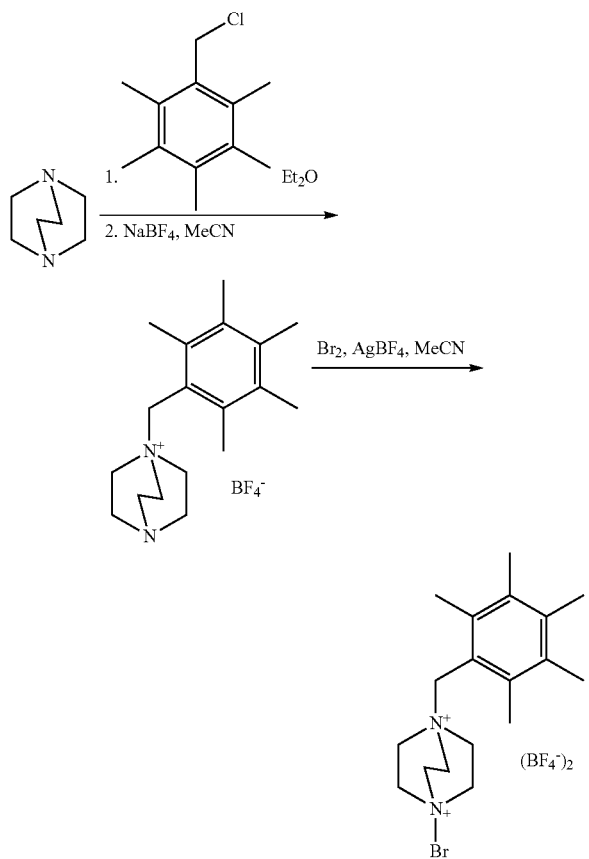

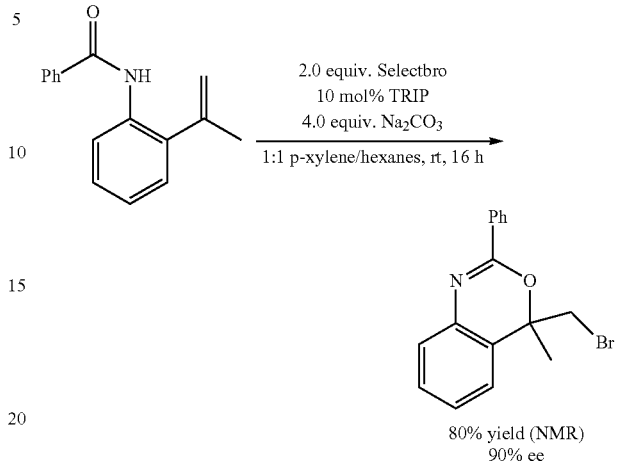

7.2 Bromocyclization Using "Selectbro" in Phase Transfer Conditions

General procedure: Xylene/hexanes (1:1, 0.8 mL) was added to the substrate (10.0 mg, 0.042 mmol), freshly pulverized and dried Na2CO3 (17.8 mg, 0.168 mmol), TRIP (3.1 mg, 0.0042 mmol), and the phase-transfer brominating agent (45 mg). A stirbar was added, and the reaction mixture was stirred at 700 rpm for 16 h. The reaction mixture was filtered through cotton and glass wool, concentrated, and chromatographed (prep TLC) to provide the desired bromination product in 80% yield (NMR), 90% ee.

Example 8

8.1 Alpha Fluorination of Enamines

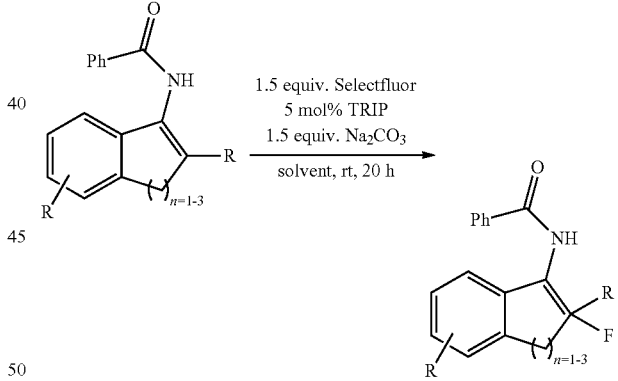

7.1 Synthesis of Electrophilic Bromination Reagent, "Selectbro"

Pentamethylbenzyl chloride (1.96 g, 10 mmol) and DABCO (1.17 g, 10.5 mmol) were stirred in diethyl ether (10 mL) for 48 h. The white crystalline solid was filtered and washed with hexanes to give 1-(2,3,4,5,6-pentamethylbenzyl)-1,4-diazabicyclo[2.2.2]octan-1-ium chloride. A suspension of the crude chloride and NaBF$_4$ (5.49 g, 50 mmol) in MeCN (150 mL) was sonicated for 15 min and filtered. The filtrate was concentrated to give 1-(2,3,4,5,6-pentamethylbenzyl)-1,4-diazabicyclo[2.2.2]octan-1-ium tetrafluoroborate (3.05 g, 88%) as a colorless powder (1H NMR (CD$_3$CN): 4.62 (s, 2H), 3.18-3.11 (m, 6H), 3.03-2.97 (m, 6H), 2.30 (s, 6H), 2.27 (s, 3H), 2.23 (s, 6H)).

To a stirred solution of the benzylammonium tetrafluoroborate salt (1.00 g, 2.78 mmol) and AgBF$_4$ (0.567 g, 2.91 mmol) in MeCN (100 mL) was added Br$_2$ (0.490 g, 3.07 mmol) over 5 min. After an additional 5 min of stirring, the reaction mixture was filtered. To the filtrant was added successively CH$_2$Cl$_2$ (100 mL) and hexanes (100 mL) to precipitate the product. The resulting mixture was sonicated briefly and filtered to give the crude product, which was washed successively with CH$_2$Cl$_2$, toluene, and hexane. Drying by suction and then high vacuum afforded 0.98 g of the phase-transfer brominating agent (1H NMR (CD$_3$NO$_2$): 4.94 (s, 2H), 3.63-3.83 (m, 12 H, 2.25-2.35 (m, 15 H)).

General procedure: To a 5 mL vial containing an 8 mm magnetic stirrer bar was added hexane or toluene (1 mL, as specified in table below), the enamide substrate (0.1 mmol), SelectFluor (58 mg, 0.15 mmol), Na$_2$CO$_3$ (17 mg, 0.15 mmol) and R-TRIP (3.8 mg, 0.005 mmol). The vial was capped and stirred at a high rate of stirring for 20 h. After this time, saturated NaHCO$_3$ (1 ml) solution was added as well as EtOAc (1 ml) and the mixture was shaken. The organic layer was removed and filtered through a pipette containing Na$_2$SO$_4$ and the solvent was evaporated. Using 1,2-dichloroethane as an internal standard, this crude mixture was analyzed by 1H-NMR to obtain the NMR yield of the product. Following this, the mixture was purified by flash column chromatography to isolate the product and this product was analyzed by HPLC on a chiral IA, IB or IC column.

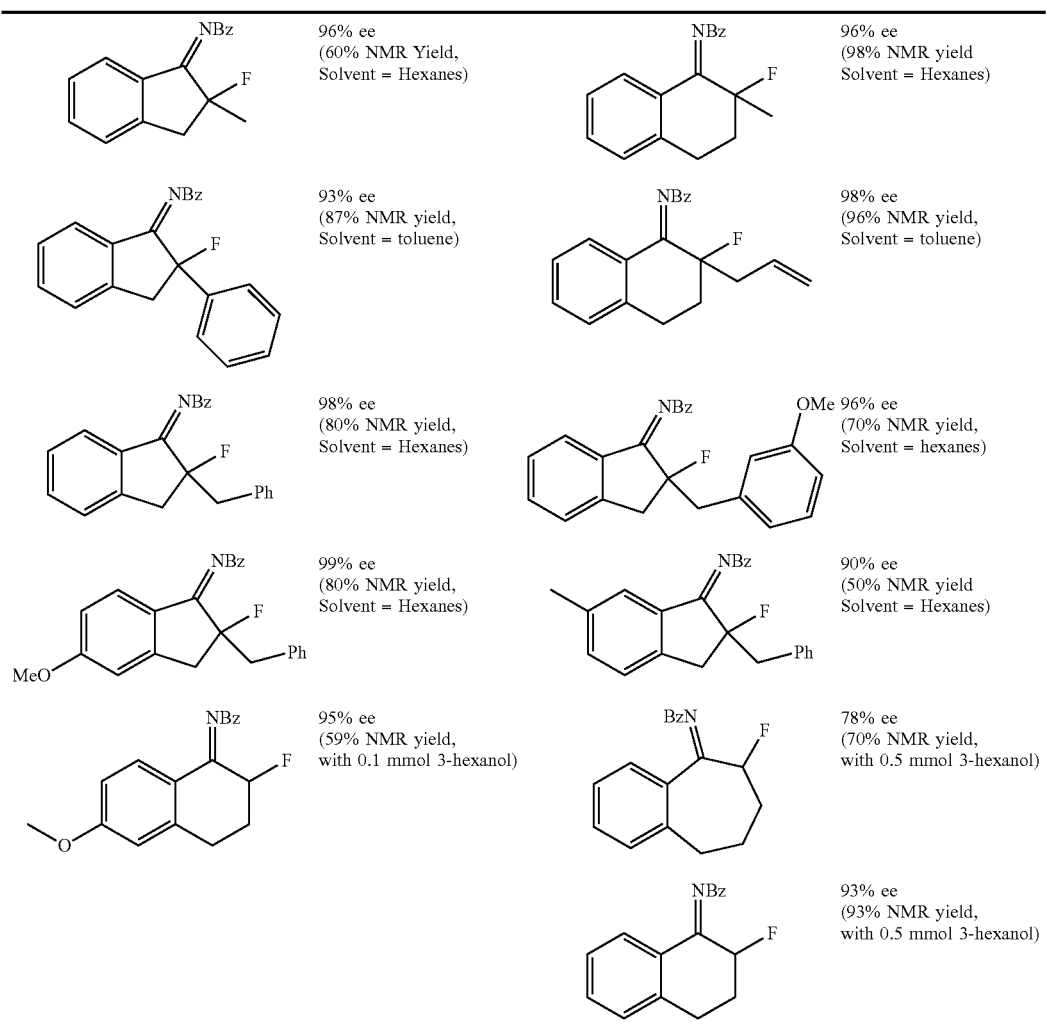
I
In the final example, the general procedure differs only in that 3-hexanol (either 0.1 mmol or 0.5 mmol as specified below) is initially added to the reaction mixture and that all reactions were run using hexanes as solvent.
Example 9
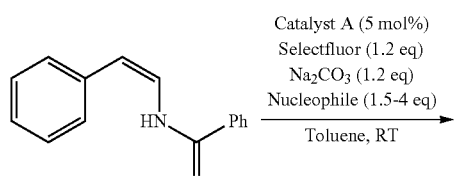
-continued
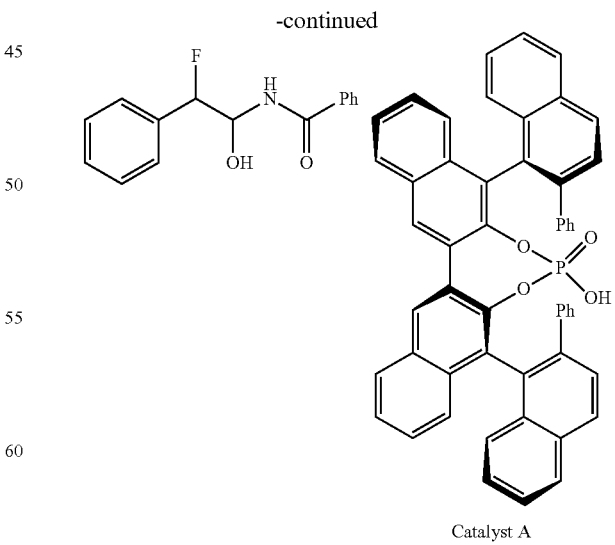
Catalyst A
To Z-enamide 1 (22.3 mg, 0.1 mmol), Catalyst A (3.8 mg, 0.005 mmol), Selectfluor (42.5 mg, 0.12 mmol) and Na$_2$CO$_3$ (12.7 mg, 0.12 mmol) was added Toluene (2 ml). The reaction mixture was stirred for 20 h. To the reaction mixture was added water (1 mL), and extracted with Et$_2$O (2 mL×2). The organic layer was dried over anhydrous Na$_2$SO$_4$, filtered and concentrated in vacuo. The residue was subjected to purification by flash chromatography (Hexane/EtOAc=1/1) to obtain the desired product 22.3 mg (86% yield, d.r.=>20: 1, 98% ee).

Alkoxy- and hydroxyfluorination of alkenes

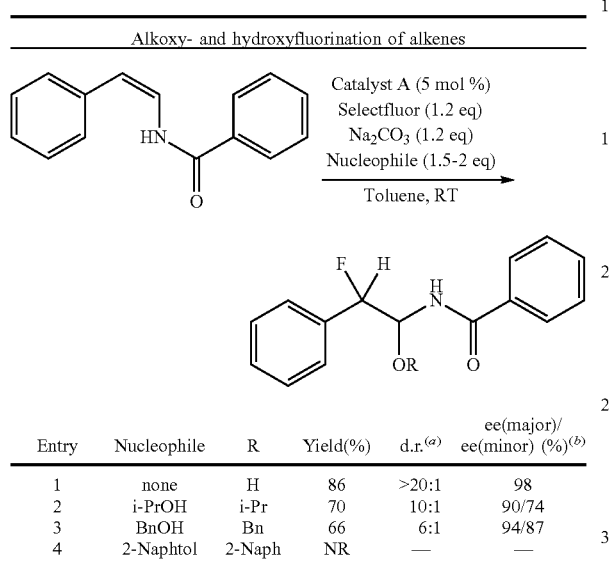

| Entry | Nucleophile | R | Yield(%) | d.r.[a] | ee(major)/ee(minor) (%)[b] |
|---|---|---|---|---|---|
| 1 | none | H | 86 | >20:1 | 98 |
| 2 | i-PrOH | i-Pr | 70 | 10:1 | 90/74 |
| 3 | BnOH | Bn | 66 | 6:1 | 94/87 |
| 4 | 2-Naphtol | 2-Naph | NR | — | — |

[a]Determined by crude NMR.
[b]Determined by Chiral HPLC.

Example 10

10.1 1,2-Fluorocyclization of Dienyl Substrates

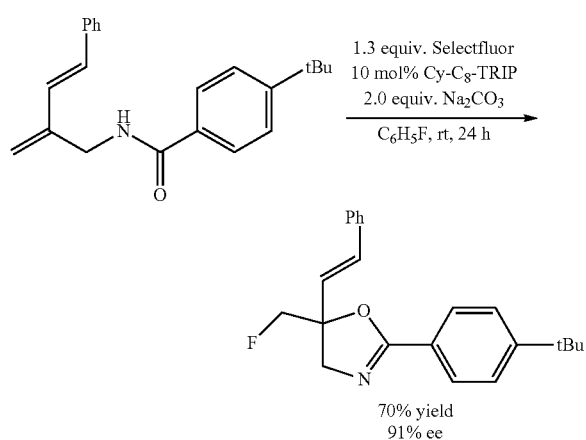

70% yield
91% ee

General procedure: Selectfluor (20.0 mg, 0.058 mmol), Na$_2$CO$_3$ (9.9 mg, 0.094 mmol), cyclohexyl-C8-TRIP (5.7 mg, 10 mol %), and diene substrate 1 (15.0 mg, 0.047 mmol), were added to fluorobenzene (1 mL) in a glass vial and stirred at room temperature for 24 hours. The heterogeneous solution was diluted with diethyl ether and dichloromethane and filtered over a sintered glass funnel. The solution was concentrated and purified by column chromatography on silica gel (1:3 EtOAc:Hexanes) to afford oxazoline 2 (11.0 mg, 70.0%, 91% e.e).

Example 11

11.1 Fluoro-ene Reaction of Styrenyl Substrates

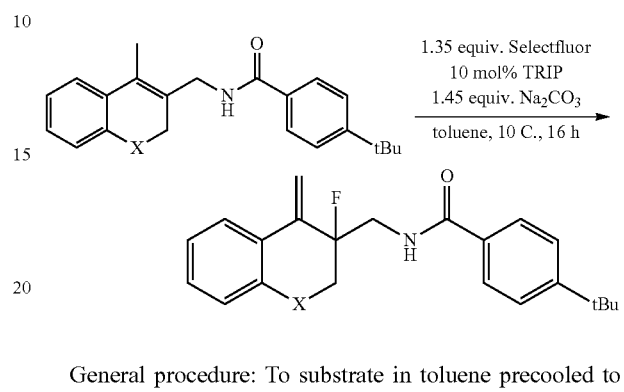

General procedure: To substrate in toluene precooled to 10° C. was added Na$_2$CO$_3$, TRIP and Selectfluor. Heterogeneous reaction mixture was filtered, precipitate washed with Et$_2$O. Filtrate concentrated and analyzed by NMR. Crude product purified by flash column chromatography on silica gel, clean product analyzed for enantiomeric excess by chiral HPLC.

Example 12

12.1 Ring Expansion of Vinyl Cyclopropanols

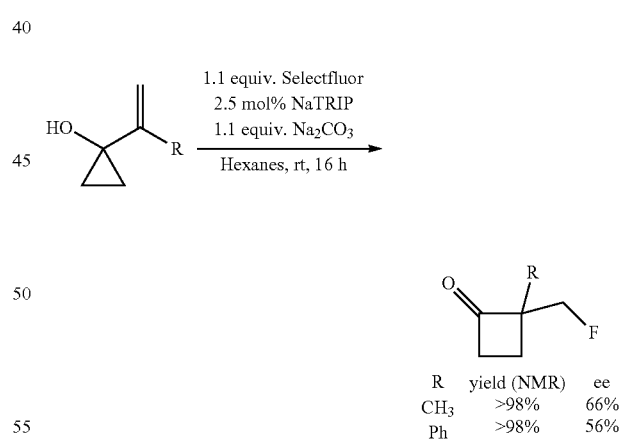

| R | yield (NMR) | ee |
|---|---|---|
| CH$_3$ | >98% | 66% |
| Ph | >98% | 56% |

General procedure: To vinyl cyclopropanol substrate in 0.05 mmol vinyl cyclopropanol substrate in 1 mL hexanes was added 0.00125 mmol (2.5 mol %) NaTRIP, 0.055 mmol (1.1 equiv.) Na$_2$CO$_3$, and 0.055 mmol (1.1 equiv.) Selectfluor. The heterogeneous reaction was stirred 16 h. The reaction mixture was filtered through cotton, washing with Et$_2$O. The filtrate was concentrated and analyzed by $^1$H and $^{19}$F NMR. Enantiomeric excess determined by chiral GC.

Example 13

13.1 1,4-Aminofluorination of Dienyl Substrates

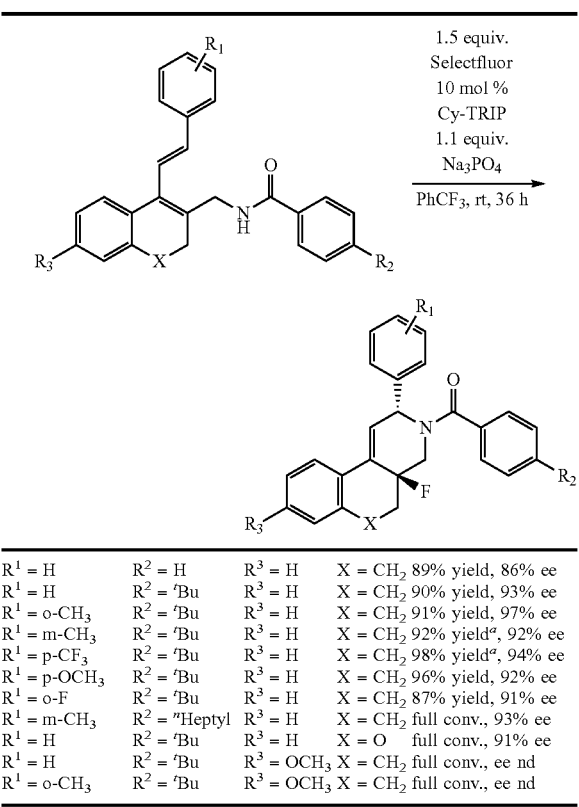

| | | | |
|---|---|---|---|
| R¹ = H | R² = H | R³ = H | X = CH₂ 89% yield, 86% ee |
| R¹ = H | R² = $^t$Bu | R³ = H | X = CH₂ 90% yield, 93% ee |
| R¹ = o-CH₃ | R² = $^t$Bu | R³ = H | X = CH₂ 91% yield, 97% ee |
| R¹ = m-CH₃ | R² = $^t$Bu | R³ = H | X = CH₂ 92% yield$^a$, 92% ee |
| R¹ = p-CF₃ | R² = $^t$Bu | R³ = H | X = CH₂ 98% yield$^a$, 94% ee |
| R¹ = p-OCH₃ | R² = $^t$Bu | R³ = H | X = CH₂ 96% yield, 92% ee |
| R¹ = o-F | R² = $^t$Bu | R³ = H | X = CH₂ 87% yield, 91% ee |
| R¹ = m-CH₃ | R² = $^n$Heptyl | R³ = H | X = CH₂ full conv., 93% ee |
| R¹ = H | R² = $^t$Bu | R³ = H | X = O full conv., 91% ee |
| R¹ = H | R² = $^t$Bu | R³ = OCH₃ | X = CH₂ full conv., ee nd |
| R¹ = o-CH₃ | R² = $^t$Bu | R³ = OCH₃ | X = CH₂ full conv., ee nd |

$^a$determined by $^1$H-NMR

General procedure: To a 5 mL reaction vial was added Amide (0.03 mmol, 11.0 mg), Selectfluor (0.045 mmol, 16.0 mg), Na₃PO₄ (0.033 mmol, 5.4 mg), cyclohexyl-Trip catalyst (0.003 mmol, 3.0 mg) and a magnetic stir bar. To this mixture was added 0.3 mL of trifluoromethylbenzene and the reaction was stirred vigorously (at least 360 rpm) for 36 hours. During this time, the vials were periodically shaken to agitate material adhered to the sides of the vial. After 36 hours, 1 mL of saturated sodium thiosulfate and 1 mL of water were added to quench the reaction. The mixture was subsequently extracted with DCM (3 mL×3) and the combined organics were dried over Na₂SO₄, filtered and concentrated. The crude material was then purified by SiO₂ chromatography with hexanes:DCM:Et₂O (60:35:5 to 50:40:10) (Rf ~0.45 in 50:40:10). Product was isolated as a white solid in 90% yield (0.025 mmol 12.0 mg).

Example 14

Compound numbering in this Example corresponds to FIG. 5-10.
Synthesis of Products

14.1 General Procedure for Asymmetric Fluorination:

To the substrate 1 (0.25 mmol) in a 1 dram (15×45 mm) vial equipped with an 8 mm magnetic stirrer bar was added toluene (1.25 ml). Subsequently, anhydrous Na₂CO₃ (39.8 mg, 0.375 mmol), Selectfluor (132 mg, 0.375 mmol) and (S)-TCYP (12.4 mg, 0.0125 mmol) were added. The vial was capped with a screw cap and stirred rapidly for the specified time at room temperature, the vial standing on the stirrer plate. After this time, the reaction was diluted with ethyl acetate and poured into satd. NaHCO₃ solution. After extraction, the aqueous layer was extracted with further EtOAc and the combined organics were, dried (Na₂SO₄) and evaporated in vacuo. The crude residue was purified by flash column chromatography. It is notable that fast and efficient stirring should be maintained in order to achieve reliable results.

Drying of reagents: Selectfluor® (Sigma Aldrich) was ground in a pestle and morter and dried at 80° C. under high vacuum for 30 minutes Anhydrous Na₂CO₃ was ground in a pestle and morter and dried at 80° C. under high vacuum for 30 minutes.

14.2 (R)-4a-fluoro-5,6,7,8-tetrahydronaphthalen-2(4aH)-one (2a), 3-fluoro-5,6,7,8-tetrahydronaphthalen-2-ol (2b), 1-fluoro-5,6,7,8-tetrahydronaphthalen-2-ol (2c) and 1,1-difluoro-5,6,7,8-tetrahydronaphthalen-2(1H)-one (2d)

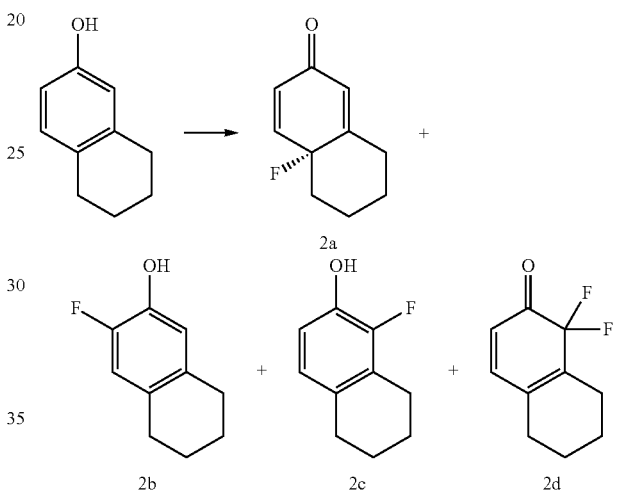

Reaction carried out according to general procedure using 5,6,7,8-Tetrahydro-2-naphthol (37.0 mg, 0.25 mmol) for 40 h. Purification by column chromatography, eluting with a gradient of 50 to 80% CH₂Cl₂ in Hexane gave 2a as a colourless oil (17 mg, 0.102 mmol, 41%). Also isolated was a mixture of 2b and 2c as a colourless oil (10 mg, 0.060 mmol, 24%) and 2d as a yellow solid (5 mg, 11%).

2a: $^1$H NMR (400 MHz, CDCl₃) δ 6.82 (dd, J=10.1, 6.3 Hz, 1H), 6.21 (dt, J=10.1, 1.6 Hz, 1H), 6.06 (s, 1H), 2.63 (tdd, J=13.3, 5.1, 1.6 Hz, 1H), 2.43 (d, J=13.1 Hz, 1H), 2.32 (dddt, J=14.0, 8.0, 3.9, 2.2 Hz, 1H), 2.05 (dtq, J=13.8, 4.9, 2.4 Hz, 1H), 1.88 (tt, J=13.5, 3.9 Hz, 1H), 1.81-1.69 (m, 1H), 1.57-1.33 (m, 2H). $^{19}$F NMR (376 MHz, CDCl₃) δ -155.92 (dt, J=38.6, 6.7 Hz). $^{13}$C NMR (151 MHz, CDCl₃) δ 185.63 (d, J=4.8 Hz), 158.83 (d, J=18.7 Hz), 145.94 (d, J=21.8 Hz), 129.31 (d, J=7.8 Hz), 123.95 (d, J=4.7 Hz), 87.43 (d, J=164.8 Hz), 38.27 (d, J=25.7 Hz), 32.02 (s), 27.38 (s), 20.50 (d, J=1.3 Hz). m/z HRMS (EI) found [M]⁺ 166.0793, C₁₀H₁₁O₁F₁ requires 166.0794. [α]D²⁰=-60.6 (c 1.0, CHCl₃). HPLC (Chiralpak IC column, 99:01 hexanes/isopropanol, 1 ml/min); t$_r$=18.1 min (minor), 24.8 min (major); 63% ee.

2b and 2c: $^1$H NMR (400 MHz, CDCl₃) δ 6.83-6.62 (m, 4H), 4.87 (s, 2H), 2.78-2.57 (m, 8H), 1.85-1.65 (m, 8H). $^{19}$F NMR (376 MHz, CDCl₃) δ -144.47 (t, J=10.1 Hz, 2b), -146.12 (d, J=6.7 Hz, 2c). Copy of $^{13}$C-NMR spectrum of mixture supplied. m/z HRMS (EI) found [M]⁺ 166.0797, C₁₀H₁₁OF₁ requires 166.0794. Assignments made based on comparison of $^{19}F$ shifts and multiplicities with data previously published by Stavber and co-workers.[17]

2d: $^1H$ NMR (600 MHz, CDCl$_3$) δ 6.75 (d, J=10.1 Hz, 1H), 6.04 (d, J=10.0 Hz, 1H), 2.33-2.37 (m, 2H), 2.29-2.23 (m, 2H), 1.75-1.70 (m, 4H). $^{19}F$ NMR (376 MHz, CDCl$_3$) δ −109.37 (s). $^{13}C$ NMR (151 MHz, CDCl$_3$) δ 189.27 (t, J=23.8 Hz), 145.78 (t, J=3.0 Hz), 136.89 (t, J=23.6 Hz), 133.24 (t, J=9.2 Hz), 122.04 (t, J=3.6 Hz), 104.03 (t, J=242.1 Hz), 28.61 (s), 21.70 (s), 21.58 (t, J=2.1 Hz), 20.81 (s). m/z HRMS (EI) found [M]$^+$ 184.0702, C$_{10}$H$_{10}$OF$_2$ requires 184.0700.

14.3 (R)-8a-fluoro-6,7,8,8a-tetrahydronaphthalen-1(5H)-one (3a)

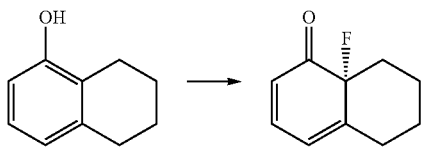 [SMILES: Oc1cccc2c1CCCC2 ; O=C1C=CC=C2CCCC[C@]12F]

Reaction carried out according to general procedure using 5,6,7,8-Tetrahydro-1-naphthol (37.0 mg, 0.25 mmol) for 48 h. Purification by column chromatography, eluting with 10% Et$_2$O in Hexane gave the title compound as a yellow oil (31 mg, 0.187 mmol, 75%). $^1H$ NMR (400 MHz, CDCl$_3$) δ 6.99 (dd, J=9.8, 6.1 Hz, 1H), 6.09-6.00 (m, 2H), 2.57 (td, J=12.9, 4.5 Hz, 1H), 2.37 (d, J=12.8 Hz, 1H), 2.21 (dddt, J=14.6, 8.4, 4.0, 2.2 Hz, 1H), 2.03 (dtq, J=13.6, 4.7, 2.3 Hz, 1H), 1.91 (tt, J=13.5, 3.9 Hz, 1H), 1.80-1.65 (m, 1H), 1.62-1.36 (m, 2H). $^{19}F$ NMR (376 MHz, CDCl$_3$) δ −166.20 (dd, J=38.8, 8.4 Hz). $^{13}C$ NMR (151 MHz, CDCl$_3$) δ 199.07 (d, J=14.6 Hz), 153.57 (d, J=18.3 Hz), 142.28 (s), 123.85 (d, J=4.6 Hz), 117.06 (d, J=6.1 Hz), 91.77 (d, J=179.8 Hz), 38.53 (d, J=25.6 Hz), 32.02 (s), 30.39 (s), 20.71 (d, J=2.0 Hz). m/z HRMS (EI) found [M]$^+$ 166.0797, C$_{10}$H$_{11}$O$_1$F$_1$ requires 166.0794. [α]D$^{20}$=+666.2 (c 1.0, CHCl$_3$). HPLC (Chiralpak IC column, 96:04 hexanes/isopropanol, 1 ml/min); t$_r$=17.9 min (major), 20.6 min (minor); 96% ee.

14.4 (1S,4R,4aS,8R,8aS,10R)-8,10-difluoro-8,10-dimethyl-4,4a,8,8a-tetrahydro-1,4-ethanonaphthalene-7,9(1H)-dione (4a)

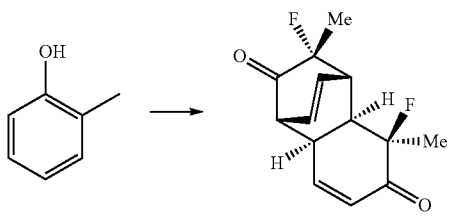

Reaction carried out according to general procedure using ortho-cresol (27.0 mg, 0.25 mmol) for 48 h. Purification by column chromatography, eluting with 1:4:5 CHCl$_3$:Et$_2$O:Hexane gave the title compound as a white solid (20 mg, 0.0794 mmol, 63%). $^1H$ NMR (400 MHz, CDCl$_3$) δ 6.44 (dd, J=10.2, 4.1 Hz, 1H), 6.38 (td, J=7.0, 1.8 Hz, 1H), 6.08 (ddd, J=10.2, 4.1, 1.6 Hz, 1H), 5.99 (t, J=7.2 Hz, 1H), 3.48 (d, J=6.7 Hz, 1H), 3.43 (ddd, J=8.4, 4.1, 2.0 Hz, 1H), 3.35-3.30 (m, 1H), 3.23 (dd, J=8.6, 1.9 Hz, 1H), 1.59 (d, J=22.1 Hz, 3H), 1.43 (d, J=23.1 Hz, 3H). $^{19}F$ NMR (376 MHz, CDCl$_3$) δ −151.87 (q, J=23.0 Hz), −160.74 (q, J=21.9 Hz). $^{13}C$ NMR (151 MHz, CDCl$_3$) δ 203.94 (d, J=16.6 Hz), 195.46 (d, J=18.1 Hz), 144.70 (s), 134.21 (d, J=5.6 Hz), 129.44 (d, J=1.2 Hz), 129.27 (s), 93.43 (d, J=192.4 Hz), 90.66 (d, J=188.4 Hz), 51.59 (s), 43.90 (dd, J=18.9, 12.3 Hz), 41.37 (dd, J=19.5, 5.6 Hz), 39.01 (d, J=4.2 Hz), 28.05 (d, J=26.7 Hz), 22.24 (d, J=27.0 Hz). m/z HRMS (EI) found [M]$^+$ 252.0968, C$_{14}$H$_{14}$O$_2$F$_2$ requires 252.0962. [α]D$^{20}$=−17.0 (c 1.0, CHCl3). HPLC (Chiralpak IC column, 85:15 hexanes/isopropanol, 1 ml/min; t$_r$=15.0 min (major), 16.3 min (minor); 79% ee.

14.5 (1S,4R,4aS,8R,8aS,10R)-8,10-dibenzyl-8,10-difluoro-4,4a,8,8a-tetrahydro-1,4-ethanonaphthalene-7,9(1H)-dione (4b)

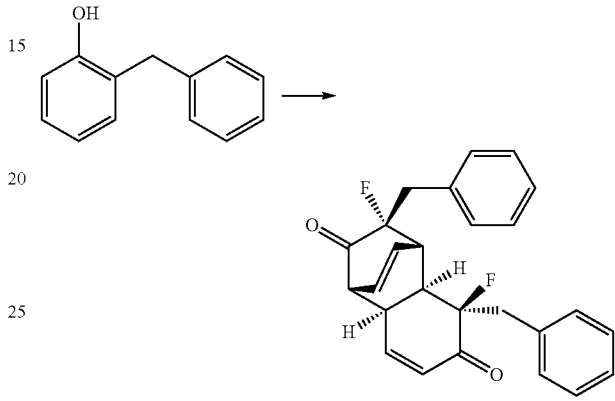

Reaction carried out according to general procedure using 2-benzylphenol (46.0 mg, 0.25 mmol) for 48 h. Purification by column chromatography, eluting with 1:1 Et$_2$O:Hexane gave the title compound as a white solid (41 mg, 0.101 mmol, 81%). $^1H$ NMR (400 MHz, CDCl$_3$) δ 7.36-7.29 (m, 3H), 7.26-7.20 (m, 3H), 7.20-7.11 (m, 2H), 7.10-7.01 (m, 2H), 6.46 (dd, J=10.1, 4.1 Hz, 1H), 6.38 (t, J=7.3 Hz, 1H), 6.05-5.98 (m, 2H), 3.55-3.47 (m, 1H), 3.44-3.38 (m, 1H), 3.29-3.17 (m, 3H), 3.13 (s, 1H), 3.06 (s, 1H), 2.70 (dd, J=37.9, 14.8 Hz, 1H). $^{13}C$ NMR (151 MHz, CDCl$_3$) δ 203.69 (d, J=17.2 Hz), 194.38 (d, J=18.5 Hz), 144.26 (s), 133.99 (d, J=5.7 Hz), 133.81 (s), 133.05 (s), 130.23 (s), 130.16 (s), 129.90 (s), 129.30 (s), 128.51 (s), 128.40 (s), 127.51 (s), 127.43 (s), 96.10 (d, J=198 Hz), 92.34 (d, J=194 Hz), 51.73 (s), 47.00 (d, J=24.0 Hz), 40.45 (d, J=19.3, 12.7 Hz), 40.07 (d, J=4.1 Hz), 39.92 (d, J=24.2 Hz), 39.81 (dd, J=19.4, 5.5 Hz). $^{19}F$ NMR (376 MHz, CDCl$_3$) δ −158.97 (dd, J=37.8, 15.6 Hz), −165.58 (t, J=26.0 Hz). m/z HRMS (EI) found [M]$^1$ 404.1585, C$_{26}$H$_{22}$O$_2$F$_2$ requires 404.1588. [α]D$^{20}$=+32.6 (c 1.0, CHCl3). HPLC (Chiralpak IA column, 90:10 hexanes/isopropanol, 1 ml/min; t$_r$=14.5 min (major), 16.7 min (minor); 97% ee.

14.6 (R)-4-bromo-8a-fluoro-6,7,8,8a-tetrahydronaphthalen-1(5H)-one (3b)

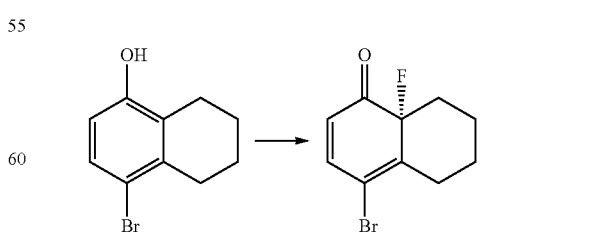

Reaction carried out according to general procedure using 4-bromo-5,6,7,8-tetrahydronaphthalen-1-ol (57.8 mg, 0.25 mmol) for 46 h. Purification by column chromatography, eluting with 10% Et$_2$O in Hexane gave the title compound as a yellow oil (33 mg, 0.135 mmol, 54%). $^1$H NMR (400 MHz, CDCl$_3$) δ 7.12 (d, J=10.2 Hz, 1H), 6.02 (dd, J=10.2, 1.4 Hz, 1H), 2.89 (d, J=13.3 Hz, 1H), 2.49 (td, J=13.2, 4.5 Hz, 1H), 2.20 (dddd, J=11.9, 8.1, 3.7, 1.8 Hz, 1H), 2.10-1.99 (m, 1H), 1.93 (tt, J=13.4, 4.0 Hz, 1H), 1.82-1.68 (m, 1H), 1.66-1.41 (m, 2H). $^{19}$F NMR (376 MHz, CDCl$_3$) δ −159.75 (dd, J=38.6, 7.8 Hz). $^{13}$C NMR (101 MHz, CDCl$_3$) δ 196.90 (d, J=15.3 Hz), 149.75 (d, J=20.0 Hz), 146.69 (d, J=2.8 Hz), 124.26 (d, J=4.3 Hz), 112.22 (d, J=9.2 Hz), 92.94 (d, J=185.2 Hz), 38.67 (d, J=25.6 Hz), 31.94 (s), 28.86 (s), 20.72 (d, J=1.7 Hz). m/z HRMS (EI) found [M]$^+$243.9904, C$_{10}$H$_{10}$O$_1$F$_1$ $^{79}$Br$_1$ requires 243.9899. [α]D$^{20}$=+230.3 (c 1.0, CHCl$_3$). HPLC (Chiralpak IC column, 96:04 hexanes/isopropanol, 1 ml/min); t$_r$=9.6 min (major), 11.6 min (minor); 87% ee.

14.7 (R)-tert-butyl 4a-fluoro-5-oxo-3,4,4a,5-tetrahydroisoquinoline-2(1H)-carboxylate (3c)

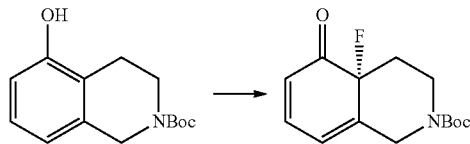 [SMILES: CC(C)(C)OC(=O)N1CCc2c(O)cccc2C1 ; CC(C)(C)OC(=O)N1CC[C@]2(F)C(=O)C=CC=C2C1]

Reaction carried out according to general procedure using 2-tert-butyloxycarbonyl-5-hydroxy-1,2,3,4-tetrahydroisoquinoline (62.2 mg, 0.25 mmol) for 48 h. Purification by column chromatography, eluting with a gradient of 0 to 5% Et$_2$O in CH$_2$Cl$_2$ gave the title compound as a yellow oil (38 mg, 0.1423 mmol, 57%). $^1$H NMR (400 MHz, MeOD) δ 7.19 (dd, J=9.9, 6.0 Hz, 1H), 6.33 (d, J=5.9 Hz, 1H), 6.14 (d, J=9.9 Hz, 1H), 4.58 (d, J=13.8 Hz, 1H), 4.11 (dd, J=13.7, 5.3 Hz, 1H), 3.81 (br s, 1H), 3.33 (br s, 1H), 2.19 (ddt, J=14.8, 10.6, 2.2 Hz, 1H), 1.72 (dddd, J=38.9, 14.6, 12.6, 5.4 Hz, 1H), 1.48 (s, 9H). $^{19}$F NMR (376 MHz, MeOD) δ −166.40 (s). $^{13}$C NMR (151 MHz, MeOD) δ 196.34 (d, J=13.8 Hz), 154.61 (s), 143.80 (d, J=16.0 Hz), 142.06 (d, J=3.2 Hz), 124.64 (d, J=4.9 Hz), 119.77 (br s), 87.91 (d, J=177.1 Hz), 80.41 (s), 45.0-46.5 (br d), 38.5-39.5 (br s), 36.23 (d, J=25.5 Hz), 27.16 (s). m/z HRMS (EI) found [M]$^+$ 267.1269, C$_{14}$H$_{18}$O$_3$F$_1$ requires 267.1271. [α]D$^{20}$=+485.0 (c 1.0, CHCl$_3$). HPLC (Chiralpak IC column, 80:20 hexanes/isopropanol, 1 ml/min); t$_r$=9.8 min (minor), 11.0 min (major); 96% ee.

14.8 (R)-tert-butyl 4a-fluoro-5-oxo-3,4,4a,5-tetrahydroquinoline-1(2H)-carboxylate (3d)

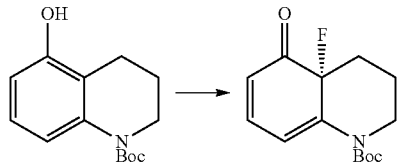 [SMILES: CC(C)(C)OC(=O)N1CCCc2c(O)cccc21 ; CC(C)(C)OC(=O)N1CCC[C@]2(F)C(=O)C=CC=C12]

Reaction carried out according to general procedure using tert-butyl 5-hydroxy-3,4-dihydroquinoline-1(2H)-carboxylate (1o) (62.5 mg, 0.25 mmol) for 48 h. Purification by column chromatography, eluting with a gradient of 0 to 2% Et$_2$O in CH$_2$Cl$_2$ yielded the title product contaminated with a fluorinated-phenol byproduct. This impurity was removed by a further purification on silica, eluting with 3:7 Et$_2$O: Hexane to give the title compound as a yellow oil which solidified on standing (19 mg, 0.709 mmol, 28%). $^1$H NMR (600 MHz, CDCl$_3$) δ 7.11 (dd, J=9.8, 7.0 Hz, 1H), 6.31 (d, J=6.8 Hz, 1H), 5.97 (d, J=9.8 Hz, 1H), 4.06 (dt, J=12.9, 5.1 Hz, 1H), 3.34 (t, J=10.2 Hz, 1H), 2.46-2.36 (m, 1H), 2.21-2.11 (m, 1H), 1.78-1.63 (m, 2H), 1.49 (s, 9H). $^{19}$F NMR (376 MHz, CDCl$_3$) δ −154.31 (br s). $^{13}$C NMR (151 MHz, CDCl$_3$) δ 195.15 (d, J=13.7 Hz), 153.23 (s), 144.55 (d, J=15.8 Hz), 143.28 (d, J=3.3 Hz), 120.81 (d, J=4.7 Hz), 113.68 (d, J=5.7 Hz), 87.69 (d, J=180.7 Hz), 81.74 (s), 45.52 (d, J=1.1 Hz), 32.17 (d, J=25.6 Hz), 28.17 (s), 20.30 (s). m/z HRMS (EI) found [M]$^+$ 267.1273, C$_{14}$H$_{18}$O$_3$F$_1$ requires 267.1271. [α]D$^{20}$=−520.3 (c 1.0, CHCl$_3$). HPLC (Chiralpak IC column, 85:15 hexanes/isopropanol, 1 ml/min); t$_r$=9.6 min (minor), 10.3 min (major); 87% ee.

14.9 (R)-6-fluoro-5,6-dimethylcyclohexa-2,4-dienone (3e)

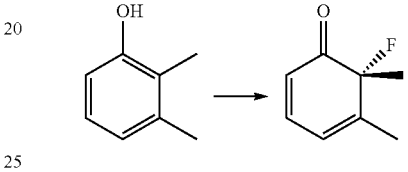

Reaction carried out according to general procedure using 2,3-dimethylphenol (30.5 mg, 0.25 mmol) for 46 h. Purification by column chromatography, eluting with 1:9 Et$_2$O: Hexane gave the title compound as a yellow oil (25 mg, 0.179 mmol, 71%). $^1$H NMR (600 MHz, CDCl$_3$) δ 6.91 (dd, J=9.9, 6.0 Hz, 1H), 5.99 (dd, J=9.9, 3.0 Hz, 1H), 5.94 (d, J=5.1 Hz, 1H), 2.00 (s, 3H), 1.56 (d, J=21.6 Hz, 3H). $^{19}$F NMR (376 MHz, CDCl$_3$) δ −168.90 (q, J=21.6 Hz). $^{13}$C NMR (151 MHz, CDCl$_3$) δ 200.61 (d, J=15.1 Hz), 151.65 (d, J=20.5 Hz), 141.87 (s), 123.09 (d, J=3.9 Hz), 119.16 (d, J=5.7 Hz), 95.66 (d, J=185.5 Hz), 24.47 (d, J=26.3 Hz), 17.05 (d, J=3.6 Hz). m/z HRMS (EI) found [M]$^+$ 140.0636, C8H9O1F1 requires 140.0637. [α]D$^{20}$=+466.0 (c 1.0, CHCl$_3$). HPLC (Chiralpak IC column, 98:02 hexanes/isopropanol, 1 ml/min); t$_r$=22.7 min (major), 27.2 min (minor); 88% ee.

14.10 (R)-4-bromo-6-fluoro-5,6-dimethylcyclohexa-2,4-dienone (3f)

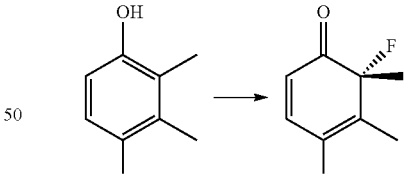

Reaction carried out according to general procedure using 2,3-dimethyl-4-bromo-phenol (50.0 mg, 0.25 mmol) for 48 h. Purification by column chromatography, eluting with 1:9 Et$_2$O:Hexane gave the title compound as a yellow oil (34 mg, 0.155 mmol, 62%). $^1$H NMR (400 MHz, CDCl$_3$) δ 7.06 (d, J=10.2 Hz, 1H), 5.99 (dd, J=10.2, 3.2 Hz, 1H), 2.10 (s, 3H), 1.58 (d, J=21.2 Hz, 3H). $^{19}$F NMR (376 MHz, CDCl$_3$) δ −161.74 (qd, J=21.2, 2.8 Hz). $^{13}$C NMR (151 MHz, CDCl$_3$) δ 197.79 (d, J=15.7 Hz), 147.75 (d, J=21.7 Hz), 146.23 (d, J=2.0 Hz), 123.56 (d, J=3.8 Hz), 114.05 (d, J=8.5 Hz), 95.81 (d, J=189.2 Hz), 24.26 (d, J=26.4 Hz), 17.69 (d, J=3.7 Hz). [α]D$^{20}$=+175.8 (c 1.0, CHCl$_3$). HPLC (Chiralpak IC column, 96:04 hexanes/isopropanol, 1 ml/min); t$_r$=9.2 min (major), 11.2 min (minor); 87% ee. m/z HRMS (EI) found [M]$^+$ 217.9748, $C_8H_8O_1F_1$ $^{79}Br_1$ requires 217.9743.

14.11 (R)-4-chloro-6-fluoro-5,6-dimethylcyclohexa-2,4-dienone (3g)

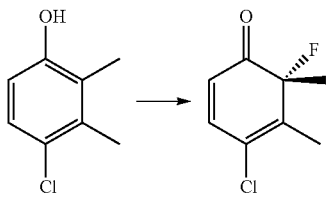

Reaction carried out according to general procedure using 2,3-dimethyl-4-chloro-phenol (39.0 mg, 0.25 mmol) for 48 h. Purification by column chromatography, eluting with 1:9 Et$_2$O:Hexane gave the title compound as a yellow oil (32 mg, 0.184 mmol, 74%). $^1$H NMR (400 MHz, CDCl$_3$) δ 6.93 (d, J=10.2 Hz, 1H), 6.06 (dd, J=10.2, 3.2 Hz, 1H), 2.08 (s, 3H), 1.57 (d, J=21.2 Hz, 3H). $^{19}$F NMR (376 MHz, CDCl$_3$) δ −162.46 (qd, J=21.2, 2.8 Hz). $^{13}$C NMR (151 MHz, CDCl$_3$) δ 197.83 (d, J=15.6 Hz), 144.38-144.19 (m, 2C), 123.97 (d, J=8.9 Hz), 123.57 (d, J=3.9 Hz), 95.06 (d, J=187.7 Hz), 24.29 (d, J=26.6 Hz), 14.57 (d, J=3.7 Hz). m/z HRMS (EI) found [M]$^+$ 174.0245, $C_8H_8O_1F_1$ $^{35}Cl$, requires 174.0248. [α]D$^{20}$=+250.0 (c 1.0, CHCl$_3$). HPLC (Chiralpak IC column, 96:04 hexanes/isopropanol, 1 ml/min); t$_r$=8.7 min (major), 10.5 min (minor); 90% ee.

14.12 (R)-6-fluoro-4-iodo-5,6-dimethylcyclohexa-2,4-dienone (3h)

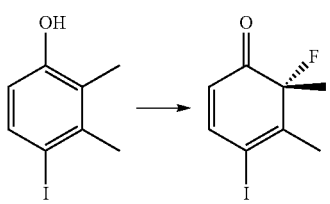

Reaction carried out according to general procedure using 2,3-dimethyl-4-iodo-phenol (62.0 mg, 0.25 mmol) for 48 h. Purification by column chromatography, eluting with 1:9 Et$_2$O:Hexane gave the title compound as a yellow solid (28 mg, 0.105 mmol, 42%). $^1$H NMR (400 MHz, CDCl$_3$) δ 7.22 (d, J=10.2 Hz, 1H), 5.85 (dd, J=10.1, 3.3 Hz, 1H), 2.14 (s, 3H), 1.56 (d, J=21.2 Hz, 3H). $^{19}$F NMR (376 MHz, CDCl$_3$) δ −160.81 (qd, J=21.2, 3.0 Hz). $^{13}$C NMR (151 MHz, CDCl$_3$) δ 198.01 (d, J=16.3 Hz), 154.19 (d, J=21.1 Hz), 150.51 (s), 123.55 (d, J=3.8 Hz), 96.20 (d, J=190.5 Hz), 89.40 (d, J=7.5 Hz), 24.33 (d, J=26.1 Hz), 23.28 (d, J=3.7 Hz). m/z HRMS (EI) found [M]$^+$ 265.9610, $C_8H_8O_1I_1F_1$ requires 265.9604. [α]D$^{20}$=+95.9 (c 1.0, CHCl$_3$). HPLC (Chiralpak IC column, 96:04 hexanes/isopropanol, 1 ml/min); t$_r$=10.0 min (major), 12.1 min (minor); 90% ee.

14.13 (R)-1-fluoro-6-methoxy-[1,1'-biphenyl]-2(1H)-one (3i)

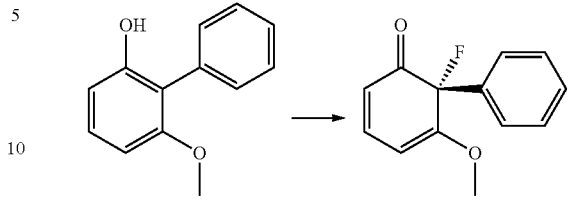

Reaction carried out according to general procedure using 6-methoxy-[1,1'-biphenyl]-2-ol (50.0 mg, 0.25 mmol) for 46 h. Purification by column chromatography, eluting with 1:1 Et$_2$O:Hexane gave the title compound as a yellow oil which solidified standing (38 mg, 0.174 mmol, 70%). $^1$H NMR (600 MHz, CDCl$_3$) δ 7.48 (d, J=7.0 Hz, 2H), 7.40-7.32 (m, 3H), 7.13 (t, J=8.4 Hz, 1H), 5.80 (d, J=9.9 Hz, 1H), 5.50 (d, J=7.0 Hz, 1H), 3.76 (s, 3H). $^{19}$F NMR (376 MHz, CDCl$_3$) δ −169.76 (s). $^{13}$C NMR (151 MHz, CDCl$_3$) δ 194.91 (d, J=16.9 Hz), 164.76 (d, J=15.3 Hz), 143.67 (s), 134.79 (d, J=24.9 Hz), 129.20 (s), 128.87 (s), 124.37 (d, J=7.4 Hz), 117.89 (d, J=3.3 Hz), 95.25 (d, J=3.4 Hz), 94.10 (d, J=191.6 Hz), 56.40 (s). [α]D$^{20}$=+267.2 (c 1.0, CHCl$_3$). m/z HRMS (EI) found [M]$^+$ 218.0740, $C_{13}H_{11}O_2F$ requires 218.0743. HPLC (Chiralpak IC column, 92:08 hexanes/isopropanol, 1 ml/min); t$_r$=26.4 min (major), 30.2 min (minor); 91% ee.

14.14 (1S,4R,4aS,8S,8aS,10S)-8,10-difluoro-8,10-diphenyl-4,4a,8,8a-tetrahydro-1,4-ethanonaphthalene-7,9(1H)-dione (4c)

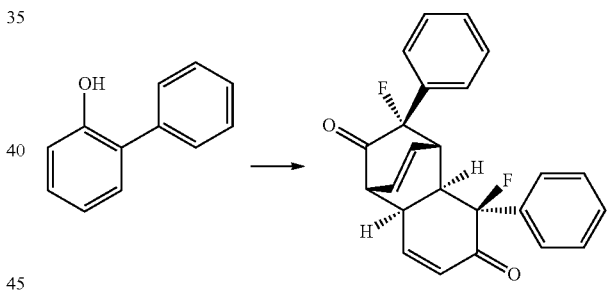

Reaction carried out according to general procedure using 2-phenylphenol (42.5 mg, 0.25 mmol) for 48 h. Purification by column chromatography, eluting with 1:1 Et$_2$O:Hexane gave the title compound as a white solid (26 mg, 0.0691 mmol, 55%). $^1$H NMR (400 MHz, CDCl$_3$) δ 7.51-7.44 (m, 2H), 7.43-7.31 (m, 8H), 6.53 (dd, J=10.2, 4.4 Hz, 1H), 6.35 (td, J=7.7, 7.3, 2.4 Hz, 1H), 6.13 (t, J=7.4 Hz, 1H), 6.02 (ddd, J=10.2, 4.3, 1.5 Hz, 1H), 4.07-4.00 (m, 2H), 3.85-3.77 (m, 1H), 3.59-3.54 (m, 1H). $^{13}$C NMR (151 MHz, CDCl$_3$) δ 203.20 (d, J=17.3 Hz), 192.57 (d, J=21.5 Hz), 144.58 (s), 138.99 (d, J=24.8 Hz), 137.22 (d, J=23.9 Hz), 134.60 (d, J=5.1 Hz), 129.78 (s), 129.30 (d, J=1.9 Hz), 129.16 (d, J=2.3 Hz), 128.74 (s, 2 overlapping peaks), 128.27 (s), 126.96 (d, J=5.7 Hz), 125.76 (d, J=7.0 Hz), 94.76 (d, J=195 Hz), 92.09 (d, J=191 Hz), 52.44 (s), 45.16 (dd, J=21.8, 15.0 Hz), 40.89 (d, J=3.3 Hz), 40.44 (dd, J=18.4, 4.5 Hz). $^{19}$F NMR (376 MHz, CDCl$_3$) δ −142.15 (s), −152.99 (s). m/z HRMS (EI) found [M]$^+$ 376.1282, $C_{24}H_{18}O_2F_2$ requires 376.1275. [α]D$^{20}$=−33.0 (c 1.0, CHCl$_3$). HPLC (Chiralpak IA column, 90:10 hexanes/isopropanol, 1 ml/min; t$_r$=15.5 min (major), 17.0 min (minor); 90% ee.

14.15 (1S,4R,4aS,8R,8aS,10R)-8,10-di(but-3-en-1-yl)-8,10-difluoro-4,4a,8,8a-tetrahydro-1,4-ethanonaphthalene-7,9(1H)-dione (4d)

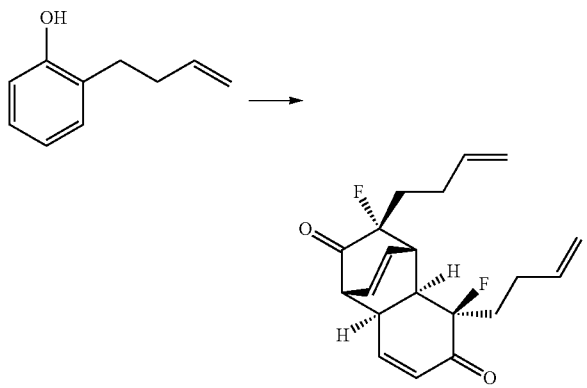

Reaction carried out according to general procedure using 2-homoallylphenol (37.0 mg, 0.25 mmol) for 48 h. Purification by column chromatography, eluting with 1:1 Et$_2$O:Hexane gave the title compound as a colourless oil (27 mg, 0.0813 mmol, 65%). $^1$H NMR (400 MHz, CDCl$_3$) δ 6.44 (dd, J=10.1, 4.1 Hz, 1H), 6.36 (t, J=7.4 Hz, 1H), 6.08 (ddd, J=10.1, 4.3, 1.6 Hz, 1H), 5.99 (t, J=7.2 Hz, 1H), 5.81-5.66 (m, 2H), 5.06-4.93 (m, 4H), 3.56 (d, J=6.5 Hz, 1H), 3.47-3.41 (m, 1H), 3.35-3.30 (m, 1H), 3.22 (d, J=8.5 Hz, 1H), 2.29-2.10 (m, 3H), 2.01-1.83 (m, 4H), 1.60 (dddd, J=32.2, 14.9, 11.0, 5.6 Hz, 1H). $^{19}$F NMR (376 MHz, CDCl$_3$) δ −162.15 (dd, J=32.5, 16.9 Hz), −170.22−−170.46 (m). $^{13}$C NMR (151 MHz, CDCl$_3$) δ 204.16 (d, J=16.6 Hz), 195.13 (d, J=18.6 Hz), 144.67 (s), 136.94 (s), 136.51 (s), 133.50 (d, J=5.7 Hz), 129.81 (d, J=1.3 Hz), 129.48 (s), 115.57 (s), 115.38 (s), 95.63 (d, J=195.6 Hz), 92.51 (d, J=192.3 Hz), 51.69 (s), 41.07 (dd, J=19.3, 12.5 Hz), 40.37 (dd, J=19.4, 5.4 Hz), 40.24 (d, J=24.6 Hz), 39.97 (d, J=4.2 Hz), 33.87 (d, J=25.0 Hz), 26.66 (s), 26.64 (s). m/z HRMS (EI) found [M]$^+$ 332.1579, C$_{20}$H$_{22}$O$_2$F$_2$ requires 332.1588. [α]D$^{20}$=+2.4 (c 1.0, CHCl$_3$). HPLC (Chiralpak IB column, 90:10 hexanes/isopropanol, 1 ml/min); t$_r$=7.8 min (major), 11.3 min (minor); 90% ee.

14.16 (1S,4R,4aS,8R,8aS,10R)-8,10-diallyl-8,10-difluoro-4,4a,8,8a-tetrahydro-1,4-ethanonaphthalene-7,9(1H)-dione (4e)

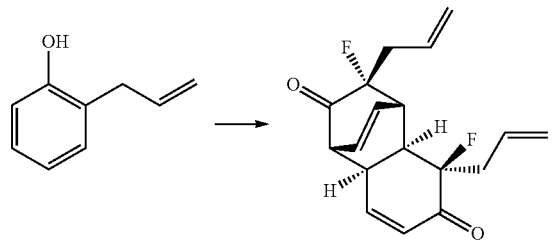

Reaction carried out according to general procedure using 2-allylphenol (33.5 mg, 0.25 mmol) for 48 h. Purification by column chromatography, eluting with 1:1 Et$_2$O:Hexane gave the title compound as a colourless oil (27 mg, 0.089 mmol, 71%). $^1$H NMR (400 MHz, CDCl$_3$) δ 6.45 (dd, J=10.1, 4.1 Hz, 1H), 6.36 (td, J=7.5, 6.9, 1.5 Hz, 1H), 6.06 (ddd, J=10.2, 4.2, 1.6 Hz, 1H), 5.98 (t, J=7.2 Hz, 1H), 5.80 (dddd, J=17.1, 10.1, 8.8, 5.7 Hz, 1H), 5.71 (ddt, J=17.3, 10.2, 7.3 Hz, 1H), 5.18 (t, J=10.8 Hz, 2H), 5.09 (dd, J=17.1, 5.1 Hz, 2H), 3.51 (d, J=6.6 Hz, 1H), 3.46-3.39 (m, 1H), 3.37-3.31 (m, 1H), 3.24 (dd, J=8.5, 1.4 Hz, 1H), 2.75-2.51 (m, 3H), 2.18 (ddd, J=35.4, 15.0, 8.7 Hz, 1H). $^{13}$C NMR (151 MHz, CDCl$_3$) δ 203.41 (d, J=16.5 Hz), 194.70 (d, J=18.0 Hz), 144.71 (s), 133.60 (d, J=5.8 Hz), 130.23 (d, J=3.3 Hz), 129.87-129.73 (m), 129.55 (d, J=3.4 Hz), 129.32 (s), 120.32 (s), 120.01 (s), 95.54 (d, J=196 Hz), 92.21 (d, J=193 Hz), 51.73 (s), 45.07 (d, J=24.2 Hz), 40.79 (dd, J=19.1, 12.6 Hz), 39.79 (d, J=4.2 Hz), 39.19 (dd, J=19.3, 5.4 Hz), 38.97 (d, J=24.5 Hz). $^{19}$F NMR (376 MHz, CDCl$_3$) δ −160.84 (dd, J=35.3, 15.4 Hz), −168.46 (t, J=24.3 Hz). m/z HRMS (EI) found [M]$^+$ 304.1276, C$_{18}$H$_{18}$O$_2$F$_2$ requires 304.1275. [α]D$^{20}$=−18.1 (c 1.0, CHCl3). HPLC (Chiralpak IB column, 90:10 hexanes/isopropanol, 1 ml/min); t$_r$=10.3 min (major), 11.8 min (minor); 87% ee.

14.17 (1S,4R,4aS,8R,8aS,10R)-8,10-difluoro-8,10-diisopropyl-4,4a,8,8a-tetrahydro-1,4-ethanonaphthalene-7,9(1H)-dione (4f)

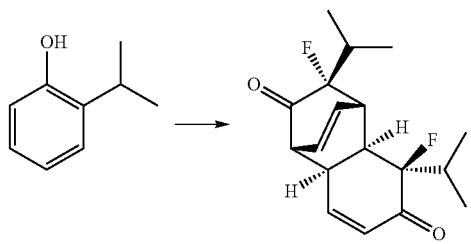

Reaction carried out according to general procedure using 2-isopropylphenol (34 mg, 0.25 mmol) for 48 h. Purification by column chromatography, eluting with 1:1 Et$_2$O:Hexane gave the title compound as a colourless oil (37 mg, 0.120 mmol, 96%). $^1$H NMR (400 MHz, CDCl$_3$) δ 6.42 (dd, J=10.1, 3.8 Hz, 1H), 6.36 (t, J=7.1 Hz, 1H), 6.08 (ddd, J=10.0, 4.2, 1.4 Hz, 1H), 5.97-5.89 (m, 1H), 3.52-3.43 (m, 1H), 3.43-3.25 (m, 3H), 2.12-1.86 (m, 2H), 1.04 (d, J=6.8 Hz, 3H), 1.01 (d, J=6.9 Hz, 3H), 0.87 (d, J=7.0 Hz, 3H), 0.82 (d, J=6.9 Hz, 3H). $^{19}$F NMR (376 MHz, CDCl$_3$) δ −170.29 (d, J=25.4 Hz), −181.56 (d, J=26.5 Hz). $^{13}$C NMR (151 MHz, CDCl$_3$) δ 204.74 (d, J=16.5 Hz), 195.97 (d, J=18.9 Hz), 144.79 (s), 133.22 (d, J=6.1 Hz), 130.24 (s), 128.41 (s), 97.66 (d, J=198 Hz), 95.17 (d, J=195 Hz), 52.25 (s), 41.37 (d, J=4.2 Hz), 40.68 (dd, J=19.6, 13.1 Hz), 37.43 (dd, J=19.4, 5.6 Hz), 36.16 (d, J=24.4 Hz), 32.22 (d, J=24.8 Hz), 17.35 (d, J=4.4 Hz), 16.75 (d, J=2.5 Hz), 16.17 (d, J=5.6 Hz), 15.58 (d, J=6.8 Hz). m/z HRMS (EI) found [M+H]$^+$ 309.1659, C$_{18}$H$_{23}$O$_2$F$_2$ requires 309.1666. [α]D$^{20}$=+75.6 (c 1.0, CHCl3). HPLC (Chiralpak IC column, 85:15 hexanes/isopropanol, 1 ml/min); t$_r$=7.3 min (major), 8.4 min (minor); 91% ee.

14.18 (1S,4S,4aS,8R,8aS,10R)-8,10-dicyclohexyl-8,10-difluoro-3,5-dimethyl-4,4a,8,8a-tetrahydro-1,4-ethanonaphthalene-7,9(1H)-dione (4g)

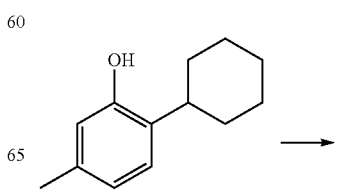

-continued

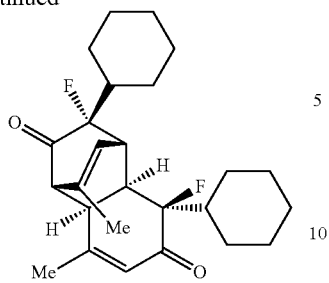

Reaction carried out according to general procedure using 2-cyclohexyl-5-ethylphenol (47.5 mg, 0.25 mmol) for 48 h. Purification by column chromatography, eluting with 1:4:5 CHCl$_3$:Et$_2$O:Hexane gave the title compound as a white solid (39 mg, 0.0938 mmol, 75%). $^1$H NMR (400 MHz, CDCl$_3$) δ 5.92 (d, J=3.9 Hz, 1H), 5.89-5.84 (m, 1H), 3.39-3.32 (m, 1H), 3.25-3.13 (m, 3H), 1.97 (d, J=1.0 Hz, 3H), 1.94-0.91 (m, 25H). $^{19}$F NMR (376 MHz, CDCl$_3$) δ −161.22 (d, J=21.4 Hz), −178.12 (d, J=24.7 Hz). $^{13}$C NMR (151 MHz, CDCl$_3$) δ 204.53 (d, J=16.9 Hz), 195.29 (d, J=19.5 Hz), 154.52 (s), 136.36 (s), 127.45 (s), 125.69 (d, J=6.8 Hz), 97.55 (d, J=196.1 Hz), 95.12 (d, J=190.5 Hz), 56.96 (s), 46.14 (d, J=23.8 Hz), 45.36 (d, J=4.2 Hz), 42.05 (d, J=24.2 Hz), 39.54 (dd, J=19.6, 14.0 Hz), 36.16 (dd, J=19.1, 5.5 Hz), 27.93 (d, J=4.9 Hz), 27.06 (d, J=2.2 Hz), 26.65 (s), 26.31 (s), 26.22 (s), 26.19 (s), 26.13 (s), 26.02 (s), 25.97 (s), 25.50 (d, J=6.0 Hz), 21.98 (s), 21.41 (s). m/z HRMS (EI) found [M]$^+$ 416.2532, C$_{26}$H$_{34}$O$_2$F$_2$ requires 416.2527. [α]$D^{20}$=+73.1 (c 1.0, CHCl3). HPLC (Chiralpak IC column, 90:10 hexanes/isopropanol, 1 ml/min); t$_r$=6.5 min (major), 9.0 min (minor); 79% ee.

14.19 (1R,4R,4aS,8R,8aR,10R)-8,10-diallyl-8,10-difluoro-2,4a-dimethyl-4,4a,8,8a-tetrahydro-1,4-ethanonaphthalene-7,9(1H)-dione (4h)

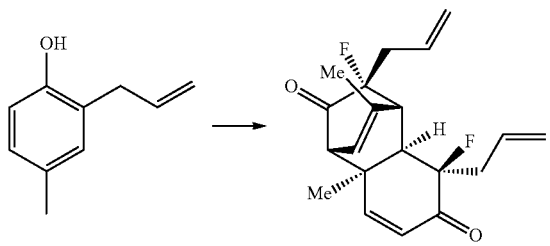 [SMILES: C=CCc1cc(C)ccc1O ; C=CC[C@]1(F)C(=O)C=C[C@]2(C)[C@H]1[C@@H]1C(C)=C[C@H]2C(=O)[C@@]1(F)CC=C]

Reaction carried out according to general procedure using 2-allyl-4-methylphenol (37.0 mg, 0.25 mmol) for 48 h. Purification by column chromatography, eluting with 1:1 Et$_2$O:Hexane gave the title compound as a colourless oil (21 mg, 0.0632 mmol, 51%). $^1$H NMR (400 MHz, CDCl$_3$) δ 6.18 (d, J=10.2 Hz, 1H), 5.97 (dd, J=10.2, 4.2 Hz, 1H), 5.86 (dddd, J=17.0, 10.2, 8.6, 5.6 Hz, 1H), 5.71 (ddt, J=17.3, 10.2, 7.1 Hz, 1H), 5.59 (d, J=6.3 Hz, 1H), 5.26-5.04 (m, 4H), 3.30 (t, J=1.7 Hz, 1H), 2.88 (d, J=6.4 Hz, 1H), 2.84 (s, 1H), 2.83-2.73 (m, 1H), 2.71-2.50 (m, 2H), 2.14 (ddd, J=36.0, 15.2, 8.6 Hz, 1H), 1.80 (d, J=1.4 Hz, 3H), 1.41 (s, 3H). $^{19}$F NMR (376 MHz, CDCl$_3$) δ −157.72 (dd, J=36.0, 13.3 Hz), −168.43 (t, J=25.1 Hz). $^{13}$C NMR (151 MHz, CDCl$_3$) δ 202.64 (d, J=17.1 Hz), 194.25 (d, J=18.2 Hz), 150.51 (s), 143.88 (d, J=5.4 Hz), 130.71 (d, J=3.9 Hz), 129.45 (d, J=3.1 Hz), 127.24 (s), 123.68 (s), 120.37 (s), 119.99 (s), 95.53 (d, J=196.2 Hz), 91.17 (d, J=191.5 Hz), 58.58 (s), 45.55-45.17 (m, 3C overlapping), 44.79 (d, J=3.9 Hz), 38.37 (d, J=24.3 Hz), 25.70 (s), 20.75 (s). m/z HRMS (EI) found [M]$^+$ 332.1589, C$_{20}$H$_{22}$O$_2$F$_2$ requires 332.1588. [α]$D^{20}$=−51.1 (c 1.0, CHCl3). HPLC (Chiralpak IB column, 92:08 hexanes/isopropanol, 1 ml/min); t$_r$=7.3 min (major), 9.6 min (minor); 92% ee.

14.20 (1R,4R,4aS,8R,8aR,10R)-8,10-dibenzyl-8,10-difluoro-2,4a-dimethyl-4,4a,8,8a-tetrahydro-1,4-ethanonaphthalene-7,9(1H)-dione (4i)

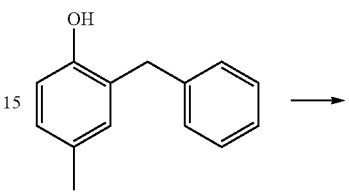

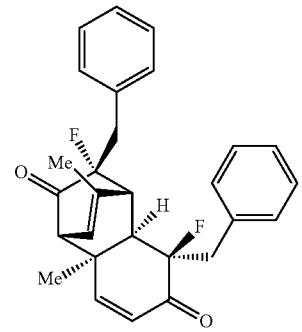

Reaction carried out according to general procedure using 2-benzyl-4-methylphenol (49.5 mg, 0.25 mmol) for 48 h. Purification by column chromatography, eluting with 1:1 Et$_2$O:Hexane gave the title compound as a colourless oil (36 mg, 0.0833 mmol, 67%). $^1$H NMR (600 MHz, CDCl$_3$) δ 7.37-7.28 (m, 3H), 7.28-7.20 (m, 5H), 7.06 (d, J=6.7 Hz, 2H), 6.25 (d, J=10.1 Hz, 1H), 5.96 (dd, J=10.1, 4.2 Hz, 1H), 5.66 (d, J=5.9 Hz, 1H), 3.41 (t, J=14.2 Hz, 1H), 3.23-3.06 (m, 3H), 2.99 (d, J=6.3 Hz, 1H), 2.83 (s, 1H), 2.58 (dd, J=37.5, 15.0 Hz, 1H), 1.84 (s, 3H), 1.52 (s, 3H). $^{19}$F NMR (376 MHz, CDCl$_3$) δ −154.22 (dd, J=37.5, 13.3 Hz), −166.03 (dd, J=32.2, 20.4 Hz). $^{13}$C NMR (151 MHz, CDCl$_3$) δ 202.47 (d, J=17.3 Hz), 193.54 (d, J=18.7 Hz), 150.11 (s), 143.97 (d, J=5.3 Hz), 133.94 (s), 133.06 (s), 130.72 (d, J=1.5 Hz), 129.87 (d, J=1.2 Hz), 128.39 (s), 128.36 (s), 127.66 (s), 127.46 (s), 127.22 (s), 124.15 (s), 96.15 (d, J=197.5 Hz), 91.19 (d, J=190.5 Hz), 58.76 (s), 47.56 (d, J=23.7 Hz), 46.67 (dd, J=18.6, 4.9 Hz), 45.17 (dd, J=18.6, 12.6 Hz), 44.80 (d, J=3.7 Hz), 39.47 (d, J=23.5 Hz), 25.95 (s), 20.86 (s). m/z HRMS (EI) found [M]$^+$ 432.1904, C$_{28}$H$_{26}$O$_2$F$_2$ requires 432.1901. [α]$D^{20}$=−5.4 (c 1.0, CDCl$_3$). HPLC (Chiralpak IC column, 90:10 hexanes/isopropanol, 1 ml/min); t$_r$=12.3 min (minor), 24.2 min (major); 90% ee.

14.21 (1S,4R,4aS,8R,8aS,10R)-8,10-bis(3-((tert-butyldimethylsilyl)oxy)propyl)-8,10-difluoro-4,4a,8,8a-tetrahydro-1,4-ethanonaphthalene-7,9(1H)-dione (4j)

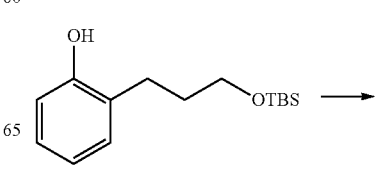

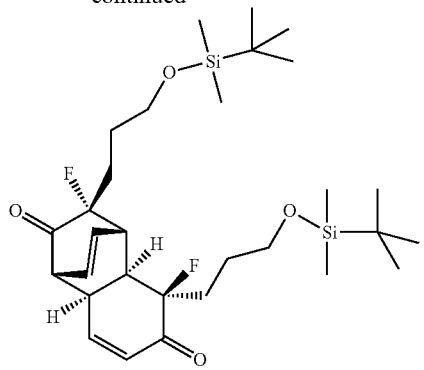

Reaction carried out according to general procedure using 2-(3-((tertbutyldimethylsilyl)oxy)propyl)phenol (66.5 mg, 0.25 mmol) for 48 h. Purification by column chromatography, eluting with 3:7 Et$_2$O:Hexane gave the title compound as a white solid (55 mg, 0.0968 mmol, 77%). $^1$H NMR (400 MHz, CDCl$_3$) δ 6.42 (dd, J=10.1, 4.1 Hz, 1H), 6.35 (t, J=6.6 Hz, 1H), 6.06 (ddd, J=10.1, 4.2, 1.3 Hz, 1H), 5.97 (t, J=7.0 Hz, 1H), 3.66-3.48 (m, 5H), 3.45-3.40 (m, 1H), 3.31 (d, J=5.7 Hz, 1H), 3.21 (d, J=8.4 Hz, 1H), 2.09-1.77 (m, 3H), 1.72-1.51 (m, 4H), 1.32 (ddt, J=18.5, 12.1, 5.5 Hz, 1H), 0.92-0.79 (m, 18H), 0.07--0.07 (m, 12H). $^{19}$F NMR (376 MHz, CDCl$_3$) δ -162.15--162.37 (m), -170.31 (dd, J=33.1, 17.5 Hz). $^{13}$C NMR (151 MHz, CDCl$_3$) δ 204.49 (d, J=15.9 Hz), 195.48 (d, J=18.9 Hz), 144.63 (s), 133.58 (d, J=5.6 Hz), 129.74 (s), 129.33 (s), 96.06 (d, J=195.1 Hz), 92.91 (d, J=192.1 Hz), 62.40 (s), 62.07 (s), 51.73 (s), 41.12 (dd, J=19.4, 12.3 Hz), 40.43 (dd, J=19.5, 5.2 Hz), 40.08 (d, J=4.2 Hz), 37.70 (d, J=24.6 Hz), 31.32 (d, J=25.1 Hz), 25.84 (s, 3 overlapping carbons), 18.19 (s), -5.38 (s), -5.40 (s). m/z HRMS (EI) found [M-CH$_3$]$^+$ 553.2974, C$_{29}$H$_{47}$O$_4$F$_2$Si$_2$ requires 553.2970. [α]D$^{20}$=+1.5 (c 1.0, CHCl3). HPLC (Chiralpak IC column, 97:03 hexanes/isopropanol, 1 ml/min); t$_r$=6.9 min (major), 8.3 min (minor); 91% ee.

14.22 (3aS,4S,7R,7aR,9R)-9-benzyl-9-fluoro-3a,4,7,7a-tetrahydro-3H-4,7-ethanoinden-8-one (5a)

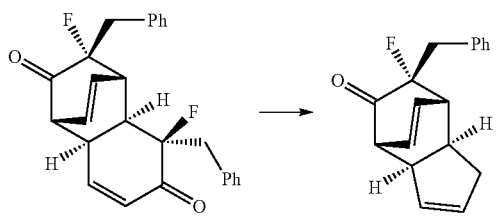 [SMILES: O=C1C=C[C@@H]2[C@@H]([C@@H]3C=C[C@H]2C(=O)[C@@]3(F)Cc2ccccc2)[C@]1(F)Cc1ccccc1 ; O=C1[C@@H]2C=C[C@@H]([C@H]3CC=C[C@H]32)[C@]1(F)Cc1ccccc1]

According to the procedure of Porco and co-workers, a vial containing 4b (15 mg, 0.0371 mmol) and dicyclopentadiene (24 mg, 0.181 mmol) in mesitylene (1 ml) was heated at 150° C. for 14 h. After this time, the reaction mixture was purified directly by chromatography, eluting with hexane then 1:9 Et$_2$O:Hexane. The resulting compound was contaminated with a less polar (non-fluorine containing) impurity which required a further two purifications eluting with 1:9 Et$_2$O:Hexane to remove completely to give the clean title compound as a colourless oil (12 mg, 0.0448 mmol, 60%). $^1$H NMR (600 MHz, CDCl$_3$) δ 7.37-7.32 (m, 2H), 7.32-7.28 (m, 1H), 7.23 (d, J=7.6 Hz, 2H), 6.29-6.24 (m, 1H), 6.12 (t, J=7.1 Hz, 1H), 5.68 (dd, J=5.5, 2.2 Hz, 1H), 5.43 (dd, J=5.4, 2.3 Hz, 1H), 3.36-3.26 (m, 3H), 2.94 (ddd, J=13.3, 9.0, 3.9 Hz, 1H), 2.90 (d, J=5.3 Hz, 1H), 2.65 (dd, J=39.2, 14.8 Hz, 1H), 2.52-2.44 (m, 1H), 1.89 (dtt, J=17.3, 4.4, 2.4 Hz, 1H). $^{19}$F NMR (376 MHz, CDCl$_3$) δ -157.72 (dd, J=39.1, 14.8 Hz). $^{13}$C NMR (151 MHz, CDCl$_3$) δ 205.57 (d, J=15.4 Hz), 135.13 (s), 133.62 (s), 131.96 (d, J=7.3 Hz), 130.28 (d, J=1.1 Hz), 129.50 (s), 129.35 (s), 128.33 (s), 127.01 (s), 93.45-92.66 (d, J=191.6 Hz), 51.38 (s), 50.54 (s), 44.42 (d, J=20.2 Hz), 40.03 (d, J=23.9 Hz), 38.37 (s), 32.76 (d, J=4.6 Hz). m/z HRMS (EI) found [M]$^+$ 268.1266, C$_{18}$H$_{17}$OF requires 268.1263. [α]D$^{20}$=+18.3 (c 1.0, CHCl3). HPLC (Chiralpak IA column, 98:02 hexanes/isopropanol, 1 ml/min); t$_r$=7.2 min (minor), 8.6 min (major); 96% ee.

The relative stereochemistry of this compound has been assigned using COSY, 1D-NOESY and 1D-F-H HOESY19 experiments. After assigning the protons using the COSY, a 1D NOE experiment and a 1D-F-H HOESY19 experiment were used to confirm the stereochemistry as shown. The outcome is in agreement with that observed by Porco and coworkers in that the dienophile reacts from the heteroatom-bearing (in our case F, rather than OH) face of the diene, in an endo manner. (Dong, S.; Hamel, E.; Bai, R.; Covell, D. G.; Beutler, J. A.; Porco, J. A. Angew. Chem., Int. Ed. 2009, 48, 1494).

14.23 (3aS,4S,7R,7aS,9R)-9-benzyl-9-fluoro-2-phenyl-3a,4,7,7a-tetrahydro-1H-4,7-ethanoisoindole-1,3,8(2H)-trione (5b)

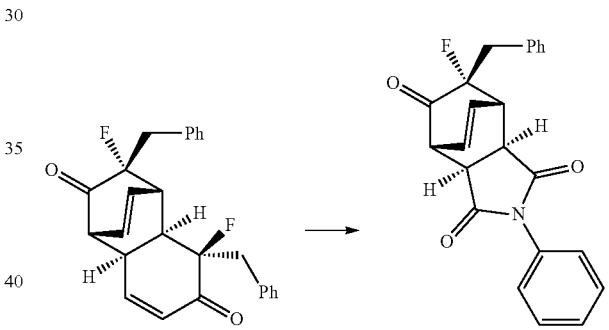

According to the procedure of Porco and co-workers, a vial containing 4b (20 mg, 0.0495 mmol) and N-Phenylmaleimide (43 mg, 0.248 mmol) in mesitylene (0.5 ml) was heated at 150° C. for 14 h. After this time, the reaction mixture was purified directly by chromatography, eluting with toluene then 1:19 Et$_2$O:Toluene. The resulting compound was contaminated with a less polar (non-fluorine containing) impurity which required a further purification eluting with CH$_2$Cl$_2$ to remove to give the clean title compound as a white solid (28 mg, 0.0747 mmol, 75%). $^1$H NMR (600 MHz, CDCl$_3$) δ 7.45 (t, J=7.8 Hz, 2H), 7.39 (t, J=7.3 Hz, 1H), 7.37-7.31 (m, 3H), 7.20 (d, J=7.2 Hz, 2H), 7.16 (d, J=7.4 Hz, 2H), 6.43-6.38 (m, 1H), 6.32 (t, J=7.1 Hz, 1H), 3.93-3.89 (m, 1H), 3.61-3.57 (m, 1H), 3.54 (dd, J=8.4, 3.2 Hz, 1H), 3.50 (dd, J=8.4, 3.0 Hz, 1H), 3.40 (t, J=14.9 Hz, 1H), 2.71 (dd, J=37.1, 14.9 Hz, 1H). $^{19}$F NMR (376 MHz, CDCl$_3$) δ -154.45 (dd, J=37.0, 14.6 Hz). $^{13}$C NMR (151 MHz, CDCl$_3$) δ 199.85 (d, J=16.4 Hz), 175.97 (s), 174.40 (s), 133.60 (d, J=1.1 Hz), 132.93 (d, J=6.6 Hz), 131.42 (s), 130.18 (s), 129.18 (s), 128.96 (s), 128.70 (s), 128.20 (s), 127.63 (s), 126.25 (s), 90.66 (d, J=192.8 Hz), 47.91 (s), 41.55-41.17 (m, two overlapping carbons), 39.70 (d, J=23.6 Hz), 38.66 (d, J=6.2 Hz). m/z HRMS (EI) found [M]$^1$375.1276, C$_{23}$H$_{18}$O$_3$F requires 375.1271. [α]D$^{20}$=+

34.5 (c 1. 0, CHCl3). HPLC (Chiralpak IA column, 85:15 hexanes/isopropanol, 1 ml/min); $t_r$=18.8 min (minor), 20.7 min (major); 97% ee.

The relative stereochemistry of this compound has been assigned using COSY and 1D F-H HOESY[19] experiments. After assigning the protons using the COSY, a 1D-F-H HOESY[19] experiment was used to confirm the stereochemistry as shown. The outcome is in agreement with that observed by Porco and co-workers in that the dienophile reacts from the heteroatom-bearing (in our case F, rather than OH) face of the diene, in an endo manner. (Dong, S.; Hamel, E.; Bai, R.; Covell, D. G.; Beutler, J. A.; Porco, J. A. *Angew. Chem., Int. Ed.* 2009, 48, 1494).

14.24 (R)-4a-fluoro-8,8-dimethyl-5,6,7,8-tetrahydronaphthalen-2(4aH)-one (2e)

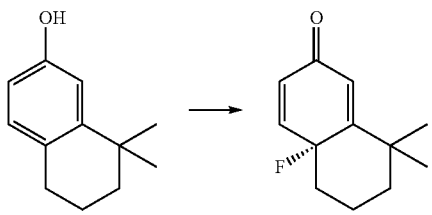

Reaction carried out according to general procedure using 8,8-dimethyl-5,6,7,8-tetrahydronaphthalen-2-ol (1u) (44.0 mg, 0.25 mmol) for 46 h. Purification by column chromatography, eluting with 1:1 $CH_2Cl_2$:Hexane gave the title compound as a white solid (14 mg, 0.0722 mmol, 29%). $^1$H NMR (600 MHz, CDCl$_3$) δ 6.76 (dd, J=9.9, 7.2 Hz, 1H), 6.19 (d, J=10.0 Hz, 1H), 6.14 (s, 1H), 2.31-2.22 (m, 1H), 2.07 (qt, J=13.7, 3.5 Hz, 1H), 1.74-1.63 (m, 2H), 1.45 (dtd, J=40.6, 13.8, 4.7 Hz, 1H), 1.35 (td, J=13.6, 3.8 Hz, 1H), 1.29 (d, J=2.8 Hz, 3H), 1.20 (s, 3H). $^{19}$F NMR (376 MHz, CDCl$_3$) δ -147.11 (d, J=40.4 Hz). $^{13}$C NMR (151 MHz, CDCl$_3$) δ 186.42 (d, J=5.3 Hz), 162.49 (d, J=15.1 Hz), 147.17 (d, J=22.5 Hz), 128.19 (d, J=7.9 Hz), 123.99 (d, J=5.5 Hz), 88.43 (d, J=164.7 Hz), 40.92 (s), 38.01 (d, J=25.7 Hz), 37.98 (d, J=1.4 Hz), 29.96 (s), 25.58 (d, J=7.5 Hz), 17.31 (d, J=1.4 Hz). m/z HRMS (EI) found [M]$^+$ 194.1111, $C^{12}H^{15}O^1F^1$ requires 194.1107. $[α]D^{20}$=-75.0 (c 1.0, CHCl3). HPLC (Chiralpak IB column, 99:01 hexanes/isopropanol, 0.5 ml/min); $t_r$=14.6 min (minor), 15.5 min (major); 86% ee.

14.25 (R)-7a-fluoro-3,3-dimethyl-2,3-dihydro-1H-inden-5(7aH)-one (2f)

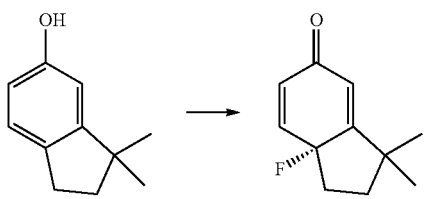

Reaction carried out according to general procedure using 3,3-dimethyl-2,3-dihydro-1H-inden-5-ol (40.5 mg, 0.25 mmol) for 46 h. Purification by column chromatography, eluting with 70% $CH_2Cl_2$ in Hexane gave the title compound as a colourless oil (18 mg, 0.10 mmol, 40%). $^1$H NMR (600 MHz, CDCl$_3$) δ 6.93 (dd, J=9.9, 4.3 Hz, 1H), 6.21 (ddd, J=9.9, 3.0, 1.6 Hz, 1H), 6.05 (t, J=1.8 Hz, 1H), 2.28 (td, J=14.0, 7.0 Hz, 1H), 2.14 (td, J=12.1, 7.2 Hz, 1H), 1.83 (dd, J=12.5, 8.7 Hz, 1H), 1.74 (dddd, J=41.0, 14.2, 11.5, 8.7 Hz, 1H), 1.33 (s, 3H), 1.22 (s, 3H). $^{19}$F NMR (376 MHz, CDCl$_3$) δ -140.40 (dd, J=40.7, 14.0 Hz). $^{13}$C NMR (151 MHz, CDCl$_3$) δ 186.40 (d, J=6.5 Hz), 170.53 (d, J=10.7 Hz), 140.74 (d, J=18.8 Hz), 130.87 (d, J=7.5 Hz), 122.72 (d, J=5.1 Hz), 93.98 (d, J=160.6 Hz), 40.42 (s), 38.51 (s), 33.73 (d, J=26.4 Hz), 29.57 (s), 29.40 (s). $[α]D^{20}$=-67.6 (c 1.0, CHCl3). m/z HRMS (EI) found [M]$^+$ 180.0949, $C_{11}H_{13}O_1F_1$ requires 180.0950. HPLC (Chiralpak IB column, 999:001 hexanes/isopropanol, 1.0 ml/min); $t_r$=9.3 min (minor), 9.8 min (major); 85% ee.

14.26 (R)-4a-fluoro-8,8-diphenyl-5,6,7,8-tetrahydronaphthalen-2(4aH)-one (2g)

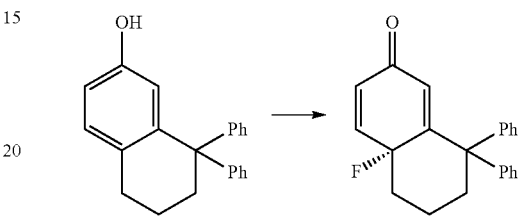

Reaction carried out according to general procedure using 8,8-diphenyl-5,6,7,8-tetrahydronaphthalen-2-ol (1w) (75.0 mg, 0.25 mmol) for 90 h. Purification by column chromatography, eluting with 3:17 $Et_2O$:Hexane gave the title compound as a white solid (10 mg, 0.0314 mmol, 13%). $^1$H NMR (600 MHz, CDCl$_3$) δ 7.42-7.30 (m, 5H), 7.24-7.16 (m, 3H), 6.89 (d, J=7.6 Hz, 2H), 6.76 (dd, J=9.9, 6.7 Hz, 1H), 6.26 (d, J=10.0 Hz, 1H), 5.93 (s, 1H), 2.87 (d, J=14.4 Hz, 1H), 2.37 (td, J=14.0, 3.1 Hz, 1H), 2.33-2.26 (m, 1H), 2.10 (q, J=13.7 Hz, 1H), 1.87-1.71 (m, 2H). $^{19}$F NMR (376 MHz, CDCl$_3$) δ -139.20 (d, J=39.8 Hz). $^{13}$C NMR (151 MHz, CDCl$_3$) δ 186.05 (d, J=4.5 Hz), 159.75 (d, J=14.1 Hz), 147.25 (d, J=21.3 Hz), 145.57 (s), 140.12 (s), 130.13 (d, J=4.2 Hz), 128.97 (s), 128.55-128.41 (m, 2 peaks overlapping), 128.05 (s), 128.02 (s), 126.82 (s), 126.78 (s), 87.63 (d, J=167.5 Hz), 56.00 (d, J=1.3 Hz), 38.41 (d, J=26.5 Hz), 37.35 (s), 17.56 (d, J=1.6 Hz). m/z HRMS (EI) found [M]$^+$ 318.1422, $C_{22}H_{19}O_1F_1$ requires 318.1420. $[α]D^{20}$=-166.5 (c 0.67, CHCl3). HPLC (Chiralpak IA column, 98:02 hexanes/isopropanol, 1 ml/min); $t_r$=8.9 min (major), 10.0 min (minor); 86% ee.

14.27 (1S,4R,4aS,8S,8aS,10S)-8,10-bis(((tert-butyldimethylsilyl)oxy)methyl)-8,10-difluoro-4,4a,8,8a-tetrahydro-1,4-ethanonaphthalene-7,9(1H)-dione (6a)

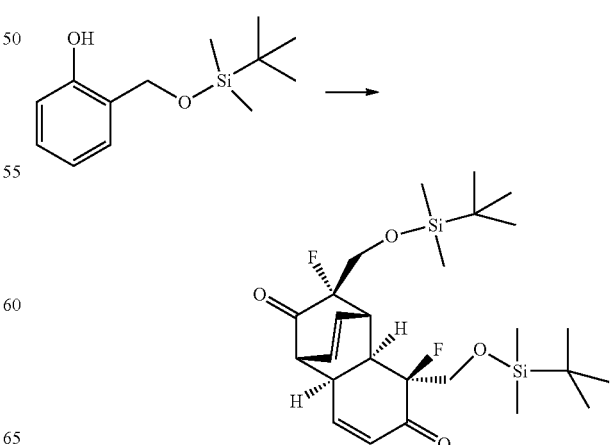

Reaction carried out according to general procedure using 2-(((tertbutyldimethylsilyl)oxy)methyl)phenol 6 (59.5 mg, 0.25 mmol) for 48 h. Purification by column chromatography, eluting with 1:9 Et$_2$O:Hexane gave the recovered starting material as an oil (35 mg, 0.147 mmol, 59%) and further elution with 4:6 Et$_2$O:Hexane gave title compound as a white solid (22 mg, 0.043 mmol, 34% yield, 83% yield based on recovered starting material). $^1$H NMR (600 MHz, CDCl$_3$) δ 6.46 (dd, J=10.2, 4.2 Hz, 1H), 6.42 (t, J=6.5 Hz, 1H), 6.10 (ddd, J=10.2, 4.0, 1.3 Hz, 1H), 5.98 (t, J=7.2 Hz, 1H), 3.92-3.74 (m, 4H), 3.55 (dd, J=34.1, 12.1 Hz, 1H), 3.42-3.37 (m, 1H), 3.30 (d, J=5.9 Hz, 1H), 3.27 (d, J=8.7 Hz, 1H), 0.87 (s, 9H), 0.85 (s, 9H), 0.04 (d, J=2.6 Hz, 6H), 0.03 (d, J=2.0 Hz, 6H). $^{19}$F NMR (376 MHz, CDCl$_3$) δ −165.27 (dd, J=34.1, 16.2 Hz), −172.61 (t, J=23.1 Hz). $^{13}$C NMR (151 MHz, CDCl$_3$) δ 202.63 (d, J=16.1 Hz), 193.56 (d, J=18.3 Hz), 144.77 (s), 134.49 (d, J=6.2 Hz), 130.12 (d, J=1.3 Hz), 128.63 (s), 96.48 (d, J=196.5 Hz), 93.07 (d, J=194.9 Hz), 69.10 (d, J=27.4 Hz), 63.79 (d, J=26.1 Hz), 51.81 (s), 39.81 (d, J=3.8 Hz), 38.64 (dd, J=19.5, 13.3 Hz), 35.56 (dd, J=19.0, 5.1 Hz), 25.70 (s), 25.62 (s), 18.21 (s), 18.13 (s), −5.46 (s), −5.51 (s), −5.59 (s), −5.64 (s). m/z HRMS (EI) found [M-C(CH$_3$)$_3$]+455.1886, C$_{22}$H$_{33}$O$_4$F$_2$Si$_2$ requires 455.1885. [α]D$^{20}$=+7.1 (c 1.0, CHCl3). HPLC (Chiralpak IA column, 98:02 hexanes/isopropanol, 1 ml/min); t$_r$=6.8 min (major), 8.7 min (minor); 92% ee.

14.28 ((1S,4R,4aS,8S,8aS,10S)-8,10-difluoro-7,9-dioxo-1,4,4a,7,8,8a-hexahydro-1,4-ethanonaphthalene-8,10-diyl)bis(methylene)dibenzoate (7)

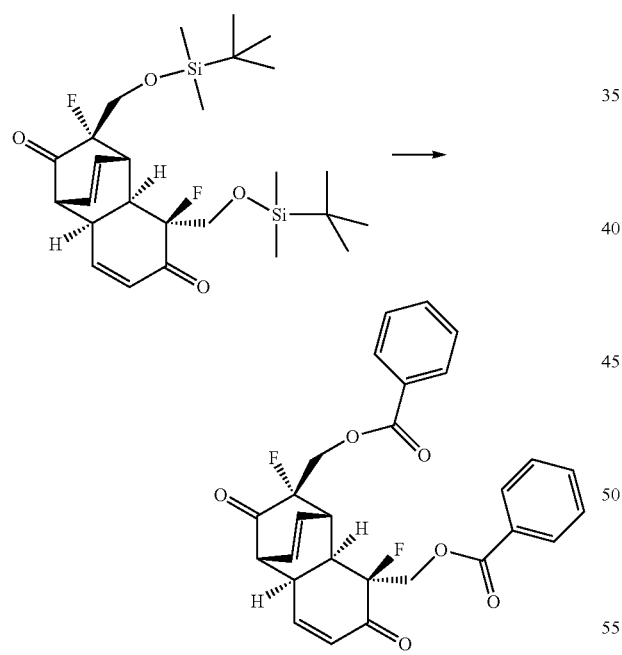

Adapted from a literature procedure (Kim, S.; Lee, W. J. Synth. Commun. 1986, 16, 659), to a stirred solution of 6a (21 mg, 0.041 mmol) in anhydrous acetonitrile was added ZnCl$_2$ (2.2 mg, 0.0164 mmol) and benzoyl chloride (60 mg, 0.42 mmol) and the reaction was stirred at room temperature. After 90 mins, TLC indicated the reaction was not complete so further ZnCl$_2$ (10 mg, 0.0735 mmol) and benzoyl chloride (60 mg, 0.42 mmol) were added. After 30 mins, further benzoyl chloride (60 mg, 0.42 mmol) was added. After a further 30 mins at rt, TLC indicated complete conversion to product. The solvent was removed in vacuo and the crude residue purified by flash column chromatography (eluting with 7:3 Et$_2$O:Hexane). The product was then taken up in CH$_2$Cl$_2$ and washed with satd sodium bicarbonate solution to remove benzoic acid impurity. Evaporation gave the title compound as a white solid (14 mg, 0.285 mmol, 69%). $^1$H NMR (600 MHz, CDCl$_3$) δ 8.06 (d, J=7.2 Hz, 2H), 7.97 (d, J=7.2 Hz, 2H), 7.64-7.54 (m, 2H), 7.47 (t, J=7.8 Hz, 2H), 7.44 (t, J=7.8 Hz, 2H), 6.54 (dd, J=10.2, 4.2 Hz, 1H), 6.47 (t, J=7.3 Hz, 1H), 6.18 (ddd, J=10.2, 4.3, 1.5 Hz, 1H), 6.14 (t, J=7.2 Hz, 1H), 4.62 (s, 1H), 4.58 (d, J=1.2 Hz, 1H), 4.55 (dd, J=16.1, 12.9 Hz, 1H), 4.44 (dd, J=30.8, 12.8 Hz, 1H), 3.81 (d, J=6.5 Hz, 1H), 3.58-3.54 (m, 1H), 3.46 (d, J=5.9 Hz, 1H), 3.35 (d, J=8.6 Hz, 1H). $^{19}$F NMR (376 MHz, CDCl$_3$) δ −163.54 (dd, J=30.6, 16.3 Hz), −172.44 (t, J=23.7 Hz). $^{13}$C NMR (151 MHz, CDCl$_3$) δ 200.14 (d, J=15.8 Hz), 191.56 (d, J=18.8 Hz), 165.72 (s), 165.60 (s), 144.50 (s), 133.58 (s), 133.53 (s), 133.51 (s), 130.07 (s), 129.91 (s), 129.80 (s, 2 carbons overlapping), 129.01 (s), 128.75 (s), 128.54 (s), 128.51 (s), 94.12 (d, J=198.7 Hz), 90.71 (d, J=195.5 Hz), 68.31 (d, J=25.5 Hz), 64.27 (d, J=25.4 Hz), 51.38 (s), 39.24 (d, J=3.7 Hz), 39.10 (dd, J=19.2, 13.0 Hz), 36.48 (dd, J=18.8, 5.1 Hz). m/z HRMS (ESI) found [M+Na]+ 515.1277, C$_{28}$H$_{22}$O$_6$F$_2$ $_{23}$Na requires 515.1277. [α]D$^{20}$=+5.7 (c 1.0, CHCl$_3$).

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

All publications, patents, and patent applications cited herein are hereby incorporated by reference in their entirety for all purposes.

What is claimed is:
1. A method of cyclizing an alkene, said method comprising:
contacting an alkene having the formula:

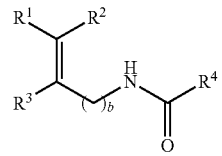

wherein
b is selected from 1 and 2;
R$^1$, R$^2$ and R$^3$ are members independently selected from H, substituted or unsubstituted alkyl, substituted or unsubstituted heteroalkyl, substituted or unsubstituted aryl and substituted or unsubstituted heteroaryl, and
a member selected from R$^1$ and R$^2$, R$^2$ and R$^3$, and R$^1$, R$^2$ and R$^3$, together with the atoms to which they are attached are optionally joined to fowl a ring system; and
R$^4$ is a member selected from substituted or unsubstituted aryl and substituted or unsubstituted heteroaryl, with an ion pair having the formula:

[A]$^{n+}$[B]$^{n-}$, wherein n is 1
and A is

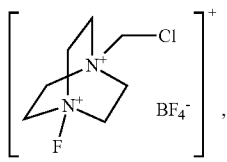

B is a chiral anion having the formula:

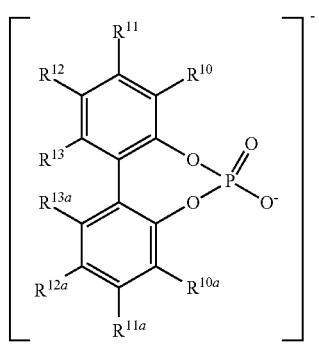

wherein
$R^{10}$, $R^{10a}$, $R^{11}$, $R^{11a}$, $R^{12}$, $R^{12a}$, $R^{13}$, $R^{13a}$ are independently members selected from H, substituted or unsubstituted alkyl, substituted or unsubstituted heteroalkyl, substituted or unsubstituted aryl, substituted or unsubstituted heteroaryl, halogen, CN, CF$_3$, acyl, —SO$_2$NR$^8$R$^9$, —NR$^8$R$^9$, —OR$^8$, —S(O)$_2$R$^8$, —C(O)R$^9$, —COOR$^8$, —CONR$^8$R$^9$, —S(O)$_2$OR$^8$, —OC(O)R$^8$, —C(O)NR$^8$R$^9$, —NR$^8$C(O)R$^9$, —NR$^8$SO$_2$R$^9$ and —NO$_2$, wherein two or more of $R^{10}$, $R^{10a}$, $R^{11}$, $R^{11a}$, $R^{12}$, $R^{12a}$, $R^{13}$, $R^{13a}$, together with the atoms to which they are bonded, are optionally joined to form a ring system which is a member selected from substituted or unsubstituted cycloalkyl, substituted or unsubstituted heterocycloalkyl, substituted or unsubstituted aryl and substituted or unsubstituted heteroaryl
wherein
R$^8$ and R$^9$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, and R$^8$ and R$^9$, together with the atoms to which they are bonded, are optionally joined to form a 5- to 7-membered ring under conditions appropriate to cyclize said alkene.

2. The method according to claim 1, wherein said cyclization of said alkene yields a product having the formula:

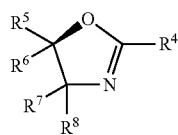

wherein
R$^5$ and R$^6$, together with the atoms to which they are attached, are joined to form a ring system which is a member selected from substituted or unsubstituted aryl, substituted or unsubstituted heteroaryl, substituted or unsubstituted cycloalkyl, and substituted or unsubstituted heterocycloalkyl, wherein said ring system is substituted with at least one member selected from halogen and substituted or unsubstituted aryl; and
R$^7$ and R$^8$ are members independently selected from H, substituted or unsubstituted alkyl and substituted or unsubstituted heteroalkyl.

3. The method according to claim 2, wherein R$^5$ and R$^6$ are joined to form a ring system having the formula:

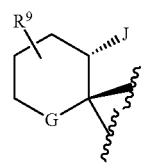

wherein
J is a member selected from halogen and substituted or unsubstituted aryl;
G is a member selected from O and S; and
each R$^9$ is a member independently selected from H, substituted or unsubstituted alkyl, substituted or unsubstituted heteroalkyl, substituted or unsubstituted aryl and substituted or unsubstituted heteroaryl, and two or more R$^9$ moieties, together with the atoms to which they are attached, are optionally joined to form a ring system.

4. The method according to claim 3, wherein R$^5$ and R$^6$ are joined to form a ring system having the formula:

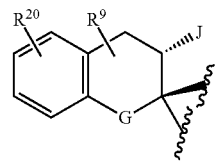

wherein
each R$^{20}$ is a member independently selected from H, substituted or unsubstituted alkyl, substituted or unsubstituted heteroalkyl, substituted or unsubstituted aryl, substituted or unsubstituted heteroaryl, halogen, CN, CF$_3$, acyl, —SO$_2$NR$^{18}$R$^{19}$, —NR$^{18}$R$^{19}$, —OR$^{18}$, —S(O)$_2$R$^{18}$, —C(O)R$^{18}$, —COOR$^{18}$, —CONR$^{18}$R$^{19}$, —S(O)$_2$OR$^{18}$, —OC(O)R$^{18}$, —C(O)NR$^{18}$R$^{19}$, —NR$^{18}$C(O)R$^{19}$, —NR$^{18}$SO$_2$R$^{19}$ and —NO$_2$,
wherein
R$^{18}$ and R$^{19}$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, and R$^{18}$ and R$^{19}$, together with the atoms to which they are bonded, are optionally joined to form a 5- to 7-membered ring.

5. The method according to claim 3, wherein G is O.

6. The method according to claim 3, wherein J is F.

7. The method according to claim 3, wherein each $R^9$ is H.

8. The method according to claim 1, wherein said product is produced with an ee of at least about 80% enantiomeric excess.

* * * * *